United States Patent [19]

Brunner et al.

[11] Patent Number: 5,416,065
[45] Date of Patent: May 16, 1995

[54] HERBICIDAL THIADIAZABICYCLOOCTANES

[75] Inventors: Hans-Georg Brunner, Lausen; Hans Moser, Magden, both of Switzerland; Georg Pissiotas, Lörrach, Germany

[73] Assignee: Ciba-Geigy Corporation, Ardsley, N.Y.

[21] Appl. No.: 154,243

[22] Filed: Nov. 18, 1993

[30] Foreign Application Priority Data

Nov. 27, 1992 [CH] Switzerland .................. 3653/92

[51] Int. Cl.⁶ .................. C07D 513/04; A01N 43/90
[52] U.S. Cl. .................. 501/263; 544/52; 544/584; 544/105; 544/134; 544/368; 546/271; 548/126
[58] Field of Search .................. 548/126; 504/263; 546/271; 544/52, 58.4, 105, 134, 368

[56] References Cited

U.S. PATENT DOCUMENTS

| 4,684,397 | 8/1987 | Nagano et al. ............ 71/96 |
| 4,801,408 | 1/1989 | Nagano et al. ............ 260/508 |
| 4,885,023 | 12/1989 | Yamaguchi et al. ............ 71/90 |

FOREIGN PATENT DOCUMENTS

| 0238711 | 9/1987 | European Pat. Off. . |
| 0304920 | 3/1989 | European Pat. Off. . |
| 5213970 | 2/1993 | Japan ............ 548/126 |
| 9221684 | 12/1992 | WIPO . |

OTHER PUBLICATIONS

Klemann, Pharmazie, 46 573 (1991).
Pharmazie 46(8), pp. 573–575 (1991).
Chem. Abst. 120:2802h (corresponds to JP 5,213,970 (1993).

*Primary Examiner*—Robert Gerstl
*Attorney, Agent, or Firm*—George R. Dohmann; Marla J. Mathias

[57] ABSTRACT

Thiadiazabicyclooctanes of formula I

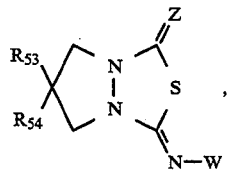

(I)

wherein

Z is oxygen or sulfur;
$R_{53}$ is hydrogen or $C_1$-$C_6$alkyl;
$R_{54}$ is $C_1$-$C_6$alkyl, $C_1$-$C_6$alkoxy, $C_3$-$C_6$alkenyloxy, $C_3$-$C_6$alkynyloxy, hydroxy or $C_1$-$C_6$haloalkoxy; or
$R_{53}$ and $R_{54}$, together with the carbon atom to which they are bonded, form an unsubstituted 3-, 4-, 5- or 6-membered saturated ring;
W is a group of formulae $W_1$ to $W_{10}$

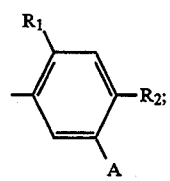

(W₁)

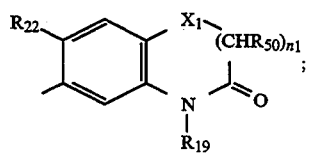

(W₂)

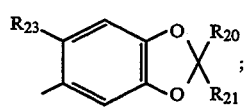

(W₃)

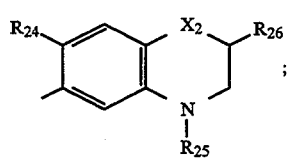

(W₄)

(Abstract continued on next page.)

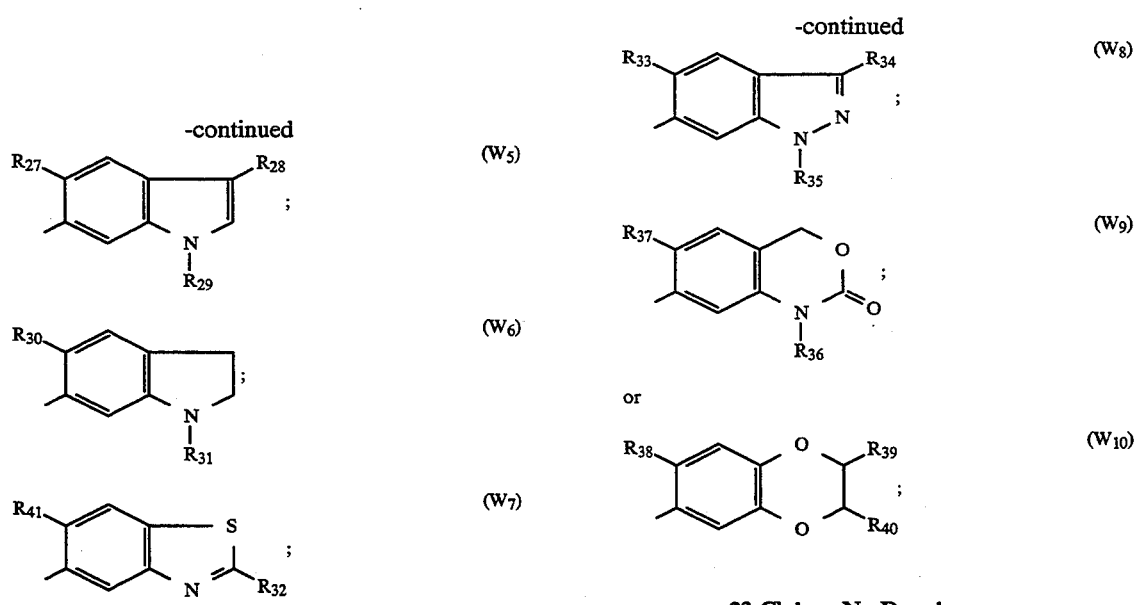
23 Claims, No Drawings

HERBICIDAL THIADIAZABICYCLOOCTANES

The present invention relates to novel, herbicidally active thiadiazabicyclooctanes, to processes for the preparation thereof, to compositions comprising those compounds as active ingredients, and to the use thereof in the control of weeds, especially selectively in crops of useful plants, such as cereals, maize, soybeans, rape, rice and cotton.

Thiadiazabicyclo derivatives having herbicidal action are already known. Such compounds are disclosed, for example, in EP-A-0 238 711, EP-A-0 304 920, U.S. Pat. No. 4,885,023, U.S. Pat. No. 4,684,397 and U.S. Pat. No. 4,801,408.

Novel thiadiazabicyclooctanes having selective herbicidal action have now been found.

The thiadiazabicyclooctanes according to the invention have the formula

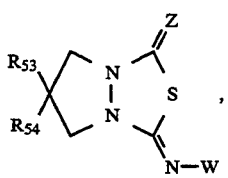

(I)

wherein

Z is oxygen or sulfur;

$R_{53}$ is hydrogen or $C_1$-$C_6$alkyl;

$R_{54}$ is $C_1$-$C_6$alkyl, $C_1$-$C_6$alkoxy, $C_3$-$C_6$alkenyloxy, $C_3$-$C_6$alkynyloxy, hydroxy or $C_1$-$C_6$haloalkoxy; or $R_{53}$ and $R_{54}$, together with the carbon atom to which they are bonded, form an unsubstituted 3-,4-, 5- or 6-membered saturated ring;

W is a group of formulae $W_1$ to $W_{10}$

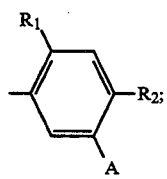
(W$_1$)

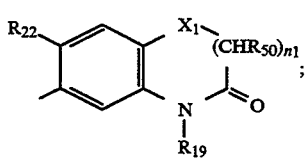
(W$_2$)

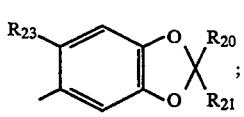
(W$_3$)

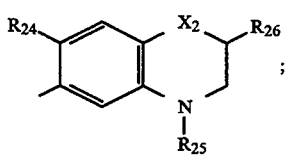
(W$_4$)

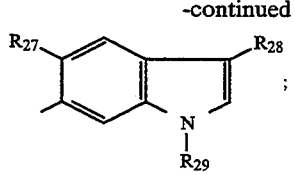
(W$_5$)

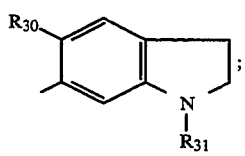
(W$_6$)

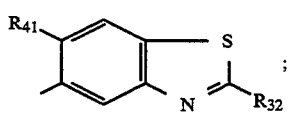
(W$_7$)

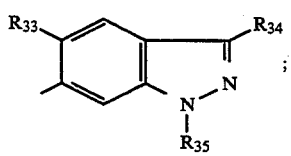
(W$_8$)

(W$_9$)

or

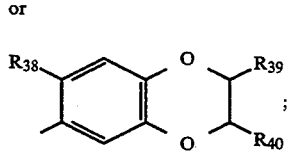
(W$_{10}$)

wherein $R_1$, $R_{22}$, $R_{23}$, $R_{24}$, $R_{27}$, $R_{30}$, $R_{33}$, $R_{37}$, $R_{38}$ and $R_{41}$ are each independently of the others hydrogen or halogen;

$R_2$ is hydrogen, cyano, nitro, halogen, $C_1$-$C_4$alkyl, $C_1$-$C_4$haloalkoxy or $C_1$-$C_4$haloalkyl; is hydrogen, cyano, nitro, $$-COR_3, -X_3R_4, -\underset{\underset{N-OR_{42}}{\|}}{C}-CN, -COR_8, -\underset{\underset{N-OR_{43}}{\|}}{C}-R_{44},$$

$$-\underset{\underset{OR_9\ OR_{10}}{}}{C}-R_{45}, -\underset{\underset{O}{\|}}{C}-X_4-[CHR_{11}(CH_2)_{n2}]-Si(R_{12})_3,$$

$$-N(R_{13})-SO_2-R_{14}, -O-\underset{\underset{O-C_2H_5}{\overset{O}{\|}}}{P}-O-C_2H_5 \text{ or}$$

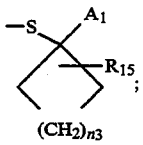

$A_1$ is cyano or $-COR_{16}$;

$R_3$ is halogen, $-X_4-R_5$, amino, $C_1-C_4$alkylamino, di-$C_1$-$C_4$alkylamino, $C_2-C_4$haloalkylamino, di-$C_2$-$C_4$haloalkylamino, $C_1-C_4$alkoxyalkylamino, di-$C_1$-$C_4$alkoxyalkylamino, $C_3$- or $C_4$-alkenylamino, diallylamino, -N-pyrrolidino, -N-piperidino, -N-morpholino,-N-thiomorpholino,-N-piperazino, $-O-N=C(CH_3)-CH_3$ or $-O-CH_2-CH_2-O-N=C(CH_3)-CH_3$;

$R_4$, $R_{42}$ and $R_{43}$ are each independently of the others hydrogen, $C_1-C_{10}$alkyl, $C_1-C_4$alkoxy-$C_1-C_4$alkyl, $C_1-C_4$alkylthio-$C_1-C_4$alkyl, di-$C_1-C_4$alkylamino-$C_1-C_4$alkyl, $C_1-C_8$haloalkyl, $C_2-C_8$alkenyl, $C_2-C_8$haloalkenyl, $C_3-C_8$alkynyl, $C_3-C_7$cycloalkyl, halo-$C_3-C_7$cycloalkyl, $C_1-C_8$alkylcarbonyl, allylcarbonyl, $C_3-C_7$cycloalkylcarbonyl, benzoyl that is unsubstituted or is substituted at the phenyl ring by one to three identical or different substituents selected from halogen, $C_1-C_4$alkyl, $C_1-C_4$haloalkyl, $C_1-C_4$haloalkoxy and $C_1-C_4$alkoxy; $C_1-C_6$alkyl substituted by cyano, nitro, carboxy, $C_1-C_8$alkylthio-$C_1-C_8$alkoxycarbonyl, phenyl, halophenyl, $C_1-C_4$alkylphenyl, $C_1-C_4$alkoxyphenyl, $C_1-C_4$haloalkylphenyl, $C_1-C_4$haloalkoxyphenyl, $C_1-C_6$alkoxycarbonyl, $C_1-C_4$alkoxy-$C_1-C_8$alkoxycarbonyl, $C_3-C_8$alkenyloxycarbonyl, $C_3-C_8$alkynyloxycarbonyl, $C_1-C_8$alkylthiocarbonyl, $C_3-C_8$alkenylthiocarbonyl, $C_3-C_8$alkynylthiocarbonyl, carbamoyl, $C_1-C_4$alkylaminocarbonyl, di-$C_1-C_4$alkylaminocarbonyl; phenylaminocarbonyl that is unsubstituted or is substituted at the phenyl by one to three identical or different substituents selected from halogen, $C_1-C_4$alkyl, $C_1-C_4$haloalkyl, $C_1-C_4$haloalkoxy and $C_1-C_4$alkoxy or by one substituent selected from cyano and nitro; dioxolan-2-yl that is unsubstituted or substituted by one or two $C_1-C_4$alkyl radicals; or dioxanyl that is unsubstituted or substituted by one or two $C_1-C_4$alkyl radicals;

$R_5$ is hydrogen, $C_1-C_{10}$alkyl, $C_1-C_4$alkoxy-$C_1-C_4$alkyl, $C_2-C_8$haloalkyl, $C_1-C_{10}$alkyl-thio-$C_1-C_4$alkyl, di-$C_1-C_4$alkylamino-$C_1-C_4$alkyl, cyano-$C_1-C_8$alkyl, $C_3-C_8$alkenyl, $C_3-C_8$haloalkenyl, $C_3-C_8$alkynyl, $C_3-C_7$cycloalkyl, $C_3-C_7$cycloalkyl-$C_1-C_4$alkyl, halo-$C_3-C_7$cycloalkyl, or benzyl that is unsubstituted or is substituted at the phenyl ring by one to three identical or different substituents selected from halogen, $C_1-C_4$alkyl, $C_1-C_4$haloalkyl, $C_1-C_4$haloalkoxy and $C_1-C_4$alkoxy; or is an alkali metal, an alkaline earth metal or an ammonium ion; or is the group $-[CHR_6(CH_2)_{n4}]-COOR_7$;

$R_6$, $R_{20}$, $R_{21}$, $R_{26}$, $R_{28}$, $R_{32}$, $R_{34}$, $R_{39}$, $R_{40}$, $R_{46}$, $R_{47}$, $R_{49}$, $R_{50}$, $R_{51}$ and $R_{52}$ are each independently of the others hydrogen or $C_1-C_4$alkyl;

$R_7$ and $R_{48}$ are each independently of the other hydrogen, $C_1-C_6$alkyl, $C_3-C_8$alkenyl, $C_3-C_8$alkynyl, $C_1-C_8$alkoxy-$C_2-C_1-8$alkyl, $C_1-C_8$alkylthio-$C_1-C_8$alkyl or $C_3-C_7$cycloalkyl;

$R_8$ is hydrogen or $C_1-C_4$alkyl;

$R_{44}$ and $R_{45}$ are each independently of the other hydrogen, $C_1-C_4$alkyl, $C_1-C_4$haloalkyl or $C_1-C_4$alkoxy-$C_1-C_4$alkyl;

$R_9$ and $R_{10}$ are each independently of the other $C_1-C_4$alkyl, $C_2-C_4$haloalkyl or $C_2-C_8$alkoxyalkyl; or $R_9$ and $R_{10}$ together are an ethano-, a propano- or a cyclohexane-1,2-diyl bridge, those groups either being unsubstituted or being substituted by one or two radicals selected from the group $C_1-C_4$alkyl, $C_1-C_4$haloalkyl and $C_1-C_4$-hydroxyalkyl;

$R_{11}$ is hydrogen, $C_1-C_5$alkyl or $C_3-C_7$alkenyl;

$R_{12}$ is $C_1-C_8$alkyl;

$R_{13}$ is hydrogen, $C_1-C_5$alkyl, benzyl, $C_1-C_4$haloalkyl, $C_3-C_8$alkenyl or $C_3-C_8$alkynyl;

$R_{14}$ is $C_1-C_6$alkyl, $C_1-C_5$haloalkyl or di-$C_1-C_4$alkylamino;

$R_{15}$ is hydrogen, fluorine, chlorine, bromine, $C_1-C_4$alkyl or trifluoromethyl;

$R_{16}$ is chlorine, $-X_5-R_{17}$, amino, $C_1-C_4$alkylamino, di-$C_1-C_4$alkylamino, $C_2-C_4$haloalkylamino, di-$C_2-C_4$haloalkylamino, $C_1-C_4$alkoxyalkylamino, di-$C_1-C_4$alkoxyalkylamino, $C_3-C_4$alkenylamino, diallylamino,-N-pyrrolidino,-N-piperidino, -N-morpholino, -N-thiomorpholino, -N-piperazino, or the group $-O-N=C(CH_3)-CH_3$, $-O-CH_2-CH_2-O-N=C(CH_3)-CH_3$ or -N(OR_{46})-R_6$;

$R_{17}$ is hydrogen, $C_1-C_{10}$alkyl, $C_1-C_4$alkoxy-$C_1-C_4$alkyl, $C_2-C_8$haloalkyl, $C_1-C_{10}$alkyl-thio-$C_1-C_4$alkyl, di-$C_1-C_4$alkylamino-$C_1-C_4$alkyl, cyano-$C_1-C_8$alkyl, $C_3-C_8$alkenyl, $C_3-C_8$haloalkenyl, $C_3-C_8$alkynyl, $C_3-C_7$cycloalkyl, $C_3-C_7$cycloalkyl-$C_1-C_4$alkyl, halo-$C_3-C_7$cycloalkyl, or benzyl that is unsubstituted or is substituted at the phenyl ring by one to three identical or different substituents selected from halogen, $C_1-C_4$alkyl, $C_1-C_4$haloalkyl, $C_1-C_4$haloalkoxy and $C_1-C_4$alkoxy; or is an alkali metal, an alkaline earth metal or an ammonium ion, or is the group $-[CHR_{47}-(CH_2)_m]-COOR_{48}$ or $-[CHR_{49}-(CH_2)_t-Si(R_{18})_3]$;

m is 0, 1, 2, 3 or 4;

t is 0, 1, 2, 3 or 4;

$R_{18}$ is $C_1-C_4$alkyl;

$R_{19}$ is hydrogen, $C_1-C_6$alkyl, $C_2-C_4$alkenyl or $C_2-C_6$alkynyl; halo-substituted $C_1-C_6$alkyl, $C_2-C_4$alkenyl or $C_3-C_6$alkynyl; $C_1-C_4$aalkoxy-$C_1-C_4$alkyl, $C_1-C_4$alkoxy-$C_1-C_2$alkoxy-$C_1-C_2$alkyl, 1-phenylpropen-3-yl, $C_1-C_6$alkyl substituted by cyano or by $C_3-C_6$cycloalkyl; carboxy-$C_1-C_4$alkyl, $C_1-C_6$alkoxycarbonyl-$C_1-C_4$alkyl, $C_2-C_6$haloalkoxycarbonyl-$C_1-C_4$alkyl, $C_1-C_4$alkoxy-$C_1-C_2$alkoxycarbonyl-$C_1-C_4$alkyl, $C_1-C_6$alkoxycarbonyl-$C_1-C_2$alkoxycarbonyl-$C_1-C_4$alkyl, $C_3-C_6$cycloalkyl-$C_1-C_2$alkoxycarbonyl-$C_1-C_4$alkyl, $C_1-C_5$alkylaminocarbonyl-$C_1-C_4$alkyl, di-$C_1-C_4$alkylamino-$C_1-C_4$alkyl, di-$C_1-C_5$alkylaminocarbonyl-$C_1-C_4$alkyl, $C_3-C_6$cycloalkyl, $C_1-C_4$alkylthio-$C_1-C_4$alkyl, benzyl or halo-substituted benzyl, $C_1-C_8$alkylcarbonyl

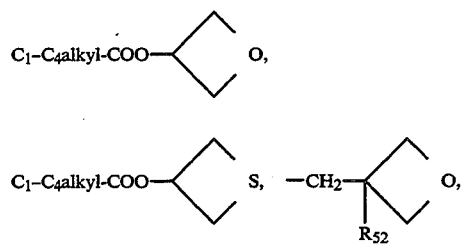

$C_1-C_4$alkylthiocarbonyl-$C_1-C_4$alkyl, or the group $-[CHR_{47}-(CH_2)_m]COX_6-CHR_{47}-(CH_2)_m-COOR_{48}$;

$R_{25}$, $R_{29}$, $R_{31}$, $R_{35}$ and $R_{36}$ are each independently of the others hydrogen, $C_1-C_4$alkyl, $C_1-C_6$haloalkyl, $C_3-C_8$alkenyl, $C_3-C_8$haloalkenyl, $C_3-C_8$alkynyl, $C_1C_4$alkoxy-$C_1-C_8$alkyl, cyano-$C_1-C_4$alkyl, $C_1-C_8$alkoxycarbonyl-$C_1-C_4$alkyl, $C_3-C_7$cycloalkyl, $C_3-C_7$cycloalkyl-$C_1-C_4$alkyl, benzyl, $C_1-C_4$alkyl substituted by -N-morpholino, -N-thiomorpholino or by -N-piperazino, di-$C_1-C_4$ alkylamino-$C_1-C_4$alkyl, $C_1$-

$C_4$alkylaminocarbonyl-$C_1$-$C_4$alkyl, di-$C_1$-$C_4$alkylaminocarbonyl-$C_1$-$C_4$alkyl, $C_1$-$C_4$alkoxycarbonyl or $C_1$-$C_4$alkylcarbonyl;

$X_1$, $X_2$, $X_3$, $X_4$, $X_5$ and $X_6$ are each independently of the others oxygen or sulfur;

$n_1$, $n_2$, $n_3$ and $n_4$ are each independently of the others 0, 1, 2, 3 or 4; with the provisos that at least one of $R_1$, $R_2$ and A is different from hydrogen; and that when $R_{53}$ is hydrogen, $R_{54}$ is different from $C_1$-$C_4$alkyl; and the salts and stereoisomers thereof.

In the above definitions, halogen is to be understood as being fluorine, chlorine, bromine and iodine, preferably fluorine, chlorine and bromine.

Suitable alkyl groups are straight-chained or branched, for example methyl, ethyl, n-propyl, isopropyl, n-butyl, isobutyl, sec-butyl, tert-butyl, and the various isomeric pentyl, hexyl, heptyl, octyl, nonyl and decyl radicals.

Suitable as haloallcyl are alkyl groups mono- or poly-substituted, especially mono- to tri-substituted, by halogen, wherein halogen is individually bromine or iodine, and especially fluorine or chlorine, for example fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl; preferably difluorochloromethyl, trifluoromethyl, dichlorofluoromethyl and trichloromethyl.

Alkoxy is, for example, methoxy, ethoxy, n-propoxy, isopropoxy, n-butoxy, isobutoxy, sec-butoxy and tert-butoxy; preferably methoxy, ethoxy and isopropoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy; preferably difluoromethoxy, trifluoromethoxy and 2-chloroethoxy.

Alkylthio is, for example, methylthio, ethylthio, n-propylthio, isopropylthio, n-butylthio, isobutylthio, sec-butylthio, tert-butylthio or isomeric pentylthio, preferably methylthio and ethylthio.

Alkenyl is to be understood as being straight-chained or branched alkenyl, such as vinyl, allyl, methallyl, 1-methylvinyl, but-2-en-1-yl, pentenyl, 2-hexenyl or 3-heptenyl. Alkenyl radicals having a chain length of from 2 to 4 carbon atoms are preferred.

The alkynyl radicals appearing in the definitions of the substituents may be straight-chained or branched, such as ethynyl, propargyl, 3-butynyl, 1-methylpropargyl, 1-pentynyl or 2-hexynyl. Ethynyl and propargyl are preferred.

Cycloalkyl is, for example, cyclopropyl, dimethylcyclopropyl, cyclobutyl, cyclopentyl, methylcyclopentyl, cyclohexyl or cycloheptyl, but preferably cyclopropyl, cyclopentyl or cyclohexyl.

Alkoxycarbonyl is, for example, methoxycarbonyl, ethoxycarbonyl, n-propoxycarbonyl, isopropoxycarbonyl or n-butoxycarbonyl, preferably methoxycarbonyl or ethoxycarbonyl.

Alkoxyalkyl is, for example, methoxymethyl, ethoxymethyl, propoxymethyl, methoxyethyl, ethoxyethyl, propoxyethyl, methoxypropyl, ethoxypropyl or propoxypropyl.

Alkylthioalkyl is, for example, methylthiomethyl, ethylthiomethyl, methylthioethyl, ethylthioethyl or isopropylthioethyl.

Alkylaminoalkyl is, for example, methylaminoethyl, dimethylaminoethyl, ethylaminoethyl or diethylaminoethyl.

Cyanoalkyl is, for example, cyanomethyl, cyanoethyl or cyanopropyl.

Halocycloalkyl is, for example, 2,2-dichlorocyclopropyl or pentachlorocyclohexyl.

Alkylsulfonyl is, for example, methylsulfonyl, ethylsulfonyl, propylsulfonyl or butylsulfonyl, preferably methylsulfonyl or ethylsulfonyl.

Phenyl, also as part of a substituent such as phenoxy, phenylthio, phenoxycarbonyl, phenylaminocarbonyl, benzyl or benzoyl, can generally be unsubstituted or substituted. The substituents may be in the ortho-, meta- and/or para-position(s). Preferred substituent positions are the ortho- and para-positions to the ring-linkage point. Preferred substituents are halogen atoms.

In the further substituents that are composed of several basic elements, the elements are as defined above by way of example.

The salts of the compounds of formula I having acid protons, especially of the derivatives having carboxylic acid groups (A=—C(O)—$X_4R_5$ wherein $X_4$ is oxygen and $R_5$ is hydrogen), are, for example, alkali metal salts, such as sodium and potassium salts; alkaline earth metal salts, such as calcium and magnesium salts; ammonium salts, i.e. unsubstituted ammonium salts and mono- or poly-substituted ammonium salts, for example triethylammonium and methylammonium salts; or salts with other organic bases.

Examples of amines suitable for salt formation are primary, secondary and tertiary aliphatic and aromatic amines, such as methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methylhexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, diethanolamine, trimethylamine, triethylamine, tri-n-propylamine, triisopropylamine, tri-n-butylamine, triisobutylamine, tri-sec-butylamine, tri-n-amylamine; heterocyclic amines, such as pyridine, quinoline, isoquinoline, morpholine, thiomorpholine, N-methylmorpholine, N-methyl-thiomorpholine, piperidine, pyrrolidine, indoline, quinuclidine and azepine; primary arylamines, such as anilines, methoxyanilines, ethoxyanilines, o,m,p-toluidines, phenylenediamines, benzidines, naphthylamines and o,m,p-chloroanilines.

Because at least one asymmetric carbon atom may be present in the compounds of formula I, for example in the ester and ether derivatives having substituted aliphatic and alicyclic groups, the compounds may occur both as optically active individual isomers and in the form of racemic mixtures. In the present invention, the compounds of formula I are to be understood as including both the pure optical antipodes and the racemates. Unless the individual optical antipodes are referred to specifically, there are to be understood by the formula given those racemic mixtures that are formed in the preparation process indicated. If an aliphatic C=C or C=N double bond is present, geometric isomerism may also occur.

Preference is given to compounds of formula I wherein Z is oxygen.

Preference is likewise given to compounds of formula Ia

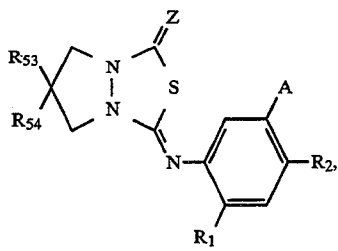

wherein Z, A, $R_1$, $R_2$, $R_{53}$ and $R_{54}$ are as defined for formula I.

Of those compounds, special preference is given to those wherein A is

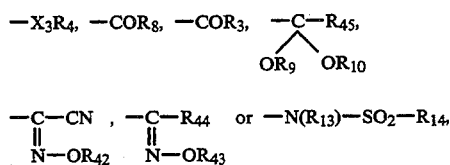

$X_3$ being especially sulfur and $R_4$ being $C_1$-$C_6$alkyl substituted by $C_1$-$C_6$alkoxycarbonyl.

In especially preferred compounds of formula Ia, $R_1$ and $R_2$ are halogen; $R_1$ is especially fluorine and $R_2$ is especially chlorine.

The preferred compounds likewise include those of formula Ib

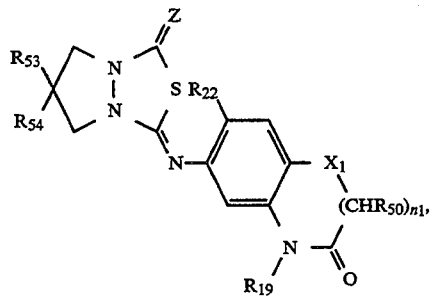

wherein Z, $R_{19}$, $R_{22}$, $X_1$, $R_{50}$, $R_{53}$, $R_{54}$ and $n_1$ are as defined for formula I.

Of those compounds, special preference is given to those wherein $R_{19}$ is $C_1$-$C_4$alkyl, $C_3$-or $C_4$-alkenyl, $C_3$- or $C_4$-haloalkenyl, $C_3$-$C_6$alkynyl, $C_1$-$C_4$alkoxy-$C_1$-$C_4$alkyl, cyano-$C_1$-$C_4$alkyl, $C_1$-$C_6$alkoxycarbonyl-$C_1$-$C_4$alkyl, $C_3$-$C_6$cycloalkyl, $C_3$-$C_6$cycloalkyl-$C_1$-$C_4$alkyl, benzyl, di-$C_1$-$C_4$alkylamino-$C_1$-$C_4$alkyl, $C_1$-$C_4$alkylaminocarbonyl-$C_1$-$C_4$alkyl, di-$C_1$-$C_4$alkylaminocarbonyl-$C_1$-$C_4$alkyl, $C_1$-$C_4$alkoxycarbonyl or $C_1$-$C_4$alkylcarbonyl.

Of those compounds, preference is given especially to those wherein Z is oxygen; $R_{19}$ is $C_1$-$C_3$alkyl, $C_1$-$C_3$alkoxycarbonyl-$C_1$- or-$C_2$-alkyl or $C_3$- or $C_4$-alkynyl; $R_{22}$ is hydrogen or fluorine; $R_{50}$ is hydrogen; and $n_1$ is 0 or 1.

Compounds of formula I wherein $R_{53}$ and $R_{54}$ are $C_1$-$C_4$alkyl are especially important.

Of those compounds, those of formula I wherein $R_{53}$ and $R_{54}$ are each independently of the other methyl or ethyl are very especially important.

Compounds of formula I wherein $R_{53}$ and $R_{54}$, together with the carbon atom to which they are bonded, form an unsubstituted 3- or 5-membered ring are also very important.

Compounds of formula I wherein $R_{53}$ is hydrogen; and $R_{54}$ is $C_1$-$C_3$alkoxy, $C_3$-$C_5$alkenyl-oxy, $C_3$-$C_5$alkynyloxy or $C_1$-$C_3$haloalkoxy are likewise of great importance.

Of those compounds, preference is given especially to those wherein $R_{54}$ is $C_1$-$C_3$alkoxy or $C_1$-$C_3$haloalkoxy. In particular, of those compounds, those wherein $R_{54}$ is methoxy, isopropoxy or difluoromethoxy are of very great importance.

Individual compounds from the scope of formula I that may be mentioned are:

8-(4-chloro-2-fluoro-5-isopropoxy-phenylimino)-3,3-dimethyl-7-thia-1,5-diazabicyclo-[3.3.0]octan-6-one;

8-(4-chloro-2-fluoro-5-isopropoxy-phenylimino)-3-methoxy-7-thia-1,5-diazabicyclo[3.3.0]octan-6-one;

8-(4-chloro-2-fluoro-5-isopropoxy-phenylimino)-3-difluoromethoxy-7-thia-1,5-diazabicyclo[3.3.0]octan-6-one; and 8-(4-chloro-2-fluoro-5-isopropoxy-phenylimino)-3,3-ethanediyl-7-thia-1,5-diazabicyclo[3.3.0]octan-6-one.

The process according to the invention for the preparation of a compound of formula I

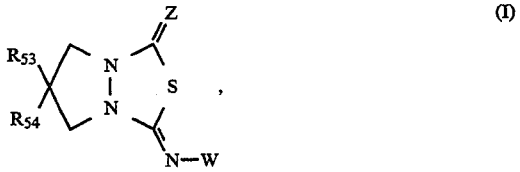

wherein Z, W, $R_{53}$ and $R_{54}$ are as defined for formula I, is carried out analogously to known processes and comprises converting an isothiocyanate of formula II $$S=C=N-W \qquad (II),$$

wherein W is as defined for formula I, with a compound of formula III

wherein $R_{53}$ and $R_{54}$ are as defined for formula I, into a compound of formula IV

and then reacting the latter with a compound of formula V $$CZCl_2 \qquad (V),$$

wherein Z is oxygen or sulfur.

The reaction of the isothiocyanates of formula II with the compounds of formula III is advantageously carried out in an inert organic solvent at temperatures of from −5° C. to the boiling temperature of the solvent, especially from 0° to +50° C., preferably at room temperature. Examples of suitable solvents for this reaction are toluene, xylenes, ethyl acetate and acetonitrile.

The reaction of a compound of formula IV with a compound of formula V is advantageously carried out in an inert organic solvent at low temperatures, preferably from 0° to +50° C., especially from 0° to +15° C.

The starting compounds of formulae II and III required for the preparation process according to the invention are either known or they can be prepared analogously to processes known from the literature. The preparation of such compounds from 1,3-dibromopropanes and hydrazine is described, for example, in J. Am. Chem. Soc. 88, 3959–3963 (1966).

Compounds of formula IIIa

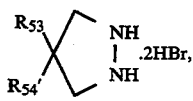  (IIIa)

wherein $R_{53}$ is hydrogen or $C_1$-$C_6$alkyl; and $R_{54}'$ is $C_1$-$C_6$alkyl; or $R_{53}$ and $R_{54}'$, together with the carbon atom to which they are bonded, form an unsubstituted 3-, 4-, 5- or 6-membered saturated ring, can be prepared in accordance with Reaction Scheme 1.

Reaction scheme 1:

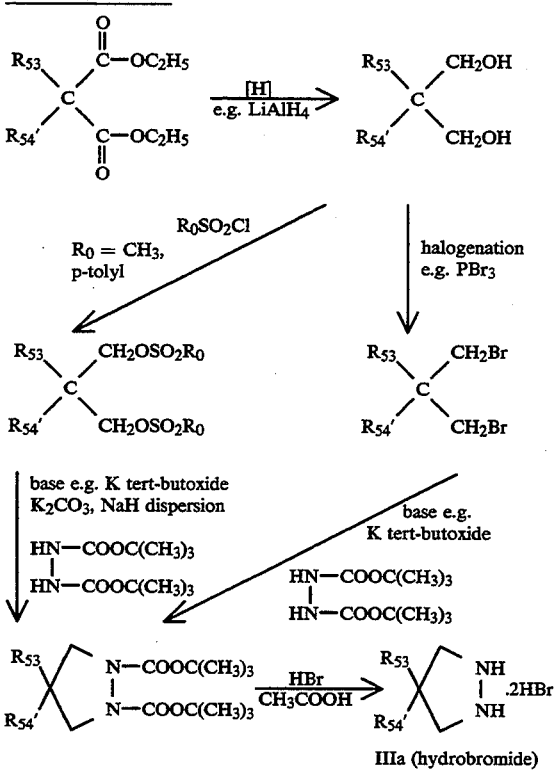

Compounds of formula IIIb

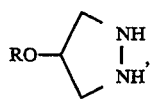  (IIIb)

wherein R is $C_1$-$C_6$alkyl, $C_3$-$C_6$alkenyl, $C_3$-$C_6$alkynyl or $C_1$-$C_6$haloalkyl, can be prepared in accordance with Reaction Scheme 2.

Reaction scheme 2:

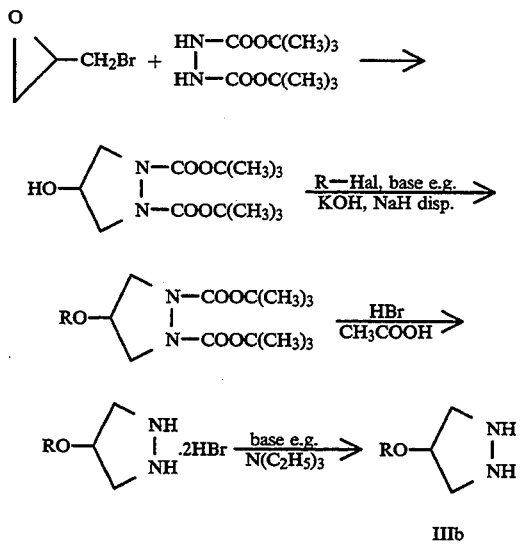

The isothiocyanates of formula II are known or can be prepared analogously to known processes. Such compounds are described, for example, in EP-A-0 304 920, EP-A-0 238 711, EP-A-0 409 025, EP-A-0 373 461, EP-A-0 311 135 and DE-OS-3 724 098.

The compounds of formula I are generally used successfully at rates of application of from 0.001 to 2 kg/ha, especially from 0.005 to 1 kg/ha. The concentration required to achieve the desired effect can be determined by experiment. It is dependent upon the type of action, the stage of development of the crop plant and of the weed, and also upon the application (place, time, method) and, in dependence on those parameters, can vary within wide limits.

When used at relatively low rates of application, the compounds of formula I are distinguished by growth-inhibiting and herbicidal properties that make them outstandingly suitable for use in crops of useful plants, especially in cereals, maize, rape, soybeans, rice and cotton, the use thereof in soybean crops being very especially preferred.

The invention relates also to herbicidal compositions comprising a novel compound of formula I, and to methods of inhibiting plant growth.

Various methods and techniques are suitable for using a compound of formula I or a composition comprising such a compound as active ingredient for regulating plant growth. The following are examples thereof:

i) Seed dressing a) Dressing the seeds with a wettable powder formulation of an active ingredient by shaking in a vessel until the formulation is evenly distributed over the surface of the seeds (dry dressing). Up to 4 g of a compound of formula I (in the case of a 50 % formulation: up to 8.0 g of wettable powder) are used per 1 kg of seed.

b) Dressing the seeds with an emulsifiable concentrate of the active ingredient or with an aqueous solution of a wettable powder formulation of a compound of formula I according to method a) (wet dressing).

c) Dressing by immersing the seeds in a mixture comprising up to 1000 ppm of a compound of formula I for 1 to 72 hours and, if desired, subsequently drying the seeds (seed soaking).

Dressing the seed or treating the germinated seedling are naturally the preferred methods of application since the active ingredient treatment is directed wholly at the target crop. Normally 0.001 g to 4.0 g of active ingredient are used per 1 kg of seed, although, depending on the method employed, which also allows the addition of other active ingredients or micronutrients, amounts that exceed or fall short of the specified concentration limits may be employed (repeat dressing).

ii) Controlled release of active ingredient

A solution of the active ingredient is applied to mineral granule carriers or polymerised granules (urea/formaldehyde) and allowed to dry. If desired, a coating may be applied (coated granules) that allows the active ingredient to be released in metered amounts over a specific period of time.

The compounds of formula I are used in unmodified form, as obtainable from synthesis, or preferably together with the adjuvants conventionally employed in formulation technology, and are therefore formulated in known manner, e.g. into emulsifiable concentrates, directly sprayable or dilutable solutions, dilute emulsions, wettable powders, soluble powders, dusts, granules and also encapsulations in, e.g. polymer substances. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures comprising the compound (active ingredient) of formula I and, where appropriate, one or more solid or liquid adjuvants, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, such as mixtures of alkylbenzenes, e.g. xylene mixtures or alkylated naphthalenes; aliphatic and cycloaliphatic hydrocarbons, such as paraffins, cyclohexane or tetrahydronaphthalene; alcohols, such as ethanol, propanol or butanol; glycols and their ethers and esters, such as propylene glycol or dipropylene glycol ether; ketones, such as cyclohexanone, isophorone or diacetone alcohol; strongly polar solvents, such as N-methyl-2-pyrrolidone, dimethyl sulfoxide or water; vegetable oils and esters thereof, such as rape oil, castor oil or soybean oil; and, where appropriate, also silicone oils. The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. Fatty acid methyltaurin salts may also be mentioned.

More frequently, however, so-called synthetic surfactants are used, especially fatty alcohol sulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzLmidazole derivatives preferably contain 2 sulfonic acid groups and one fatty acid radical containing 8 to 22 carbon atoms. Examples of alkylarylsulfonates arc the sodium, calcium or triethanolaminc salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants arc preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphafic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxy-polyethoxyethanol, polyethylene glycol and octylphenoxy-polyethoxyethanol.

Fatty acid esters of polyoxyethylene sorbitan, e.g. polyoxyethylene sorbitan trioleate, are also suitable.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxylower alkyl radicals. The salts are preferably in the form of halides, methyl sulfates or ethyl sulfates, e.g. stearyltrimethyl-ammonium chloride or benzyldi(2-chloroethyl)ethylammonium bromide.

The surfactants customarily employed in formulation technology are described inter alia in the following publications:

"Mc Cutcheon's Detergents and Emulsifiers Annual", Mc Publishing Corp., Glen Rock, N.J., 1988.

M. and J. Ash, "Encyclopedia of Surfactants", Vol. I-III, Chemical Publishing Co., New York, 1980-1981.

Dr. ttelmut Stache "Tensid-Taschenbuch" (Surfactant Flandbook), Carl Hanser Verlag, Munich/Vienna 1981.

The herbicidal compositions usually comprise 0.1 to 99 %, preferably 0.1 to 95 %, of a compound of formula I, 1 to 99 % of a solid or liquid adjuvant, and 0 to 25 %, preferably 0.1 to 25 %, of a surfactant.

Whereas commercial products are preferably formulated as concentrates, the end user will normally employ dilute formulations.

The compositions may also comprise further ingredients such as stabilisers, e.g. vegetable oils and epoxidised vegetable oils (epoxidised coconut oil, rape oil or soybean oil), antifoams, e.g. silicone oil, preservatives, viscosity regulators, binders and tackifiers, as well as fertilisers or other active ingredients for obtaining special effects.

Preferred formulations have especially the following composition (throughout, percentages are by weight)

| Emulsifiable concentrates: | | |
| --- | --- | --- |
| active ingredient: | 1 to 90%, | preferably 5 to 50% |
| surface-active agent: | 5 to 30%, | preferably 10 to 20% |
| liquid carrier: | 15 to 94%, | preferably 70 to 85% |
| Dusts: | | |
| active ingredient: | 0.1 to 10%, | preferably 0.1 to 1% |
| solid carrier: | 99.9 to 90%, | preferably 99.9 to 99% |
| Suspension concentrates: | | |
| active ingredient: | 5 to 75%, | preferably 10 to 50% |
| water | 94 to 24%, | preferably 88 to 30% |
| surface-active agent: | 1 to 40%, | preferably 2 to 30% |
| Wettable powders: | | |
| active ingredient: | 0.5 to 90%, | preferably 1 to 80% |
| surface-active agent: | 0.5 to 20%, | preferably 1 to 15% |
| solid carrier: | 5 to 95%, | preferably 15 to 90% |
| Granules: | | |
| active ingredient | 0.5 to 30%, | preferably 3 to 15% |
| solid carrier | 99.5 to 70%, | preferably 97 to 85% |

A. Preparation Examples

Example P1

Preparation of 2,3-diazaspim[4.2]cycloheptane-2,3-dicarboxylic acid tert-butyl ester

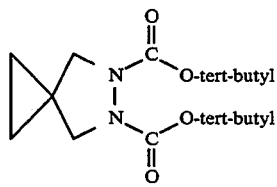

At a maximum of 30° C., 9.1 g of hydrazine-N,N'-dicarboxylic acid di-tert-butyl ester in 20 ml of N,N-dimethylformamide are added dropwise to a suspension of 3.1 g of a 60 % sodium hydride dispersion in 40 ml of N,N-dimethylformamide. After stirring for 1 hour at 22° C., 10.0 g of 1,1-cyclopropane dimethanol dimethanesulfonate in 20 ml of N,N-dimethylformamide are added dropwise in the form of a suspension to the reaction mixture, which is then stirred for 18 hours at 22° C. The resulting yellow suspension is poured onto 700 ml of ice water and the product that has precipitated is suction-filtered and dried in a desiccator to yield 6.8 g of the desired product, 2,3-diazaspiro[4.2]cyclo-heptane-2,3-dicarboxylic acid tert-butyl ester in the form of wax-like crystals; m.p. 60°-70° C.

Example P2

Preparation of 2,3-diazaspiro[4.2]cycloheptane dihydrobromide

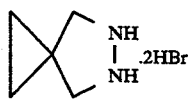

At 0-5° C., 50 ml of a solution of hydrogen bromide in acetic acid (33 %) are added dropwise to a solution of 29.8 g of 2,3-diazaspiro[4.2]cycloheptane-2,3-dicarboxylic acid tertbutyl ester in 500 ml of diethyl ether. After stirring for 3 hours at 0°-5° C., the precipitate that has formed is suction-filtered, washed with diethyl ether and dried in vacuo to yield 23.3 g of the desired 2,3-diazaspiro[4.2]cycloheptane dihydrobromide in the form of white, hygroscopic crystals.

Example P3

Preparation of 4-hydroxypyrazolidine-N,N'-dicarboxylic acid di-tert-butyl ester

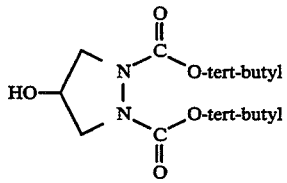

46.4 g of hydrazine-N,N'-dicarboxylic acid di-tert-butyl ester, 69.0 g of potassium carbonate, 3.3 g of potassium iodide, 20 ml of tetrabutylammonium fluoride (1 molar solution in tetrahydrofuran) and 21 ml of epi-bromohydrin are boiled under reflux for 48 hours in 400 ml of ethyl methyl ketone. The resulting suspension is concentrated, and 500 ml of diethyl ether are added thereto; the reaction mixture is then filtered and the filtrate is concentrated. Purification of the crude product by means of column chromatography yields 27.1 g of the desired 4-hydroxy-pyrazolidine-N,N'-dicarboxylic acid di-tert-butyl ester in the form of white crystals; m.p. 100°–102° C.

Example P4

Preparation of 4-hydroxy-pyrazolidine dihydrobromide

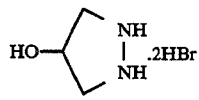

At 22° C., 24 ml of a solution of hydrogen bromide in acetic acid (33 %) are added dropwise to a solution of 11.5 g of 4-hydroxy-pyrazolidine-N,N'-dicarboxylic acid di-tert-butyl ester in 160 ml of diethyl ether. After stirring for 3 hours at 22° C., 200 ml of diethyl ether are added and the product that has precipitated is filtered off and dried under a high vacuum at 50° C. to yield 9.4 g of 4-hydroxy-pyrazolidine dihydrobromide in the form of light brown hygroscopic crystals.

Example P5

Preparation of 4-methoxy-pyrazolidine-N,N'-dicarboxylic acid di-tert-butyl ester

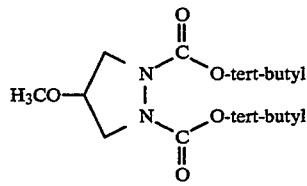

At 0°–5° C., 1.2 g of a sodium hydride dispersion (80 %) are added in portions to a solution of 8.6 g of 4-hydroxy-pyrazolidine-N,N'-dicarboxylic acid di-tert-butyl ester in 90 ml of N,N-dimethylformamide. After stirring for 30 minutes at 0°–5° C., a solution of 2.5 ml of methyl iodide in 10 ml of N,N-dimethylformamide is added dropwise thereto. Stirring is then continued for 3 hours at 0°–5° C. and then 500 ml of diethyl ether are added thereto. The organic phase is washed with water, dried over sodium sulfate and concentrated to yield 8.0 g of the desired product, 4-methoxy-pyrazolidine-N,N'-dicarboxylic acid di-tertbutyl ester, in the form of a yellow oil.

Example P6

4-Methoxy-pyrazolidine dihydrobromide is obtained analogously to Example P5 using 4-methoxy-pyrazolidine-N,N'-dicarboxylic acid di-tert-butyl ester.

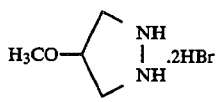

Example P7

Preparation of 4-difluoromethoxy-pyrazolidine-N,N'-dicarboxylic acid di-tert-butyl ester

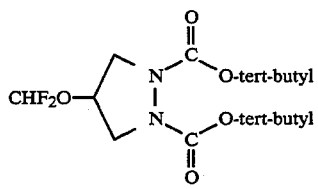

0.2 g of tetrabutylammonium fluoride and 5.6 g of potassium hydroxide powder are added to a solution of 6.9 g of 4-hydroxy-pyrazolidine-N,N'-dicarboxylic acid di-tert-butyl ester in 60 ml of tetrahydrofuran. At a maximum of 45° C., 8.0 g of chlorodifluoromethane are introduced. The reaction solution is then filtered, concentrated and purified by means of column chromatography to yield 2.7 g of the desired product, 4-difluoromethoxy-pyrazolidine-N,N'-dicarboxylic acid di-tert-butyl ester, in the form of a yellow oil.

Example P8

4-Difluoromethoxy-pyrazolidine dihydrobromide is obtained analogously to Example P5 using 4-difluoromethoxy-pyrazolidine-N,N'-dicarboxylic acid di-tert-butyl ester.

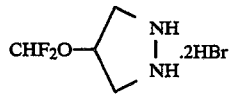

Example P9

Preparation of 4,4-dimethyl-pyrazolidine N,N'-dicarboxylic acid di-tert-butyl ester

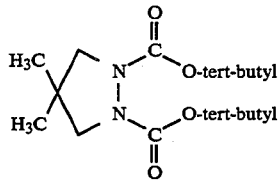

41.8 g of hydrazine-N,N'-dicarboxylic acid di-tert-butyl ester, 74.5 g of potassium carbonate, 52.0 g of 2,2-dimethyl-1,3-propanediol dimethanesulfonate and 2.0 g of potassium iodide are stirred for 48 hours at 120°–130° C. in 360 ml of N,N-dimethylformamide. The reaction mixture is then concentrated; diethyl ether is added and the organic phase is washed with water. Mter drying over sodium sulfate, the reaction mixture is concentrated and purified by means of column chromatography to yield 1.1 g of the desired product, 4,4-dimethyl-pyrazolidine-N,N'-dicarboxylic acid di-tert-butyl ester, in the form of white crystals.

Example P 10

4,4-Dimethylpyrazolidine dihydrobromide is obtained analogously to Example P5 using 4,4-dimethylpyrazolidine-N,N'-dicarboxylic acid di-tert-butyl ester.

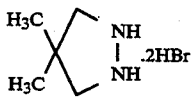

Example P 11

Preparation of
α-[2-chloro-4-fluoro-5-(4-methoxypyrazolidinylthiocarbonylamino)-phenylthio]-acetic acid methyl ester

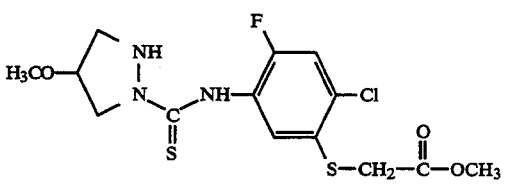

4.2 ml of triethylamine are added to a suspension of 2.65 g of 4-methoxypyrazolidine dihydrobromide in 50 ml of ethyl acetate and the reaction mixture is stirred for 10 minutes at 22° C. 2.35 g of 4-chloro-2-fluoro-5-methoxycarbonylmethyl-thiophenyl isothiocyanate are then added thereto and the reaction mixture is stirred overnight at 22° C. The organic phase is washed with water, dried and concentrated. The crystalline product, α-[2-choro-4-fluoro-5-(4-methoxypyrazolidinyl-thiocarbonylamino)-phenylthio]-acetic acid methyl ester, is obtained in a yield of 3.0 g; m.p. >90° C. (decomposition).

Example P12

Preparation of
8-(4-chloro-2-fluoro-5-methoxycarbonylmethylthiophenyl-imino)-3-methoxy-7-thia-1,5-diazabicyclo[3.3.-0]octan-6-one

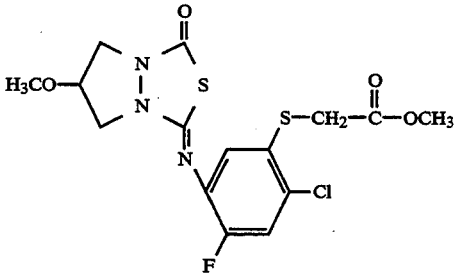

At 0°-5° C., 4.2 ml of phosgene solution in toluene (20%) are added to a solution of 2.8 g of α-[2-chloro-4-fluoro-5-(4-methoxypyrazolidinyl-thiocarbonylamino)-phenylthio]-acetic acid methyl ester in 20 ml of toluene. After stirring for 2 hours at 22° C., the organic phase is washed with water, dried and concentrated. The product is purified by means of column chromatography to yield 2.21 g of the desired product, 8-(4-chloro-2-fluoro-5-methoxy-carbonylmethylthio-phenylimino)-3-methoxy-7-thia-1,5-diazabicyclo[3.3.0]octan-6-one, in the form of a yellow oil.

Example P 13

Preparation of
4-hydroxy-N-[(2-fluoro-4-chloro-5-isopropoxy)-phenyl]pyrazolidine-2-thioamide

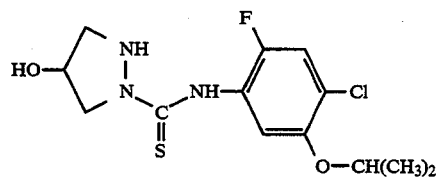

At 0°-5° C., 2.8 ml of triethylamine are added dropwise to a suspension of 2.0 g of 4-hydroxy-pyrazolidine dihydrobromide in 25 ml of tetrahydrofuran. After stirring for 10 minutes at 22° C., 2.0 g of 4-chloro-2-fluoro-5-isopropoxy-phenyl isothiocyanate in 5 ml of tetrahydrofuran are added dropwise thereto and the reaction mixture is stirred for 3 hours. The reaction mixture is concentrated; ethyl acetate is added and the organic phase is washed with water, dried and concentrated. The product is purified by crystallisation from petroleum ether. The desired product, 4-hydroxy-N-[(2-fluoro-4-chloro-5-isopropoxy)phenyl]-pyrazolidine-2-thioamide, is obtained in the form of white crystals in a yield of 2.2 g; m.p. 151°-153° C. (decomposition).

Example P 14

Preparation of
8-(4-chloro-2-fluoro-5-isopropoxyphenylimino)-3-hydroxy-7-thia-1,5-diazabicyclo3.3.0]octan-6-one

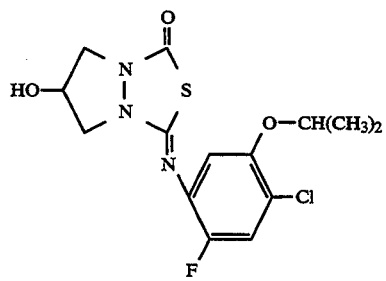

At 0°-5° C., 3.4 ml of phosgene dissolved in toluene (20 %) are added dropwise to a solution of 2.1 g of 4-chloro-2-fluoro-5-isopropoxy-N-(4-hydroxypyrazolidinyl-thiocarbonyl)-aniline in 50 ml of dichloromethane. After stirring for 1 hour at 22° C, the reaction mixture is concentrated and then ethyl acetate is added thereto. The organic phase is washed with water, dried and concentrated and the resulting residue is purified by means of column chromatography to yield 1.95 g of the desired product, 8-(4-chloro-2-fluoro-5-isopropoxyphenylimino)-3-hydroxy-7-thia- 1,5-diazabicyclo[3.3.0]octan-6-one, in the form of a resin.

The compounds of formula I listed in the following Tables 1 to 15 are prepared in analogous manner.

TABLE 1

Compounds of formula Ic:

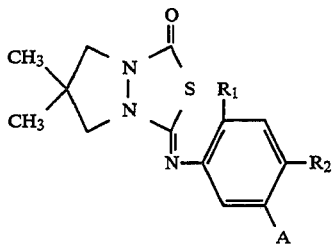

| Comp. No. | R₁ | R₂ | A | phys. data |
|---|---|---|---|---|
| 1.001 | F | Cl | —H | |
| 1.002 | F | Cl | —CN | |
| 1.003 | F | Cl | —NO₂ | |
| 1.004 | F | Cl | —COOH | |
| 1.005 | F | Cl | —COOCH₃ | |
| 1.006 | F | Cl | —COOC₂H₅ | |
| 1.007 | F | Cl | —COOC₃H₇ | |
| 1.008 | F | Cl | —COOCH(CH₃)₂ | |
| 1.009 | F | Cl | —COOC₄H₉ | |
| 1.010 | F | Cl | —COOCH(CH₃)—CH₂—CH₃ | |
| 1.011 | F | Cl | —COOCH₂—CH₂—CH(CH₃)₂ | |
| 1.012 | F | Cl | —COOC₅H₁₁ | |
| 1.013 | F | Cl | —COOCH₂—CH₂—O—CH₃ | |
| 1.014 | F | Cl | —COOCH₂—CH₂—O—C₂H₅ | |
| 1.015 | F | Cl | —COOCH(CH₃)—CH₂—OCH₃ | |
| 1.016 | F | Cl | —COOCH₂—CH₂—S—CH₃ | |
| 1.017 | F | Cl | —COOCH(CH₃)—CH₂—S—CH₃ | |
| 1.018 | F | Cl | —COOCH(CH₃)—CH₂—S—C₂H₅ | |
| 1.019 | F | Cl | —COOCH(CH₃)—CH₂—S—C₃H₇ | |
| 1.020 | F | Cl | —COOCH(CH₃)—CH₂—S—CH(CH₃)₂ | |
| 1.021 | F | Cl | —COOCH(CH₃)—CH₂—S—C₄H₉ | |
| 1.022 | F | Cl | —COOCH(CH₃)—CH₂—S—C₅H₁₁ | |
| 1.023 | F | Cl | —COOCH(CH₃)—CH₂—N(CH₃)₂ | |
| 1.024 | F | Cl | —COOCH(CH₃)—CH₂—N(C₂H₅)₂ | |
| 1.025 | F | Cl | —CONH₂ | |
| 1.026 | F | Cl | —CONH—CH₃ | |
| 1.027 | F | Cl | —CON(CH₃)₂ | |
| 1.028 | F | Cl | —CON(CH₃)(C₄H₉) | |

TABLE 1-continued

Compounds of formula Ic:

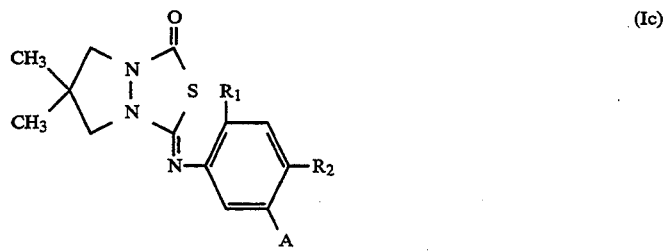

| Comp. No. | R₁ | R₂ | A | phys. data |
|---|---|---|---|---|
| 1.029 | F | Cl | —CON(CH₂—CH₂—OH)₂ | |
| 1.030 | F | Cl | —CONH—CH₂—CH=CH₂ | |
| 1.031 | F | Cl | —CON(CH₂—CH=CH₂)₂ | |
| 1.032 | F | Cl | —CON(pyrrolidine) | |
| 1.033 | F | Cl | —CON(piperidine) | |
| 1.034 | F | Cl | —CON(morpholine) | |
| 1.035 | F | Cl | —CON(thiomorpholine) | |
| 1.036 | F | Cl | —CON(N-methylpiperazine) | |
| 1.037 | F | Cl | —COON=C(CH₃)₂ | |
| 1.038 | F | Cl | —COOCH₂—CH₂—Cl | |
| 1.039 | F | Cl | —COOCH₂—CN | |
| 1.040 | F | Cl | —COOCH(CN)CH₃ | |
| 1.041 | F | Cl | —COOCH₂—CH=CH₂ | |
| 1.042 | F | Cl | —COOCH₂—CH=CHCl | |
| 1.043 | F | Cl | —COOCH₂—C(Cl)=CH₂ | |
| 1.044 | F | Cl | —COOCH₂—C≡CH | |
| 1.045 | F | Cl | —COO—CH(CH₃)—C≡CH | |

TABLE 1-continued

Compounds of formula Ic:

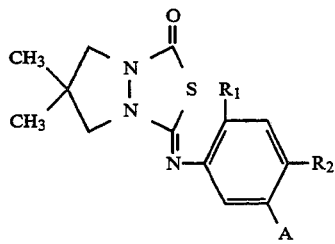

(Ic)

| Comp. No. | R₁ | R₂ | A | phys. data |
|---|---|---|---|---|
| 1.046 | F | Cl | —COO—⟨cyclopentyl⟩ | |
| 1.047 | F | Cl | —COO—⟨cyclohexyl⟩ | |
| 1.048 | F | Cl | —COOCH₂—⟨cyclopentyl⟩ | |
| 1.049 | F | Cl | —COOCH(CH₃)—cyclopropyl | |
| 1.050 | F | Cl | —COOCH₂—C₆H₅ | |
| 1.051 | F | Cl | —COOCH₂—(2-Cl-C₆H₄) | |
| 1.052 | F | Cl | —COOCH₂—(4-CH₃-C₆H₄) | |
| 1.053 | F | Cl | —COSCH₃ | |
| 1.054 | F | Cl | —COSC₂H₅ | |
| 1.055 | F | Cl | —COSC₃H₇ | |
| 1.056 | F | Cl | —COS—CH₂—CH=CH₂ | |
| 1.057 | F | Cl | —COS—CH₂—COOCH₃ | |
| 1.058 | F | Cl | —COS—CH₂—COOC₂H₅ | |
| 1.059 | F | Cl | —COS—CH₂—COOC₅H₁₁ | |
| 1.060 | F | Cl | —COS—CH(CH₃)—COOCH₃ | |
| 1.061 | F | Cl | —COS—CH(CH₃)—COOC₂H₅ | |
| 1.062 | F | Cl | —COS—CH(CH₃)—COOC₃H₇ | |

TABLE 1-continued

Compounds of formula Ic:

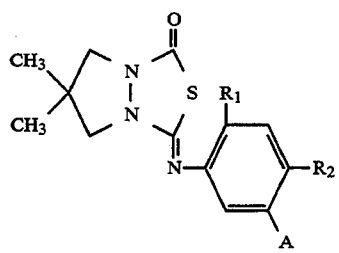

(Ic)

| Comp. No. | R₁ | R₂ | A | phys. data |
|---|---|---|---|---|
| 1.063 | F | Cl | —COS—CH₂—CH₂—COOCH₃ | |
| 1.064 | F | Cl | —COS—CH₂—COOCH₂—CH₂—O—CH₃ | |
| 1.065 | F | Cl | —COOCH₂—COOCH₃ | |
| 1.066 | F | Cl | —COOCH(CH₃)—COOCH₃ | |
| 1.067 | F | Cl | —COOCH₂—COOC₅H₁₁ | |
| 1.068 | F | Cl | —COOCH₂—CH₂—Si(CH₃)₃ | |
| 1.069 | F | Cl | —COONa | |
| 1.070 | F | Cl | —COOCH₂—CH₂—O—N=C(CH₃)₂ | |
| 1.071 | F | Cl | —OH | |
| 1.072 | F | Cl | —OCH₃ | |
| 1.073 | F | Cl | —OC₂H₅ | |
| 1.074 | F | Cl | —OC₃H₇ | |
| 1.075 | F | Cl | —OCH(CH₃)₂ | m.p. 76–77° C. |
| 1.076 | F | Cl | —OC₄H₉ | |
| 1.077 | F | Cl | —OCH(CH₃)—C₂H₅ | |
| 1.078 | F | Cl | —O—CH₂—CH(CH₃)₂ | |
| 1.079 | F | Cl | —OCH₂CH=CH₂ | |
| 1.080 | F | Cl | —OCH₂—C(Cl)=CH₂ | |
| 1.081 | F | Cl | —OCH₂CH=CHCl | |
| 1.082 | F | Cl | —OCH₂C≡CH | |
| 1.083 | F | Cl | —OCH(CH₃)—C≡CH | |
| 1.084 | F | Cl | —OCH₂—COOCH₃ | |
| 1.085 | F | Cl | —O—CH₂—COOC₅H₁₁ | |
| 1.086 | F | Cl | —O—CH(CH₃)—COOCH₃ | |
| 1.087 | F | Cl | —O—CH₂—COOC₂H₅ | |

TABLE 1-continued

Compounds of formula Ic:

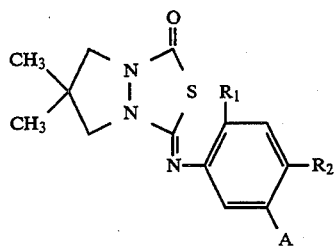

(Ic)

| Comp. No. | $R_1$ | $R_2$ | A | phys. data |
|---|---|---|---|---|
| 1.088 | F | Cl | $-O-CH(CH_3)-COOC_2H_5$ | |
| 1.089 | F | Cl | $-O-CH_2-CH_2-O-CH_3$ | |
| 1.090 | F | Cl | $-O-CH(CH_3)-CH_2-S-CH_3$ | |
| 1.091 | F | Cl | $-O-CH(CH_3)-CH_2-S-C_2H_5$ | |
| 1.092 | F | Cl | $-O-CH(CH_3)-CH_2-S-C_3H_7$ | |
| 1.093 | F | Cl | $-O-CH_2-CH_2-Cl$ | |
| 1.094 | F | Cl | $-O-CH_2-CN$ | |
| 1.095 | F | Cl | $-O-CH(CH_3)-CN$ | |
| 1.096 | F | Cl | $-S-CH_3$ | |
| 1.097 | F | Cl | $-S-C_2H_5$ | |
| 1.098 | F | Cl | $-S-C_3H_7$ | |
| 1.099 | F | Cl | $-S-CH(CH_3)_2$ | |
| 1.100 | F | Cl | $-S-CH_2-CH=CH_2$ | |
| 1.101 | F | Cl | $-S-CH_2-C(Cl)=CH_2$ | |
| 1.102 | F | Cl | $-S-CH_2-CH=CHCl$ | |
| 1.103 | F | Cl | $-S-CH_2-C\equiv CH$ | |
| 1.104 | F | Cl | $-S-CH(CH_3)-C\equiv CH$ | |
| 1.105 | F | Cl | $-S-CH_2-COOCH_3$ | |
| 1.106 | F | Cl | $-S-CH_2-COOC_2H_5$ | |
| 1.107 | F | Cl | $-S-CH_2-COOC_5H_{11}$ | |
| 1.108 | F | Cl | $-S-CH(CH_3)-COOCH_3$ | |
| 1.109 | F | Cl | $-S-CH(CH_3)-COOC_2H_5$ | |
| 1.110 | F | Cl | $-S-CH_2-COOCH_2-CH_2-O-CH_3$ | |

TABLE 1-continued
Compounds of formula Ic:
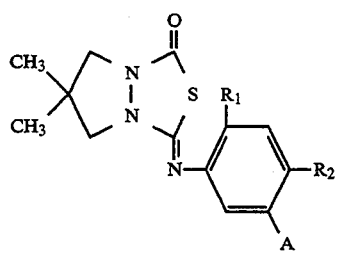
| Comp. No. | $R_1$ | $R_2$ | A | phys. data |
|---|---|---|---|---|
| 1.111 | F | Cl | —O—CH$_2$—C$_6$H$_5$ | |
| 1.112 | F | Cl | —S—CH$_2$—C$_6$H$_5$ | |
| 1.113 | F | Cl | —C(=N—O—CH$_3$)—CN | |
| 1.114 | F | Cl | —C(=N—O—CH$_2$—COOCH$_3$)—CN | |
| 1.115 | F | Cl | —C(=N—O—CH$_2$—C≡CH)—CN | |
| 1.116 | F | Cl | —C(=N—O—CH$_3$)—CH$_3$ | |
| 1.117 | F | Cl | —C(=N—O—CH$_2$—C≡CH)—CH$_3$ | |
| 1.118 | F | Cl | —C(=N—O—CH$_3$)—CH$_2$—O—CH$_3$ | |
| 1.119 | F | Cl | —C(CH$_3$)(O—CH$_3$)$_2$ | |
| 1.120 | F | Cl | —C(CH$_3$)(O—C$_2$H$_5$)$_2$ | |
| 1.121 | F | Cl | —C(CH$_3$)(—O—CH$_2$—O—) (1,3-dioxolane) | |

TABLE 1-continued

Compounds of formula Ic:

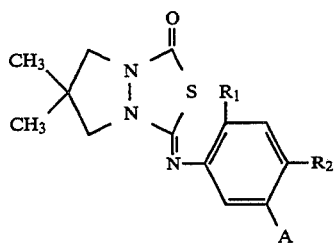

(Ic)

| Comp. No. | R₁ | R₂ | A | phys. data |
|---|---|---|---|---|
| 1.122 | F | Cl | -C(O-CH(CH₃))₂ (dioxolane with two CH₃ on one carbon and CH₃ on the other; structure: -C with two O linking to CH(CH₃)-C(CH₃)₂) | |
| 1.123 | F | Cl | -S-△-COOCH₃ | |
| 1.124 | F | Cl | -S-△-COOC₂H₅ | |
| 1.125 | F | Cl | -S-△-COOC₃H₇ | |
| 1.126 | F | Cl | -S-△-COOCH(CH₃)₂ | |
| 1.127 | F | Cl | -S-△-COO—CH₂—CH₂—Cl | |
| 1.128 | F | Cl | -S-△-COOC₅H₁₁ | |
| 1.129 | F | Cl | -S-△-COOCH₂—CH₂—O—CH₃ | |
| 1.130 | F | Cl | -S-△-COOCH(CH₃)—CH₂—S—CH₃ | |
| 1.131 | F | Cl | -S-△-COOCH(CH₃)—N(CH₃)₂ | |
| 1.132 | F | Cl | -S-△-COO-cyclopentyl | |
| 1.133 | F | Cl | -S-△-COO-cyclohexyl | |
| 1.134 | F | Cl | -S-△-COO—CH₂—CH₂—CH=CH₂ | |

TABLE 1-continued
Compounds of formula Ic:
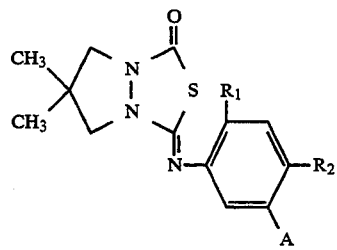
(Ic)
| Comp. No. | R₁ | R₂ | A | phys. data |
|---|---|---|---|---|
| 1.135 | F | Cl | —S—△—COO—CH₂—C(Cl)=CH₂ | |
| 1.136 | F | Cl | —S—△—COO—CH₂—C≡CH | |
| 1.137 | F | Cl | —S—△—COOH | |
| 1.138 | F | Cl | —S—△—CONH₂ | |
| 1.139 | F | Cl | —S—△—CONH—CH₃ | |
| 1.140 | F | Cl | —S—△(CH₃)—COOC₂H₅ | |
| 1.141 | F | Cl | —S—△(C₂H₅)—COOC₂H₅ | |
| 1.142 | F | Cl | —S—△(F)—COOCH₃ | |
| 1.143 | F | Cl | —S—△(F)—COOC₂H₅ | |
| 1.144 | F | Cl | —S—△—COO—CH(CH₃)₂ | |
| 1.145 | F | Cl | —S—△—COO—cyclopentyl | |
| 1.146 | F | Cl | —NH—SO₂—CH₃ | |
| 1.147 | F | Cl | —NH—SO₂—C₂H₅ | |
| 1.148 | F | Cl | —NH—SO₂—Cl | |
| 1.149 | F | Cl | —NH—SO₂—△ | |

TABLE 1-continued

Compounds of formula Ic:

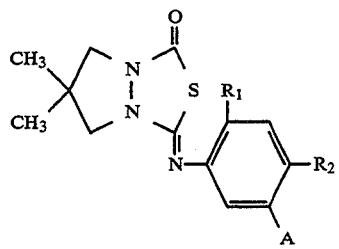

(Ic)

| Comp. No. | R₁ | R₂ | A | phys. data |
|---|---|---|---|---|
| 1.150 | F | Cl | $-O-P(=O)(OC_2H_5)(OC_2H_5)$ | |
| 1.151 | H | Cl | —COOH | m.p. >230° C. (decomp.) |
| 1.152 | H | Cl | —COOCH₃ | m.p. 104–106° C. |
| 1.153 | H | Cl | —COO—CH(CH₃)₂ | m.p. 90–91° C. |
| 1.154 | H | Cl | —COO—C₅H₁₁ | |
| 1.155 | H | Cl | —COO—CH₂—CH₂—O—CH₃ | |
| 1.156 | H | Cl | —COOCH₂—S—CH₃ | |
| 1.157 | H | Cl | —COOCH(CH₃)—CH₂—S—CH₃ | |
| 1.158 | H | Cl | —COO—CH(CH₃)—CH₂—N(CH₃)₂ | |
| 1.159 | H | Cl | —CO—N(CH₃)₂ | |
| 1.160 | H | Cl | —CO—N(morpholino) | |
| 1.161 | H | Cl | —COON=C(CH₃)₂ | |
| 1.162 | H | Cl | —COOCH₂—CH₂—O—N=C(CH₃)₂ | |
| 1.163 | H | Cl | —COO—cyclohexyl | |
| 1.164 | H | Cl | —CH(CH₃)—cyclopropyl | |
| 1.165 | H | Cl | —S—C₃H₇ | |
| 1.166 | H | Cl | —COOCH₂—COOCH₃ | |
| 1.167 | H | Cl | —COOCH(CH₃)—COOCH₃ | |
| 1.168 | H | Cl | —COS—CH₂—COOCH₃ | |
| 1.169 | H | Cl | —COS—CH(CH₃)—COOCH₃ | |
| 1.170 | H | Cl | —OH | |
| 1.171 | H | Cl | —OCH₃ | |

TABLE 1-continued

Compounds of formula Ic:

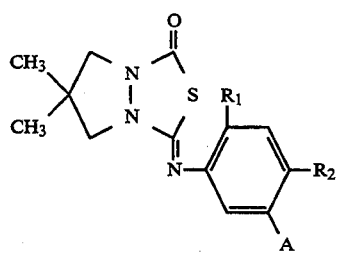

(Ic)

| Comp. No. | R₁ | R₂ | A | phys. data |
|---|---|---|---|---|
| 1.172 | H | Cl | —O—C₂H₅ | |
| 1.173 | H | Cl | —O—CH(CH₃)₂ | |
| 1.174 | H | Cl | —O—CH₂—C≡CH | |
| 1.175 | H | Cl | —O—CH₂—CH=CHCl | |
| 1.176 | H | Cl | —O—CH₂—C(Cl)=CH₂ | |
| 1.177 | H | Cl | —O—CH(CH₃)—C≡CH | |
| 1.178 | H | Cl | —O—CH₂—COOCH₃ | |
| 1.179 | H | Cl | —O—CH₂—COOC₂H₅ | |
| 1.180 | H | Cl | —O—CH(CH₃)—COOCH₃ | |
| 1.181 | H | Cl | —SH | |
| 1.182 | H | Cl | —SCH₃ | |
| 1.183 | H | Cl | —SC₂H₅ | |
| 1.184 | H | Cl | —S—CH(CH₃)₂ | |
| 1.185 | H | Cl | —S—CH₂—COOCH₃ | |
| 1.186 | H | Cl | —S—CH(CH₃)—COOCH₃ | |
| 1.187 | H | Cl | —S—CH₂—COOC₂H₅ | |
| 1.188 | H | Cl | —C(=N—OCH₃)—CN | |
| 1.189 | H | Cl | —C(OCH(CH₃))₂ (cyclic acetal with two CH₃) | |
| 1.190 | H | Cl | —S—(cyclopropyl)—COOC₂H₅ | |
| 1.191 | H | Cl | —S—(cyclopropyl)—COOH | |
| 1.192 | H | Cl | —S—(cyclopropyl)—COO—CH(CH₃)₂ | |

TABLE 1-continued
Compounds of formula Ic:
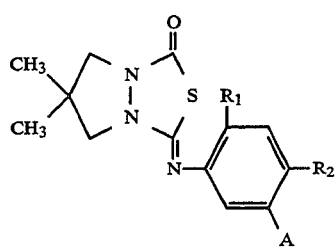
(Ic)
| Comp. No. | R₁ | R₂ | A | phys. data |
|---|---|---|---|---|
| 1.193 | H | Cl | —S—◁—COOC₂H₅ with CH₃ | |
| 1.194 | H | Cl | —S—◁—COOC₂H₅ with F | |
| 1.195 | H | Cl | —S—◁—COOC₂H₅ with CF₃ | |
| 1.196 | H | Cl | —S—◁—COO—CH(CH₃)₂ with CF₃ | |
| 1.197 | H | Cl | —S—◁—COOH | |
| 1.198 | H | Cl | —S—◁—COOH with CF₃ | |
| 1.199 | H | Cl | —S—◁—COOC₅H₁₁ with CF₃ | |
| 1.200 | H | Cl | —S—◁—COOC₂H₅ with C₂H₅ | |
| 1.201 | H | Cl | —S—◁—COOC₂H₅ with CH(CH₃)CH₃ | |
| 1.202 | H | Cl | —NH—SO₂—C₂H₅ | |
| 1.203 | H | Cl | —NH—SO₂—CH₂—Cl | |
| 1.204 | F | CN | —COOH | |
| 1.205 | F | CN | —COO—CH(CH₃)₂ | |

TABLE 1-continued

Compounds of formula Ic:

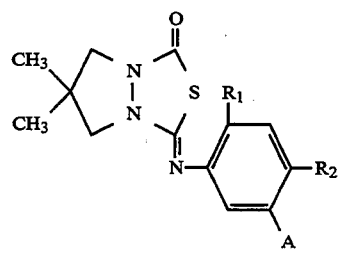

(Ic)

| Comp. No. | $R_1$ | $R_2$ | A | phys. data |
|---|---|---|---|---|
| 1.206 | F | CN | —O—CH(CH$_3$)$_2$ | |
| 1.207 | F | CN | —O—CH$_2$—C≡CH | |
| 1.208 | F | CN | —O—CH(CH$_3$)—C≡CH | |
| 1.209 | F | CN | —S—CH$_2$—COOCH$_3$ | |
| 1.210 | F | CN | —S—CH(CH$_3$)—COOCH$_3$ | |
| 1.211 | F | CN | —O—CH$_2$—COOCH$_3$ | |
| 1.212 | F | CN | —O—CH$_2$—COOC$_5$H$_{11}$ | |
| 1.213 | F | CN | —O—CH(CH$_3$)—COOC$_2$H$_5$ | |
| 1.214 | F | CN | —S—(cyclopropyl)—COOCH$_3$ | |
| 1.215 | F | CN | —S—(cyclopropyl)—COOC$_2$H$_5$ | |
| 1.216 | F | CN | —S—(cyclopropyl(F))—COOC$_2$H$_5$ | |
| 1.217 | F | CN | —S—(cyclopropyl)—COOH | |
| 1.218 | F | CN | —S—(cyclopropyl(F))—COOH | |
| 1.219 | F | CN | —S—(cyclopropyl(CF$_3$))—COOH | |
| 1.220 | F | CN | —S—(cyclopropyl)—COOC$_2$H$_5$ | |
| 1.221 | F | Br | —COOH | |
| 1.222 | F | Br | —COO—CH(CH$_3$)$_2$ | |
| 1.223 | F | Br | —OH | |
| 1.224 | F | Br | —O—CH(CH$_3$)$_2$ | |
| 1.225 | F | Br | —O—CH$_2$—C≡CH | |
| 1.226 | F | Br | —O—CH(CH$_3$)—C≡CH | |
| 1.227 | F | Br | —O—CH$_2$COOCH$_3$ | |

TABLE 1-continued
Compounds of formula Ic:

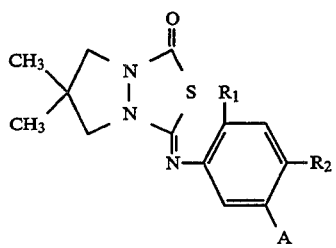

(Ic)

| Comp. No. | R₁ | R₂ | A | phys. data |
|---|---|---|---|---|
| 1.228 | F | Br | —O—CH₂—COOC₅H₁₁ | |
| 1.229 | F | Br | —S—CH₂—COOCH₃ | |
| 1.230 | F | Br | —S—⬡—COOC₂H₅ (cyclopropyl) | |
| 1.231 | F | Br | —S—⬡—COOH (F-cyclopropyl) | |
| 1.232 | F | Br | —S—⬡—COOC₂H₅ (F-cyclopropyl) | |
| 1.233 | F | Cl | —S—CH₂COOH | m.p. >120° C. (decomp.) |

TABLE 2
Compounds of formula Id:

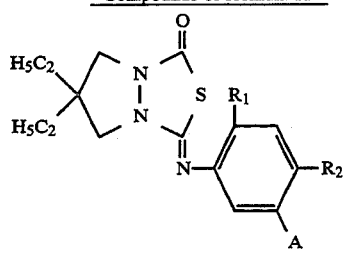

(Id)

| Comp. No. | R₁ | R₂ | A | phys. data |
|---|---|---|---|---|
| 2.001 | F | Cl | —H | |
| 2.002 | F | Cl | —CN | |
| 2.003 | F | Cl | —NO₂ | |
| 2.004 | F | Cl | —COOH | |
| 2.005 | F | Cl | —COOCH₃ | |
| 2.006 | F | Cl | —COOC₂H₅ | |
| 2.007 | F | Cl | —COOC₃H₇ | |
| 2.008 | F | Cl | —COOCH(CH₃)₂ | |
| 2.009 | F | Cl | —COOC₄H₉ | |
| 2.010 | F | Cl | —COOCH(CH₃)—CH₂—CH₃ | |
| 2.011 | F | Cl | —COOCH₂—CH₂—CH(CH₃)₂ | |
| 2.012 | F | Cl | —COOC₅H₁₁ | |
| 2.013 | F | Cl | —COOCH₂—CH₂—O—CH₃ | |
| 2.014 | F | Cl | —COOCH₂—CH₂—O—C₂H₅ | |
| 2.015 | F | Cl | —COOCH(CH₃)—CH₂—OCH₃ | |
| 2.016 | F | Cl | —COOCH₂—CH₂—S—CH₃ | |
| 2.017 | F | Cl | —COOCH(CH₃)—CH₂—S—CH₃ | |

TABLE 2-continued

Compounds of formula Id:

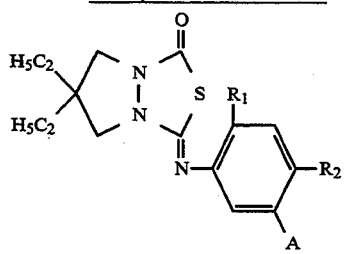

(Id)

| Comp. No. | R₁ | R₂ | A | phys. data |
|---|---|---|---|---|
| 2.018 | F | Cl | —COOCH(CH₃)—CH₂—S—C₂H₅ | |
| 2.019 | F | Cl | —COOCH(CH₃)—CH₂—S—C₃H₇ | |
| 2.020 | F | Cl | —COOCH(CH₃)—CH₂—S—CH(CH₃)₂ | |
| 2.021 | F | Cl | —COOCH(CH₃)—CH₂—S—C₄H₉ | |
| 2.022 | F | Cl | —COOCH(CH₃)—CH₂—S—C₅H₁₁ | |
| 2.023 | F | Cl | —COOCH(CH₃)—CH₂—N(CH₃)₂ | |
| 2.024 | F | Cl | —COOCH(CH₃)—CH₂—N(C₂H₅)₂ | |
| 2.025 | F | Cl | —CONH₂ | |
| 2.026 | F | Cl | —CONH—CH₃ | |
| 2.027 | F | Cl | —CON(CH₃)₂ | |
| 2.028 | F | Cl | —CON(CH₃)(C₄H₉) | |
| 2.029 | F | Cl | —CON(CH₂—CH₂—OH)₂ | |
| 2.030 | F | Cl | —CONH—CH₂—CH=CH₂ | |
| 2.031 | F | Cl | —CON(CH₂—CH=CH₂)₂ | |
| 2.032 | F | Cl | —CON(pyrrolidinyl) | |
| 2.033 | F | Cl | —CON(piperidinyl) | |
| 2.034 | F | Cl | —CON(morpholinyl) | |

TABLE 2-continued

Compounds of formula Id:

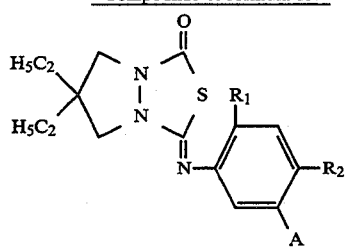

(Id)

| Comp. No. | R₁ | R₂ | A | phys. data |
|---|---|---|---|---|
| 2.035 | F | Cl | —CON⟨S⟩ (thiomorpholine) | |
| 2.036 | F | Cl | —CON⟨N—CH₃⟩ (N-methylpiperazine) | |
| 2.037 | F | Cl | —COON=C(CH₃)(CH₃) | |
| 2.038 | F | Cl | —COOCH₂—CH₂—Cl | |
| 2.039 | F | Cl | —COOCH₂—CN | |
| 2.040 | F | Cl | —COOCH(CN)(CH₃) | |
| 2.041 | F | Cl | —COOCH₂—CH=CH₂ | |
| 2.042 | F | Cl | —COOCH₂—CH=CHCl | |
| 2.043 | F | Cl | —COOCH₂—C(Cl)=CH₂ | |
| 2.044 | F | Cl | —COOCH₂—C≡CH | |
| 2.045 | F | Cl | —COO—CH(CH₃)—C≡CH | |
| 2.046 | F | Cl | —COO-cyclopentyl | |
| 2.047 | F | Cl | —COO-cyclohexyl | |
| 2.048 | F | Cl | —COOCH₂-cyclopentyl | |
| 2.049 | F | Cl | —COOCH(CH₃)-cyclopropyl | |

TABLE 2-continued

Compounds of formula Id:

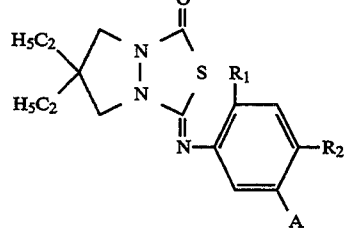

(Id)

| Comp. No. | $R_1$ | $R_2$ | A | phys. data |
|---|---|---|---|---|
| 2.050 | F | Cl | —COOCH$_2$—C$_6$H$_5$ | |
| 2.051 | F | Cl | —COOCH$_2$—(2-Cl-C$_6$H$_4$) | |
| 2.052 | F | Cl | —COOCH$_2$—(4-CH$_3$-C$_6$H$_4$) | |
| 2.053 | F | Cl | —COSCH$_3$ | |
| 2.054 | F | Cl | —COSC$_2$H$_5$ | |
| 2.055 | F | Cl | —COSC$_3$H$_7$ | |
| 2.056 | F | Cl | —COS—CH$_2$—CH=CH$_2$ | |
| 2.057 | F | Cl | —COS—CH$_2$—COOCH$_3$ | |
| 2.058 | F | Cl | —COS—CH$_2$—COOC$_2$H$_5$ | |
| 2.059 | F | Cl | —COS—CH$_2$—COOC$_5$H$_{11}$ | |
| 2.060 | F | Cl | —COS—CH(CH$_3$)—COOCH$_3$ | |
| 2.061 | F | Cl | —COS—CH(CH$_3$)—COOC$_2$H$_5$ | |
| 2.062 | F | Cl | —COS—CH(CH$_3$)—COOC$_3$H$_7$ | |
| 2.063 | F | Cl | —COS—CH$_2$—CH$_2$—COOCH$_3$ | |
| 2.064 | F | Cl | —COS—CH$_2$—COOCH$_2$—CH$_2$—O—CH$_3$ | |
| 2.065 | F | Cl | —COOCH$_2$—COOCH$_3$ | |
| 2.066 | F | Cl | —COOCH(CH$_3$)—COOCH$_3$ | |
| 2.067 | F | Cl | —COOCH$_2$—COOC$_5$H$_{11}$ | |
| 2.068 | F | Cl | —COOCH$_2$—CH$_2$Si(CH$_3$)$_3$ | |
| 2.069 | F | Cl | —COONa | |
| 2.070 | F | Cl | —COOCH$_2$—CH$_2$—O—N=C(CH$_3$)$_2$ | |
| 2.071 | F | Cl | —OH | |
| 2.072 | F | Cl | —OCH$_3$ | |
| 2.073 | F | Cl | —OC$_2$H$_5$ | |
| 2.074 | F | Cl | —OC$_3$H$_7$ | |

TABLE 2-continued

Compounds of formula Id:

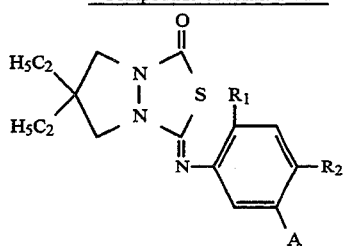

(Id)

| Comp. No. | R₁ | R₂ | A | phys. data |
|---|---|---|---|---|
| 2.075 | F | Cl | —OCH(CH₃)₂ | |
| 2.076 | F | Cl | —OC₄H₉ | |
| 2.077 | F | Cl | —OCH(CH₃)—C₂H₅ | |
| 2.078 | F | Cl | —O—CH₂—CH(CH₃)₂ | |
| 2.079 | F | Cl | —OCH₂CH=CH₂ | |
| 2.080 | F | Cl | —OCH₂—C(Cl)=CH₂ | |
| 2.081 | F | Cl | —OCH₂CH=CHCl | |
| 2.082 | F | Cl | —OCH₂C≡CH | |
| 2.083 | F | Cl | —OCH(CH₃)—C≡CH | |
| 2.084 | F | Cl | —OCH₂—COOCH₃ | |
| 2.085 | F | Cl | —O—CH₂—COOC₅H₁₁ | |
| 2.086 | F | Cl | —O—CH(CH₃)—COOCH₃ | |
| 2.087 | F | Cl | —O—CH₂—COOC₂H₅ | |
| 2.088 | F | Cl | —O—CH(CH₃)—COOC₂H₅ | |
| 2.089 | F | Cl | O—CH₂—CH₂—O—CH₃ | |
| 2.090 | F | Cl | —O—CH(CH₃)—CH₂—S—CH₃ | |
| 2.091 | F | Cl | —O—CH(CH₃)—CH₂—S—C₂H₅ | |
| 2.092 | F | Cl | —O—CH(CH₃)—CH₂—S—C₃H₇ | |
| 2.093 | F | Cl | —O—CH₂—CH₂—Cl | |
| 2.094 | F | Cl | —O—CH₂—CN | |
| 2.095 | F | Cl | —O—CH(CH₃)—CN | |

TABLE 2-continued

Compounds of formula Id:

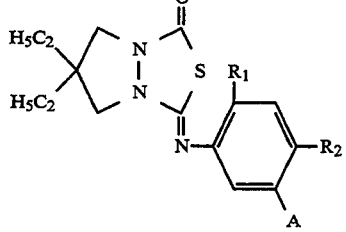

(Id)

| Comp. No. | R₁ | R₂ | A | phys. data |
|---|---|---|---|---|
| 2.096 | F | Cl | —S—CH₃ | |
| 2.097 | F | Cl | —S—C₂H₅ | |
| 2.098 | F | Cl | —S—C₃H₇ | |
| 2.099 | F | Cl | —S—CH(CH₃)CH₃ | |
| 2.100 | F | Cl | —S—CH₂—CH=CH₂ | |
| 2.101 | F | Cl | —S—CH₂—C(Cl)=CH₂ | |
| 2.102 | F | Cl | —S—CH₂—CH=CHCl | |
| 2.103 | F | Cl | —S—CH₂—C≡CH | |
| 2.104 | F | Cl | —S—CH(CH₃)—C≡CH | |
| 2.105 | F | Cl | —S—CH₂—COOCH₃ | |
| 2.106 | F | Cl | —S—CH₂—COOC₂H₅ | |
| 2.107 | F | Cl | —S—CH₂—COOC₅H₁₁ | |
| 2.108 | F | Cl | —S—CH(CH₃)—COOCH₃ | |
| 2.109 | F | Cl | —S—CH(CH₃)—COOC₂H₅ | |
| 2.110 | F | Cl | —S—CH₂—COOCH₂—CH₂—O—CH₃ | |
| 2.111 | F | Cl | —O—CH₂—C₆H₅ | |
| 2.112 | F | Cl | —S—CH₂—C₆H₅ | |
| 2.113 | F | Cl | —C(=N—O—CH₃)—CN | |
| 2.114 | F | Cl | —C(=N—O—CH₂—COOCH₃)—CN | |
| 2.115 | F | Cl | —C(=N—O—CH₂—C≡CH)—CN | |
| 2.116 | F | Cl | —C(=N—O—CH₃)—CH₃ | |

TABLE 2-continued

Compounds of formula Id:

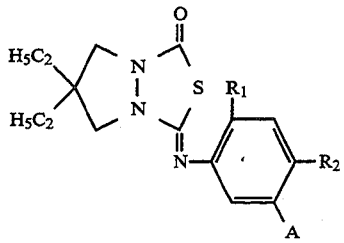

(Id)

| Comp. No. | R₁ | R₂ | A | phys. data |
|---|---|---|---|---|
| 2.117 | F | Cl | $-\underset{\substack{\parallel \\ N-O-CH_2-C\equiv CH}}{C}-CH_3$ | |
| 2.118 | F | Cl | $-\underset{\substack{\parallel \\ N-O-CH_3}}{N}-CH_2-O-CH_3$ | |
| 2.119 | F | Cl | $-\underset{CH_3}{\overset{O-CH_3}{\underset{\mid}{C}}}\!\!<\!\!^{O-CH_3}$ | |
| 2.120 | F | Cl | $-\underset{CH_3}{\overset{O-C_2H_5}{\underset{\mid}{C}}}\!\!<\!\!^{O-C_2H_5}$ | |
| 2.121 | F | Cl | $-\underset{CH_3}{\overset{O}{\underset{\mid}{C}}}\!\!<\!\!^{O}_{O}\!\!\rceil$ | |
| 2.122 | F | Cl | $-\underset{CH_3}{\overset{O-CH(CH_3)}{\underset{\mid}{C}}}\!\!<\!\!^{O-CH(CH_3)}$ | |
| 2.123 | F | Cl | —S—▷—COOCH₃ | |
| 2.124 | F | Cl | —S—▷—COOC₂H₅ | |
| 2.125 | F | Cl | —S—▷—COOC₃H₇ | |
| 2.126 | F | Cl | —S—▷—COOCH(CH₃)₂ | |
| 2.127 | F | Cl | —S—▷—COO—CH₂—CH₂—Cl | |
| 2.128 | F | Cl | —S—▷—COOC₅H₁₁ | |

TABLE 2-continued
Compounds of formula Id:
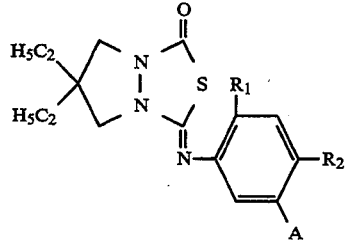
(Id)
| Comp. No. | R₁ | R₂ | A | phys. data |
|---|---|---|---|---|
| 2.129 | F | Cl | —S—△—COOCH₂—CH₂—O—CH₃ | |
| 2.130 | F | Cl | —S—△—COOCH(CH₃)—CH₂—S—CH₃ | |
| 2.131 | F | Cl | —S—△—COOCH(CH₃)—N(CH₃)₂ | |
| 2.132 | F | Cl | —S—△—COO-cyclopentyl | |
| 2.133 | F | Cl | —S—△—COO-cyclohexyl | |
| 2.134 | F | Cl | —S—△—COO—CH₂—CH₂—CH=CH₂ | |
| 2.135 | F | Cl | —S—△—COO—CH₂—C(Cl)=CH₂ | |
| 2.136 | F | Cl | —S—△—COO—CH₂—C≡CH | |
| 2.137 | F | Cl | —S—△—COOH | |
| 2.138 | F | Cl | —S—△—CONH₂ | |
| 2.139 | F | Cl | —S—△—CONH—CH₃ | |
| 2.140 | F | Cl | —S—△(CH₃)—COOC₂H₅ | |
| 2.141 | F | Cl | —S—△(C₂H₅)—COOC₂H₅ | |

TABLE 2-continued

Compounds of formula Id:

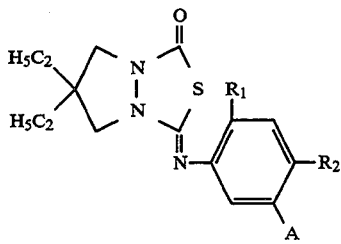

(Id)

| Comp. No. | R₁ | R₂ | A | phys. data |
|---|---|---|---|---|
| 2.142 | F | Cl | —S—$\triangle$(COOCH₃)(F) | |
| 2.143 | F | Cl | —S—$\triangle$(COOC₂H₅)(F) | |
| 2.144 | F | Cl | —S—$\triangle$—COO—CH(CH₃)₂ | |
| 2.145 | F | Cl | —S—$\triangle$—COO—cyclopentyl | |
| 2.146 | F | Cl | —NH—SO₂—CH₃ | |
| 2.147 | F | Cl | —NH—SO₂—C₂H₅ | |
| 2.148 | F | Cl | —NH—SO₂—Cl | |
| 2.149 | F | Cl | —NH—SO₂—$\triangle$ | |
| 2.150 | F | Cl | —O—P(=O)(OC₂H₅)(OC₂H₅) | |
| 2.151 | H | Cl | —COOH | |
| 2.152 | H | Cl | —COOCH₃ | |
| 2.153 | H | Cl | —COO—CH(CH₃)₂ | |
| 2.154 | H | Cl | —COO—C₅H₁₁ | |
| 2.155 | H | Cl | —COO—CH₂—CH₂—O—CH₃ | |
| 2.156 | H | Cl | —COOCH₂—S—CH₃ | |
| 2.157 | H | Cl | —COOCH(CH₃)—CH₂—S—CH₃ | |
| 2.158 | H | Cl | —COO—CH(CH₃)—CH₂—N(CH₃)(CH₃) | |
| 2.159 | H | Cl | —CO—N(CH₃)(CH₃) | |

TABLE 2-continued

Compounds of formula Id:

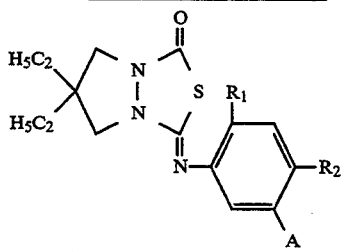

(Id)

| Comp. No. | R₁ | R₂ | A | phys. data |
|---|---|---|---|---|
| 2.160 | H | Cl | —CO—N(morpholino) | |
| 2.161 | H | Cl | —COON=C(CH₃)₂ | |
| 2.162 | H | Cl | —COOCH₂—CH₂—O—N=C(CH₃)₂ | |
| 2.163 | H | Cl | —COO-cyclohexyl | |
| 2.164 | H | Cl | —CH(CH₃)-cyclopropyl | |
| 2.165 | H | Cl | —S—C₃H₇ | |
| 2.166 | H | Cl | —COOCH₂—COOCH₃ | |
| 2.167 | H | Cl | —COOCH(CH₃)—COOCH₃ | |
| 2.168 | H | Cl | —COS—CH₂—COOCH₃ | |
| 2.169 | H | Cl | —COS—CH(CH₃)—COOCH₃ | |
| 2.170 | H | Cl | —OH | |
| 2.171 | H | Cl | —OCH₃ | |
| 2.172 | H | Cl | —O—C₂H₅ | |
| 2.173 | H | Cl | —O—CH(CH₃)₂ | |
| 2.174 | H | Cl | —O—CH₂—C≡CH | |
| 2.175 | H | Cl | —O—CH₂—CH=CHCl | |
| 2.176 | H | Cl | —O—CH₂—C(Cl)=CH₂ | |
| 2.177 | H | Cl | —O—CH(CH₃)—C≡CH | |
| 2.178 | H | Cl | —O—CH₂—COOCH₃ | |
| 2.179 | H | Cl | —O—CH₂—COOC₂H₅ | |
| 2.180 | H | Cl | —O—CH(CH₃)—COOCH₃ | |
| 2.181 | H | Cl | —SH | |
| 2.182 | H | Cl | —SCH₃ | |
| 2.183 | H | Cl | —SC₂H₅ | |

TABLE 2-continued

Compounds of formula Id:

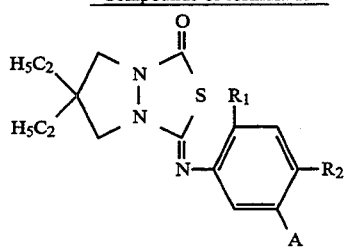

(Id)

| Comp. No. | R₁ | R₂ | A | phys. data |
|---|---|---|---|---|
| 2.184 | H | Cl | —S—CH(CH₃)₂ | |
| 2.185 | H | Cl | —S—CH₂—COOCH₃ | |
| 2.186 | H | Cl | —S—CH(CH₃)—COOCH₃ | |
| 2.187 | H | Cl | —S—CH₂—COOC₂H₅ | |
| 2.188 | H | Cl | —C(=N—OCH₃)—CN | |
| 2.189 | H | Cl | —C(O—CH(CH₃))₂ (dioxolane with two CH₃) | |
| 2.190 | H | Cl | —S—(cyclopropyl)—COOC₂H₅ | |
| 2.191 | H | Cl | —S—(cyclopropyl)—COOH | |
| 2.192 | H | Cl | —S—(cyclopropyl)—COO—CH(CH₃)₂ | |
| 2.193 | H | Cl | —S—(cyclopropyl, CH₃)—COOC₂H₅ | |
| 2.194 | H | Cl | —S—(cyclopropyl, F)—COOC₂H₅ | |
| 2.195 | H | Cl | —S—(cyclopropyl, CF₃)—COOC₂H₅ | |
| 2.196 | H | Cl | —S—(cyclopropyl, CF₃)—COO—CH(CH₃)₂ | |
| 2.197 | H | Cl | —S—(cyclopropyl)—COOH | |

TABLE 2-continued

Compounds of formula Id:

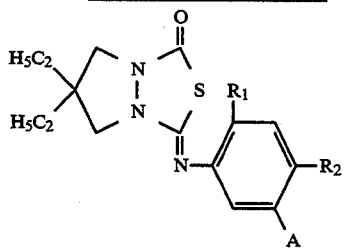

(Id)

| Comp. No. | R₁ | R₂ | A | phys. data |
|---|---|---|---|---|
| 2.198 | H | Cl | —S—△—COOH (CF₃) | |
| 2.199 | H | Cl | —S—△—COOC₅H₁₁ (CH₃) | |
| 2.200 | H | Cl | —S—△—COOC₂H₅ (C₂H₅) | |
| 2.201 | H | Cl | —S—△—COOC₂H₅ (CH(CH₃)₂) | |
| 2.202 | H | Cl | —NH—SO₂—C₂H₅ | |
| 2.203 | H | Cl | —NH—SO₂—CH₂—Cl | |
| 2.204 | F | CN | —COOH | |
| 2.205 | F | CN | —COO—CH(CH₃)₂ | |
| 2.206 | F | CN | —O—CH(CH₃)₂ | |
| 2.207 | F | CN | —O—CH₂—C≡CH | |
| 2.208 | F | CN | —O—CH(CH₃)—C≡CH | |
| 2.209 | F | CN | —S—CH₂—COOCH₃ | |
| 2.210 | F | CN | —S—CH(CH₃)—COOCH₃ | |
| 2.211 | F | CN | —O—CH₂—COOCH₃ | |
| 2.212 | F | CN | —O—CH₂—COOC₅H₁₁ | |
| 2.213 | F | CN | —O—CH(CH₃)—COOC₂H₅ | |
| 2.214 | F | CN | —S—△—COOCH₃ | |
| 2.215 | F | CN | —S—△—COOC₂H₅ | |
| 2.216 | F | CN | —S—△—COOC₂H₅ (F) | |
| 2.217 | F | CN | —S—△—COOH | |

TABLE 2-continued
Compounds of formula Id:
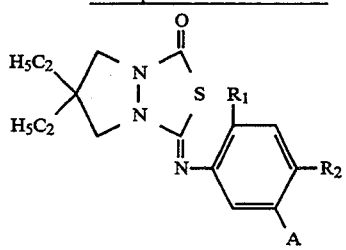
(Id)
| Comp. No. | R₁ | R₂ | A | phys. data |
|---|---|---|---|---|
| 2.218 | F | CN | —S—△—COOH (F) | |
| 2.219 | F | CN | —S—△—COOH (CF₃) | |
| 2.220 | F | CN | —S—△—COOC₂H₅ | |
| 2.221 | F | Br | —COOH | |
| 2.222 | F | Br | —COO—CH(CH₃)₂ | |
| 2.223 | F | Br | —OH | |
| 2.224 | F | Br | —O—CH(CH₃)₂ | |
| 2.225 | F | Br | —O—CH₂—C≡CH | |
| 2.226 | F | Br | —O—CH(CH₃)—C≡CH | |
| 2.227 | F | Br | —O—CH₂COOCH₃ | |
| 2.228 | F | Br | —O—CH₂—COOC₅H₁₁ | |
| 2.229 | F | Br | —S—CH₂—COOCH₃ | |
| 2.230 | F | Br | —S—△—COOC₂H₅ | |
| 2.231 | F | Br | —S—△—COOH (F) | |
| 2.232 | F | Br | —S—△—COOC₂H₅ (F) | |
| 2.233 | F | Cl | —S—CH₂COOH | |

TABLE 3

Compounds of formula Ie:

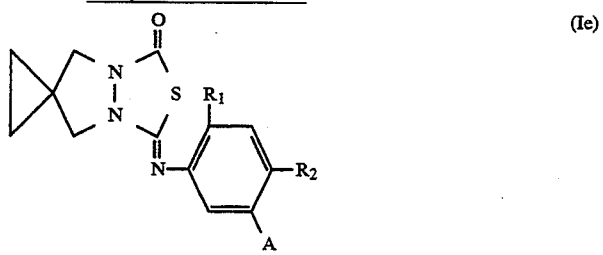

(Ie)

| Comp. No. | $R_1$ | $R_2$ | A | phys. data |
|---|---|---|---|---|
| 3.001 | F | Cl | —H | |
| 3.002 | F | Cl | —CN | |
| 3.003 | F | Cl | —NO$_2$ | |
| 3.004 | F | Cl | —COOH | |
| 3.005 | F | Cl | —COOCH$_3$ | m.p. 118–119° C. |
| 3.006 | F | Cl | —COOC$_2$H$_5$ | |
| 3.007 | F | Cl | —COOC$_3$H$_7$ | |
| 3.008 | F | Cl | —COOCH(CH$_3$)$_2$ | |
| 3.009 | F | Cl | —COOC$_4$H$_9$ | |
| 3.010 | F | Cl | —COOCH(CH$_3$)—CH$_2$—CH$_3$ | |
| 3.011 | F | Cl | —COOCH$_2$—CH$_2$—CH(CH$_3$)$_2$ | |
| 3.012 | F | Cl | —COOC$_5$H$_{11}$ | |
| 3.013 | F | Cl | —COOCH$_2$—CH$_2$—O—CH$_3$ | |
| 3.014 | F | Cl | —COOCH$_2$—CH$_2$—O—C$_2$H$_5$ | |
| 3.015 | F | Cl | —COOCH(CH$_3$)—CH$_2$—OCH$_3$ | |
| 3.016 | F | Cl | —COOCH$_2$—CH$_2$—S—CH$_3$ | |
| 3.017 | F | Cl | —COOCH(CH$_3$)—CH$_2$—S—CH$_3$ | |
| 3.018 | F | Cl | —COOCH(CH$_3$)—CH$_2$—S—C$_2$H$_5$ | |
| 3.019 | F | Cl | —COOCH(CH$_3$)—CH$_2$—S—C$_3$H$_7$ | |
| 3.020 | F | Cl | —COOCH(CH$_3$)—CH$_2$—S—CH(CH$_3$)$_2$ | |
| 3.021 | F | Cl | —COOCH(CH$_3$)—CH$_2$—S—C$_4$H$_9$ | |
| 3.022 | F | Cl | —COOCH(CH$_3$)—CH$_2$—S—C$_5$H$_{11}$ | |
| 3.023 | F | Cl | —COOCH(CH$_3$)—CH$_2$—N(CH$_3$)$_2$ | |
| 3.024 | F | Cl | —COOCH(CH$_3$)—CH$_2$—N(C$_2$H$_5$)$_2$ | |
| 3.025 | F | Cl | —CONH$_2$ | |
| 3.026 | F | Cl | —CONH—CH$_3$ | |
| 3.027 | F | Cl | —CON(CH$_3$)$_2$ | |
| 3.028 | F | Cl | —CON(CH$_3$)(C$_4$H$_9$) | |

TABLE 3-continued

Compounds of formula Ie:

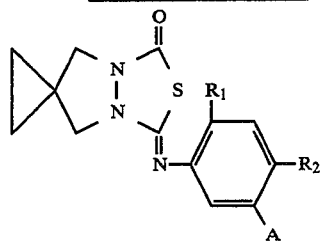

(Ie)

| Comp. No. | R₁ | R₂ | A | phys. data |
|---|---|---|---|---|
| 3.029 | F | Cl | —CON(CH₂—CH₂—OH)₂ | |
| 3.030 | F | Cl | —CONH—CH₂—CH=CH₂ | |
| 3.031 | F | Cl | —CON(CH₂—CH=CH₂)₂ | |
| 3.032 | F | Cl | —CON(pyrrolidine) | |
| 3.033 | F | Cl | —CON(piperidine) | |
| 3.034 | F | Cl | —CON(morpholine) | |
| 3.035 | F | Cl | —CON(thiomorpholine) | |
| 3.036 | F | Cl | —CON(N-methylpiperazine) | |
| 3.037 | F | Cl | —COON=C(CH₃)₂ | |
| 3.038 | F | Cl | —COOCH₂—CH₂—Cl | |
| 3.039 | F | Cl | —COOCH₂—CN | |
| 3.040 | F | Cl | —COOCH(CN)CH₃ | |
| 3.041 | F | Cl | —COOCH₂—CH=CH₂ | |
| 3.042 | F | Cl | —COOCH₂—CH=CHCl | |
| 3.043 | F | Cl | —COOCH₂—C(Cl)=CH₂ | |
| 3.044 | F | Cl | —COOCH₂—C≡CH | |
| 3.045 | F | Cl | —COO—CH(CH₃)—C≡CH | |

TABLE 3-continued
Compounds of formula Ie:
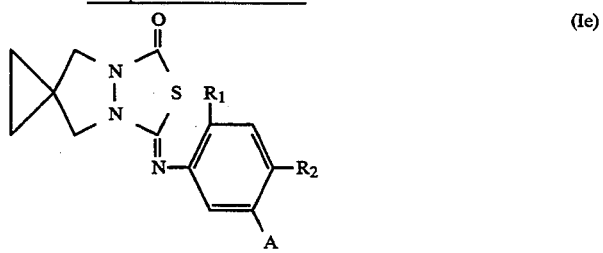
| Comp. No. | R₁ | R₂ | A | phys. data |
|---|---|---|---|---|
| 3.046 | F | Cl | 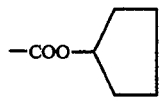 | |
| 3.047 | F | Cl | 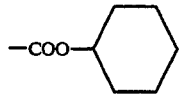 | |
| 3.048 | F | Cl | 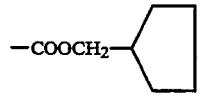 | |
| 3.049 | F | Cl | 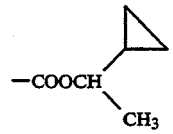 | |
| 3.050 | F | Cl | 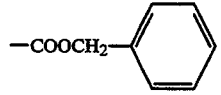 | |
| 3.051 | F | Cl | 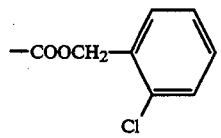 | |
| 3.052 | F | Cl | 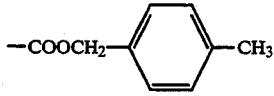 | |
| 3.053 | F | Cl | —COSCH₃ | |
| 3.054 | F | Cl | —COSC₂H₅ | |
| 3.055 | F | Cl | —COSC₃H₇ | |
| 3.056 | F | Cl | —COS—CH₂—CH=CH₂ | |
| 3.057 | F | Cl | —COS—CH₂—COOCH₃ | |
| 3.058 | F | Cl | —COS—CH₂—COOC₂H₅ | |
| 3.059 | F | Cl | —COS—CH₂—COOC₅H₁₁ | |
| 3.060 | F | Cl | —COS—CH(CH₃)—COOCH₃ | |
| 3.061 | F | Cl | —COS—CH(CH₃)—COOC₂H₅ | |
| 3.062 | F | Cl | —COS—CH(CH₃)—COOC₃H₇ | |

TABLE 3-continued

Compounds of formula Ie:

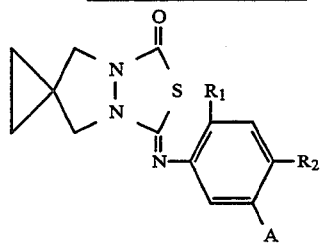

(Ie)

| Comp. No. | R₁ | R₂ | A | phys. data |
|---|---|---|---|---|
| 3.063 | F | Cl | —COS—CH₂—CH₂—COOCH₃ | |
| 3.064 | F | Cl | —COS—CH₂—COOCH₂—CH₂—O—CH₃ | |
| 3.065 | F | Cl | —COOCH₂—COOCH₃ | |
| 3.066 | F | Cl | —COOCH(CH₃)—COOCH₃ | |
| 3.067 | F | Cl | —COOCH₂—COOC₅H₁₁ | |
| 3.068 | F | Cl | —COOCH₂—CH₂—Si(CH₃)₃ | |
| 3.069 | F | Cl | —COONa | |
| 3.070 | F | Cl | —COOCH₂—CH₂—O—N=C(CH₃)₂ | |
| 3.071 | F | Cl | —OH | |
| 3.072 | F | Cl | —OCH₃ | |
| 3.073 | F | Cl | —OC₂H₅ | |
| 3.074 | F | Cl | —OC₃H₇ | |
| 3.075 | F | Cl | —OCH(CH₃)₂ | resin |
| 3.076 | F | Cl | —OC₄H₉ | |
| 3.077 | F | Cl | —OCH(CH₃)—C₂H₅ | |
| 3.078 | F | Cl | —O—CH₂—CH(CH₃)₂ | |
| 3.079 | F | Cl | —OCH₂CH=CH₂ | |
| 3.080 | F | Cl | —OCH₂—C(Cl)=CH₂ | |
| 3.081 | F | Cl | —OCH₂CH=CHCl | |
| 3.082 | F | Cl | —OCH₂C≡CH | |
| 3.083 | F | Cl | —OCH(CH₃)—C≡CH | |
| 3.084 | F | Cl | —OCH₂—COOCH₃ | |
| 3.085 | F | Cl | —O—CH₂—COOC₅H₁₁ | |
| 3.086 | F | Cl | —O—CH(CH₃)—COOCH₃ | |
| 3.087 | F | Cl | —O—CH₂—COOC₂H₅ | |

TABLE 3-continued

Compounds of formula Ie:

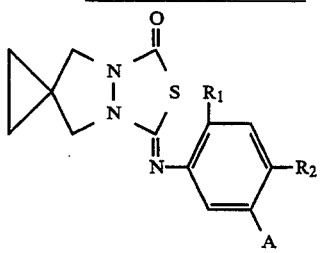

(Ie)

| Comp. No. | R₁ | R₂ | A | phys. data |
|---|---|---|---|---|
| 3.088 | F | Cl | —O—CH(CH₃)—COOC₂H₅ | |
| 3.089 | F | Cl | O—CH₂—CH₂—O—CH₃ | |
| 3.090 | F | Cl | —O—CH(CH₃)—CH₂—S—CH₃ | |
| 3.091 | F | Cl | —O—CH(CH₃)—CH₂—S—C₂H₅ | |
| 3.092 | F | Cl | —O—CH(CH₃)—CH₂—S—C₃H₇ | |
| 3.093 | F | Cl | —O—CH₂—CH₂—Cl | |
| 3.094 | F | Cl | —O—CH₂—CN | |
| 3.095 | F | Cl | —O—CH(CH₃)—CN | |
| 3.096 | F | Cl | —S—CH₃ | |
| 3.097 | F | Cl | —S—C₂H₅ | |
| 3.098 | F | Cl | —S—C₃H₇ | |
| 3.099 | F | Cl | —S—CH(CH₃)₂ | |
| 3.100 | F | Cl | —S—CH₂—CH=CH₂ | |
| 3.101 | F | Cl | —S—CH₂—C(Cl)=CH₂ | |
| 3.102 | F | Cl | —S—CH₂—CH=CHCl | |
| 3.103 | F | Cl | —S—CH₂—C≡CH | |
| 3.104 | F | Cl | —S—CH(CH₃)—C≡CH | |
| 3.105 | F | Cl | —S—CH₂—COOCH₃ | m.p. 63–65° C. |
| 3.106 | F | Cl | —S—CH₂—COOC₂H₅ | |
| 3.107 | F | Cl | —S—CH₂—COOC₅H₁₁ | |
| 3.108 | F | Cl | —S—CH(CH₃)—COOCH₃ | |
| 3.109 | F | Cl | —S—CH(CH₃)—COOC₂H₅ | |
| 3.110 | F | Cl | —S—CH₂—COOCH₂—CH₂—O—CH₃ | |

TABLE 3-continued
Compounds of formula Ie:
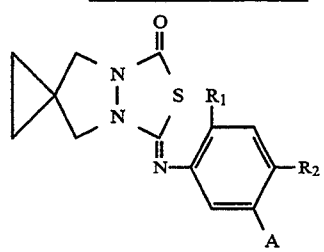 (Ie)
| Comp. No. | $R_1$ | $R_2$ | A | phys. data |
|---|---|---|---|---|
| 3.111 | F | Cl | —O—CH$_2$—C$_6$H$_5$ | |
| 3.112 | F | Cl | —S—CH$_2$—C$_6$H$_5$ | |
| 3.113 | F | Cl | —C(=N—O—CH$_3$)—CN | |
| 3.114 | F | Cl | —C(=N—O—CH$_2$—COOCH$_3$)—CN | |
| 3.115 | F | Cl | —C(=N—O—CH$_2$—C≡CH)—CN | |
| 3.116 | F | Cl | —C(=N—O—CH$_3$)—CH$_3$ | |
| 3.117 | F | Cl | —C(=N—O—CH$_2$—C≡CH)—CH$_3$ | |
| 3.118 | F | Cl | —C(=N—O—CH$_3$)—CH$_2$—O—CH$_3$ | |
| 3.119 | F | Cl | —C(CH$_3$)(O—CH$_3$)(O—CH$_3$) | |
| 3.120 | F | Cl | —C(CH$_3$)(O—C$_2$H$_5$)(O—C$_2$H$_5$) | |
| 3.121 | F | Cl | —C(CH$_3$)(O—CH$_2$—CH$_2$—O) (cyclic) | |

TABLE 3-continued
Compounds of formula Ie:
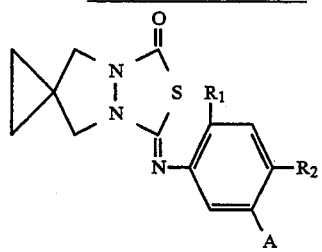
| Comp. No. | R₁ | R₂ | A | phys. data |
|---|---|---|---|---|
| 3.122 | F | Cl | —C(O—CH(CH₃))₂ with CH₃ groups (dioxolane with two methyls) | |
| 3.123 | F | Cl | —S—△—COOCH₃ | |
| 3.124 | F | Cl | —S—△—COOC₂H₅ | |
| 3.125 | F | Cl | —S—△—COOC₃H₇ | |
| 3.126 | F | Cl | —S—△—COOCH(CH₃)₂ | |
| 3.127 | F | Cl | —S—△—COO—CH₂—CH₂—Cl | |
| 3.128 | F | Cl | —S—△—COOC₅H₁₁ | |
| 3.129 | F | Cl | —S—△—COOCH₂—CH₂—O—CH₃ | |
| 3.130 | F | Cl | —S—△—COOCH(CH₃)—CH₂—S—CH₃ | |
| 3.131 | F | Cl | —S—△—COOCH(CH₃)—N(CH₃)₂ | |
| 3.132 | F | Cl | —S—△—COO-cyclopentyl | |
| 3.133 | F | Cl | —S—△—COO-cyclohexyl | |
| 3.134 | F | Cl | —S—△—COO—CH₂—CH₂—CH=CH₂ | |

TABLE 3-continued
Compounds of formula Ie:
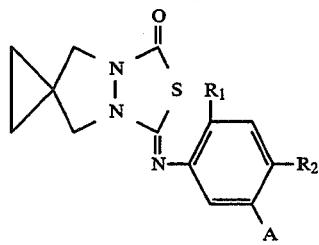
(Ie)
| Comp. No. | R₁ | R₂ | A | phys. data |
|---|---|---|---|---|
| 3.135 | F | Cl | —S—△—COO—CH₂—C(Cl)=CH₂ | |
| 3.136 | F | Cl | —S—△—COO—CH₂—C≡CH | |
| 3.137 | F | Cl | —S—△—COOH | |
| 3.138 | F | Cl | —S—△—CONH₂ | |
| 3.139 | F | Cl | —S—△—CONH—CH₃ | |
| 3.140 | F | Cl | —S—△(CH₃)—COOC₂H₅ | |
| 3.141 | F | Cl | —S—△(C₂H₅)—COOC₂H₅ | |
| 3.142 | F | Cl | —S—△(F)—COOCH₃ | |
| 3.143 | F | Cl | —S—△(F)—COOC₂H₅ | |
| 3.144 | F | Cl | —S—△—COO—CH(CH₃)₂ | |
| 3.145 | F | Cl | —S—△—COO—cyclopentyl | |
| 3.146 | F | Cl | —NH—SO₂—CH₃ | |
| 3.147 | F | Cl | —NH—SO₂—C₂H₅ | |
| 3.148 | F | Cl | —NH—SO₂—Cl | |
| 3.149 | F | Cl | —NH—SO₂—△ | |

TABLE 3-continued
Compounds of formula Ie:
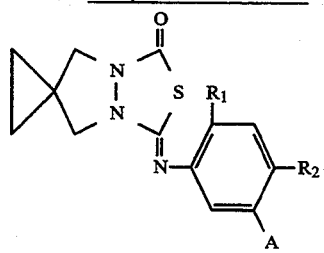
(Ie)
| Comp. No. | R₁ | R₂ | A | phys. data |
|---|---|---|---|---|
| 3.150 | F | Cl |  | |
| 3.151 | H | Cl | —COOH | |
| 3.152 | H | Cl | —COOCH₃ | m.p. > 85° C. (decomp.) |
| 3.153 | H | Cl | 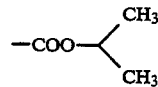 | wax |
| 3.154 | H | Cl | —COO—C₅H₁₁ | |
| 3.155 | H | Cl | —COO—CH₂—CH₂—O—CH₃ | |
| 3.156 | H | Cl | —COOCH₂—S—CH₃ | |
| 3.157 | H | Cl | —COOCH(CH₃)—CH₂—S—CH₃ | |
| 3.158 | H | Cl | 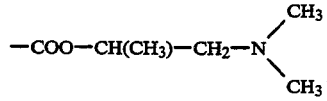 | |
| 3.159 | H | Cl | 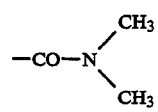 | |
| 3.160 | H | Cl | 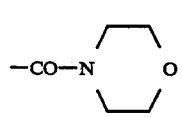 | |
| 3.161 | H | Cl | 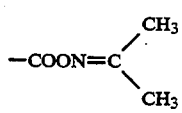 | |
| 3.162 | H | Cl | 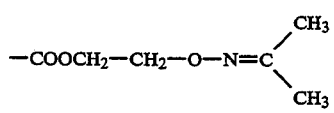 | |
| 3.163 | H | Cl | 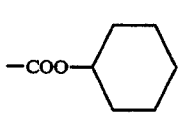 | |
| 3.164 | H | Cl | 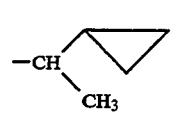 | |
| 3.165 | H | Cl | —S—C₃H₇ | |
| 3.166 | H | Cl | —COOCH₂—COOCH₃ | |
| 3.167 | H | Cl | —COOCH(CH₃)—COOCH₃ | |
| 3.168 | H | Cl | —COS—CH₂—COOCH₃ | |
| 3.169 | H | Cl | —COS—CH(CH₃)—COOCH₃ | |
| 3.170 | H | Cl | —OH | |
| 3.171 | H | Cl | —OCH₃ | |

TABLE 3-continued

Compounds of formula Ie:

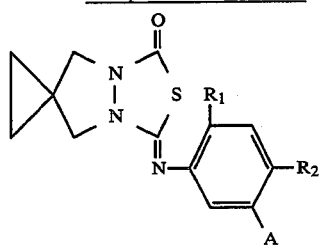

(Ie)

| Comp. No. | R$_1$ | R$_2$ | A | phys. data |
|---|---|---|---|---|
| 3.172 | H | Cl | —O—C$_2$H$_5$ | |
| 3.173 | H | Cl | —O—CH(CH$_3$)$_2$ | |
| 3.174 | H | Cl | —O—CH$_2$—C≡CH | |
| 3.175 | H | Cl | —O—CH$_2$—CH=CHCl | |
| 3.176 | H | Cl | —O—CH$_2$—C(Cl)=CH$_2$ | |
| 3.177 | H | Cl | —O—CH(CH$_3$)—C≡CH | |
| 3.178 | H | Cl | —O—CH$_2$—COOCH$_3$ | |
| 3.179 | H | Cl | —O—CH$_2$—COOC$_2$H$_5$ | |
| 3.180 | H | Cl | —O—CH(CH$_3$)—COOCH$_3$ | |
| 3.181 | H | Cl | —SH | |
| 3.182 | H | Cl | —SCH$_3$ | |
| 3.183 | H | Cl | —SC$_2$H$_5$ | |
| 3.184 | H | Cl | —S—CH(CH$_3$)$_2$ | |
| 3.185 | H | Cl | —S—CH$_2$—COOCH$_3$ | |
| 3.186 | H | Cl | —S—CH(CH$_3$)—COOCH$_3$ | |
| 3.187 | H | Cl | —S—CH$_2$—COOC$_2$H$_5$ | |
| 3.188 | H | Cl | —C(=N—OCH$_3$)—CN | |
| 3.189 | H | Cl | —C(CH$_3$)(O—CH(CH$_3$)—CH(CH$_3$)—O) | |
| 3.190 | H | Cl | —S—(cyclopropyl)—COOC$_2$H$_5$ | |
| 3.191 | H | Cl | —S—(cyclopropyl)—COOH | |
| 3.192 | H | Cl | —S—(cyclopropyl)—COO—CH(CH$_3$)$_2$ | |

TABLE 3-continued
Compounds of formula Ie:
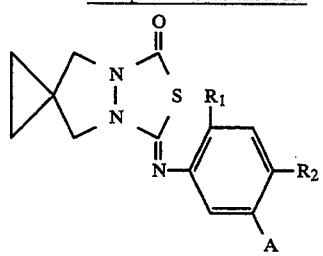
| Comp. No. | R₁ | R₂ | A | phys. data |
|---|---|---|---|---|
| 3.193 | H | Cl | 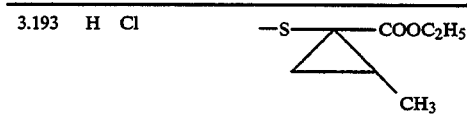 | |
| 3.194 | H | Cl | 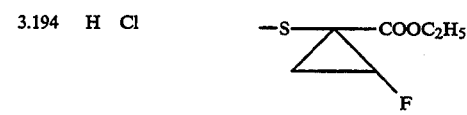 | |
| 3.195 | H | Cl | 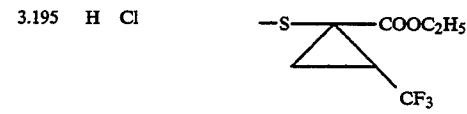 | |
| 3.196 | H | Cl | 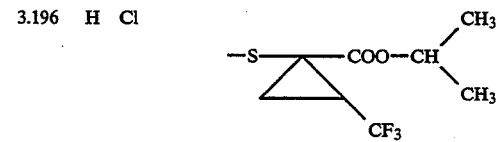 | |
| 3.197 | H | Cl |  | |
| 3.198 | H | Cl |  | |
| 3.199 | H | Cl | 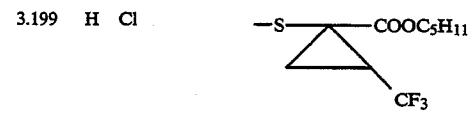 | |
| 3.200 | H | Cl | 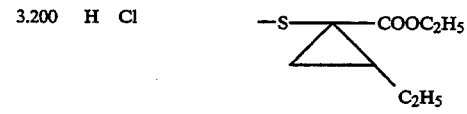 | |
| 3.201 | H | Cl | 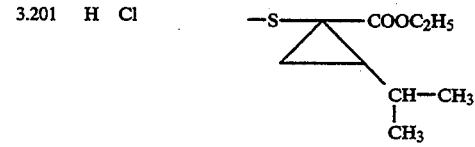 | |
| 3.202 | H | Cl | —NH—SO₂—C₂H₅ | |
| 3.203 | H | Cl | —NH—SO₂—CH₂—Cl | |
| 3.204 | F | CN | —COOH | |
| 3.205 | F | CN |  | |

TABLE 3-continued

Compounds of formula Ie:

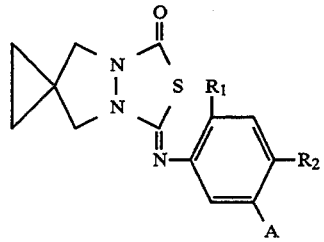

(Ie)

| Comp. No. | R₁ | R₂ | A | phys. data |
|---|---|---|---|---|
| 3.206 | F | CN | —O—CH(CH₃)₂ | |
| 3.207 | F | CN | —O—CH₂—C≡CH | |
| 3.208 | F | CN | —O—CH(CH₃)—C≡CH | |
| 3.209 | F | CN | —S—CH₂—COOCH₃ | |
| 3.210 | F | CN | —S—CH(CH₃)—COOCH₃ | |
| 3.211 | F | CN | —O—CH₂—COOCH₃ | |
| 3.212 | F | CN | —O—CH₂—COOC₅H₁₁ | |
| 3.213 | F | CN | —O—CH(CH₃)—COOC₂H₅ | |
| 3.214 | F | CN | —S—(cyclopropyl)—COOCH₃ | |
| 3.215 | F | CN | —S—(cyclopropyl)—COOC₂H₅ | |
| 3.216 | F | CN | —S—(cyclopropyl(F))—COOC₂H₅ | |
| 3.217 | F | CN | —S—(cyclopropyl)—COOH | |
| 3.218 | F | CN | —S—(cyclopropyl(F))—COOH | |
| 3.219 | F | CN | —S—(cyclopropyl(CF₃))—COOH | |
| 3.220 | F | CN | —S—(cyclopropyl)—COOC₂H₅ | |
| 3.221 | F | Br | —COOH | |
| 3.222 | F | Br | —COO—CH(CH₃)₂ | |
| 3.223 | F | Br | —OH | |
| 3.224 | F | Br | —O—CH(CH₃)₂ | |
| 3.225 | F | Br | —O—CH₂—C≡CH | |
| 3.226 | F | Br | —O—CH(CH₃)—C≡CH | |
| 3.227 | F | Br | —O—CH₂COOCH₃ | |

TABLE 3-continued

Compounds of formula Ie:

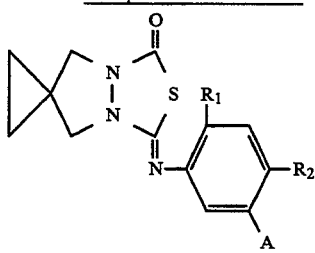

(Ie)

| Comp. No. | R₁ | R₂ | A | phys. data |
|---|---|---|---|---|
| 3.228 | F | Br | —O—CH₂—COOC₅H₁₁ | |
| 3.229 | F | Br | —S—CH₂—COOCH₃ | |
| 3.230 | F | Br | —S—⟨cyclopropyl⟩—COOC₂H₅ | |
| 3.231 | F | Br | —S—⟨cyclopropyl-F⟩—COOH | |
| 3.232 | F | Br | —S—⟨cyclopropyl-F⟩—COOC₂H₅ | |
| 3.233 | F | Cl | —S—CH₂COOH | |

TABLE 4

Compounds of formula If

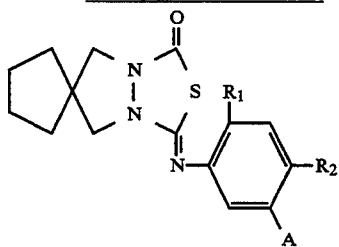

(If)

| Comp. No. | R₁ | R₂ | A | phys. data |
|---|---|---|---|---|
| 4.001 | F | Cl | —H | |
| 4.002 | F | Cl | —CN | |
| 4.003 | F | Cl | —NO₂ | |
| 4.004 | F | Cl | —COOH | |
| 4.005 | F | Cl | —COOCH₃ | |
| 4.006 | F | Cl | —COOC₂H₅ | |
| 4.007 | F | Cl | —COOC₃H₇ | |
| 4.008 | F | Cl | —COOCH(CH₃)₂ | |
| 4.009 | F | Cl | —COOC₄H₉ | |
| 4.010 | F | Cl | —COOCH(CH₃)—CH₂—CH₃ | |
| 4.011 | F | Cl | —COOCH₂—CH₂—CH(CH₃)₂ | |
| 4.012 | F | Cl | —COOC₅H₁₁ | |
| 4.013 | F | Cl | —COOCH₂—CH₂—O—CH₃ | |
| 4.014 | F | Cl | —COOCH₂—CH₂—O—C₂H₅ | |
| 4.015 | F | Cl | —COOCH(CH₃)—CH₂—OCH₃ | |
| 4.016 | F | Cl | —COOCH₂—CH₂—S—CH₃ | |
| 4.017 | F | Cl | —COOCH(CH₃)—CH₂—S—CH₃ | |
| 4.018 | F | Cl | —COOCH(CH₃)—CH₂—S—C₂H₅ | |

TABLE 4-continued

Compounds of formula If (If)

| Comp. No. | R₁ | R₂ | A | phys. data |
|---|---|---|---|---|
| 4.019 | F | Cl | —COOCH(CH₃)—CH₂—S—C₃H₇ | |
| 4.020 | F | Cl | —COOCH(CH₃)—CH₂—S—CH(CH₃)₂ | |
| 4.021 | F | Cl | —COOCH(CH₃)—CH₂—S—C₄H₉ | |
| 4.022 | F | Cl | —COOCH(CH₃)—CH₂—S—C₅H₁₁ | |
| 4.023 | F | Cl | —COOCH(CH₃)—CH₂—N(CH₃)₂ | |
| 4.024 | F | Cl | —COOCH(CH₃)—CH₂—N(C₂H₅)₂ | |
| 4.025 | F | Cl | —CONH₂ | |
| 4.026 | F | Cl | —CONH—CH₃ | |
| 4.027 | F | Cl | —CON(CH₃)₂ | |
| 4.028 | F | Cl | —CON(CH₃)(C₄H₉) | |
| 4.029 | F | Cl | —CON(CH₂—CH₂—OH)₂ | |
| 4.030 | F | Cl | —CONH—CH₂—CH=CH₂ | |
| 4.031 | F | Cl | —CON(CH₂—CH=CH₂)₂ | |
| 4.032 | F | Cl | —CON(pyrrolidinyl) | |
| 4.033 | F | Cl | —CON(piperidinyl) | |
| 4.034 | F | Cl | —CON(morpholinyl) | |

TABLE 4-continued
Compounds of formula If
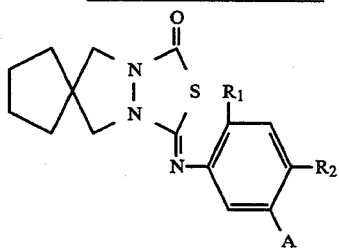
(If)
| Comp. No. | R₁ | R₂ | A | phys. data |
|---|---|---|---|---|
| 4.035 | F | Cl | 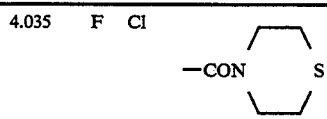 | |
| 4.036 | F | Cl | 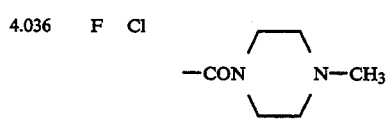 | |
| 4.037 | F | Cl | 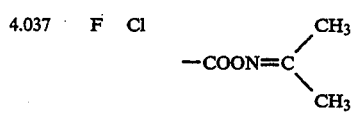 | |
| 4.038 | F | Cl | —COOCH₂—CH₂—Cl | |
| 4.039 | F | Cl | —COOCH₂—CN | |
| 4.040 | F | Cl | 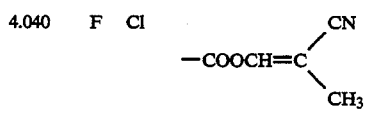 | |
| 4.041 | F | Cl | —COOCH₂—CH=CH₂ | |
| 4.042 | F | Cl | —COOCH₂—CH=CHCl | |
| 4.043 | F | Cl | 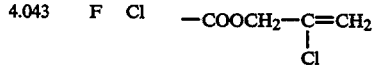 | |
| 4.044 | F | Cl | —COOCH₂—C≡CH | |
| 4.045 | F | Cl | 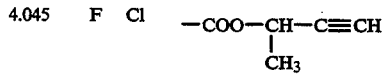 | |
| 4.046 | F | Cl | 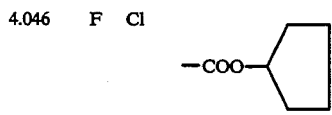 | |
| 4.047 | F | Cl | 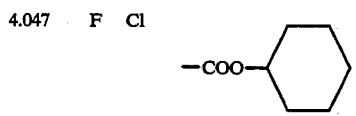 | |
| 4.048 | F | Cl | 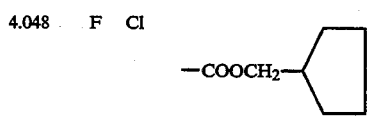 | |
| 4.049 | F | Cl | 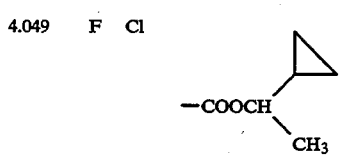 | |

TABLE 4-continued

Compounds of formula If

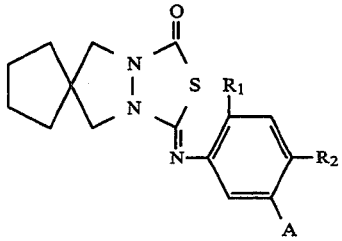

(If)

| Comp. No. | R$_1$ | R$_2$ | A | phys. data |
|---|---|---|---|---|
| 4.050 | F | Cl | —COOCH$_2$—C$_6$H$_5$ | |
| 4.051 | F | Cl | —COOCH$_2$—(2-Cl-C$_6$H$_4$) | |
| 4.052 | F | Cl | —COOCH$_2$—(4-CH$_3$-C$_6$H$_4$) | |
| 4.053 | F | Cl | —COSCH$_3$ | |
| 4.054 | F | Cl | —COSC$_2$H$_5$ | |
| 4.055 | F | Cl | —COSC$_3$H$_7$ | |
| 4.056 | F | Cl | —COS—CH$_2$—CH=CH$_2$ | |
| 4.057 | F | Cl | —COS—CH$_2$—COOCH$_3$ | |
| 4.058 | F | Cl | —COS—CH$_2$—COOC$_2$H$_5$ | |
| 4.059 | F | Cl | —COS—CH$_2$—COOC$_5$H$_{11}$ | |
| 4.060 | F | Cl | —COS—CH(CH$_3$)—COOCH$_3$ | |
| 4.061 | F | Cl | —COS—CH(CH$_3$)—COOC$_2$H$_5$ | |
| 4.062 | F | Cl | —COS—CH(CH$_3$)—COOC$_3$H$_7$ | |
| 4.063 | F | Cl | —COS—CH$_2$—CH$_2$—COOCH$_3$ | |
| 4.064 | F | Cl | —COS—CH$_2$—COOCH$_2$—CH$_2$—O—CH$_3$ | |
| 4.065 | F | Cl | —COOCH$_2$—COOCH$_3$ | |
| 4.066 | F | Cl | —COOCH(CH$_3$)—COOCH | |
| 4.067 | F | Cl | —COOCH$_2$—COOC$_5$H$_{11}$ | |
| 4.068 | F | Cl | —COOCH$_2$—CH$_2$—Si(CH$_3$)$_3$ | |
| 4.069 | F | Cl | —COONa | |
| 4.070 | F | Cl | —COOCH$_2$—CH$_2$—O—N=C(CH$_3$)$_2$ | |
| 4.071 | F | Cl | —OH | |
| 4.072 | F | Cl | —OCH$_3$ | |
| 4.073 | F | Cl | —OC$_2$H$_5$ | |
| 4.074 | F | Cl | —OC$_3$H$_7$ | |

TABLE 4-continued

Compounds of formula If

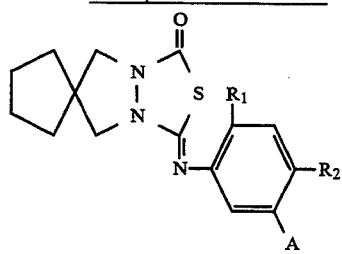

(If)

| Comp. No. | R₁ | R₂ | A | phys. data |
|---|---|---|---|---|
| 4.075 | F | Cl | —OCH(CH₃)₂ | |
| 4.076 | F | Cl | —OC₄H₉ | |
| 4.077 | F | Cl | —OCH(CH₃)—C₂H₅ | |
| 4.078 | F | Cl | —O—CH₂—CH(CH₃)₂ | |
| 4.079 | F | Cl | —OCH₂CH=CH₂ | |
| 4.080 | F | Cl | —OCH₂—C(Cl)=CH₂ | |
| 4.081 | F | Cl | —OCH₂CH=CHCl | |
| 4.082 | F | Cl | —OCH₂C≡CH | |
| 4.083 | F | Cl | —OCH(CH₃)—C≡CH | |
| 4.084 | F | Cl | —OCH₂—COOCH₃ | |
| 4.085 | F | Cl | —O—CH₂—COOC₅H₁₁ | |
| 4.086 | F | Cl | —O—CH(CH₃)—COOCH₃ | |
| 4.087 | F | Cl | —O—CH₂—COOC₂H₅ | |
| 4.088 | F | Cl | —O—CH(CH₃)—COOC₂H₅ | |
| 4.089 | F | Cl | —O—CH₂—CH₂—O—CH₃ | |
| 4.090 | F | Cl | —O—CH(CH₃)—CH₂—S—CH₃ | |
| 4.091 | F | Cl | —O—CH(CH₃)—CH₂—S—C₂H₅ | |
| 4.092 | F | Cl | —O—CH(CH₃)—CH₂—S—C₃H₇ | |
| 4.093 | F | Cl | —O—CH₂—CH₂—Cl | |
| 4.094 | F | Cl | —O—CH₂—CN | |
| 4.095 | F | Cl | —O—CH(CH₃)—CN | |
| 4.096 | F | Cl | —S—CH₃ | |

TABLE 4-continued

Compounds of formula If

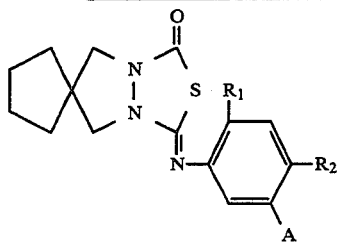

(If)

| Comp. No. | R₁ | R₂ | A | phys. data |
|---|---|---|---|---|
| 4.097 | F | Cl | —S—C₂H₅ | |
| 4.098 | F | Cl | —S—C₃H₇ | |
| 4.099 | F | Cl | —S—CH(CH₃)₂ | |
| 4.100 | F | Cl | —S—CH₂—CH=CH₂ | |
| 4.101 | F | Cl | —S—CH₂—C(Cl)=CH₂ | |
| 4.102 | F | Cl | —S—CH₂—CH=CHCl | |
| 4.103 | F | Cl | —S—CH₂—C≡CH | |
| 4.104 | F | Cl | —S—CH(CH₃)—C≡CH | |
| 4.105 | F | Cl | —S—CH₂—COOCH₃ | |
| 4.106 | F | Cl | —S—CH₂—COOC₂H₅ | |
| 4.107 | F | Cl | —S—CH₂—COOC₅H₁₁ | |
| 4.108 | F | Cl | —S—CH(CH₃)—COOCH₃ | |
| 4.109 | F | Cl | —S—CH(CH₃)—COOC₂H₅ | |
| 4.110 | F | Cl | —S—CH₂—COOCH₂—CH₂—O—CH₃ | |
| 4.111 | F | Cl | —O—CH₂—C₆H₅ | |
| 4.112 | F | Cl | —S—CH₂—C₆H₅ | |
| 4.113 | F | Cl | —C(=N—O—CH₃)—CN | |
| 4.114 | F | Cl | —C(=N—O—CH₂—COOCH₃)—CN | |
| 4.115 | F | Cl | —C(=N—O—CH₂—C≡CH)—CN | |
| 4.116 | F | Cl | —C(=N—O—CH₃)—CH₃ | |

TABLE 4-continued

Compounds of formula If

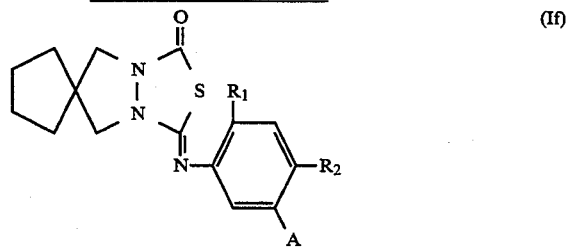

(If)

| Comp. No. | R₁ | R₂ | A | phys. data |
|---|---|---|---|---|
| 4.117 | F | Cl | —C(=N—O—CH₂—C≡CH)—CH₃ | |
| 4.118 | F | Cl | —C(=N—O—CH₃)—CH₂—O—CH₃ | |
| 4.119 | F | Cl | —C(CH₃)(O—CH₃)(O—CH₃) | |
| 4.120 | F | Cl | —C(CH₃)(O—C₂H₅)(O—C₂H₅) | |
| 4.121 | F | Cl | —C(CH₃)(OCH₂CH₂O—) | |
| 4.122 | F | Cl | —C(CH₃)(OCH(CH₃)CH(CH₃)O—) | |
| 4.123 | F | Cl | —S—(cyclopropyl)—COOCH₃ | |
| 4.124 | F | Cl | —S—(cyclopropyl)—COOC₂H₅ | |
| 4.125 | F | Cl | —S—(cyclopropyl)—COOC₃H₇ | |
| 4.126 | F | Cl | —S—(cyclopropyl)—COOCH(CH₃)₂ | |
| 4.127 | F | Cl | —S—(cyclopropyl)—COO—CH₂—CH₂—Cl | |
| 4.128 | F | Cl | —S—(cyclopropyl)—COOC₅H₁₁ | |
| 4.129 | F | Cl | —S—(cyclopropyl)—COOCH₂—CH₂—O—CH₃ | |

TABLE 4-continued
Compounds of formula If
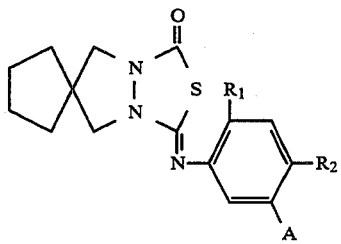
(If)
| Comp. No. | R₁ | R₂ | A | phys. data |
|---|---|---|---|---|
| 4.130 | F | Cl | —S—△—COOCH(CH₃)—CH₂—S—CH₃ | |
| 4.131 | F | Cl | —S—△—COOCH(CH₃)—N(CH₃)₂ | |
| 4.132 | F | Cl | —S—△—COO—cyclopentyl | |
| 4.133 | F | Cl | —S—△—COO—cyclohexyl | |
| 4.134 | F | Cl | —S—△—COO—CH₂—CH₂—CH=CH₂ | |
| 4.135 | F | Cl | —S—△—COO—CH₂—C(Cl)=CH₂ | |
| 4.136 | F | Cl | —S—△—COO—CH₂—C≡CH | |
| 4.137 | F | Cl | —S—△—COOH | |
| 4.138 | F | Cl | —S—△—CONH₂ | |
| 4.139 | F | Cl | —S—△—CONH—CH₃ | |
| 4.140 | F | Cl | —S—△(CH₃)—COOC₂H₅ | |
| 4.141 | F | Cl | —S—△(C₂H₅)—COOC₂H₅ | |
| 4.142 | F | Cl | —S—△(F)—COOCH₃ | |

TABLE 4-continued
Compounds of formula If
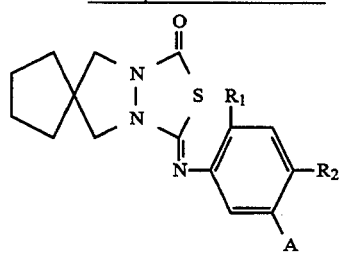
(If)
| Comp. No. | R₁ | R₂ | A | phys. data |
|---|---|---|---|---|
| 4.143 | F | Cl | 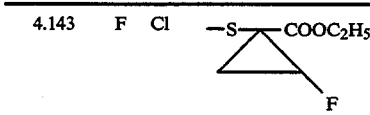 | |
| 4.144 | F | Cl | 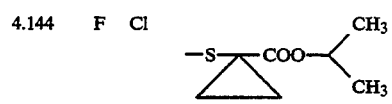 | |
| 4.145 | F | Cl | 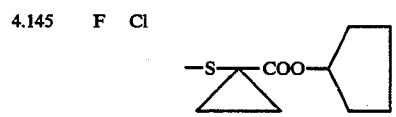 | |
| 4.146 | F | Cl | —NH—SO$_2$—CH$_3$ | |
| 4.147 | F | Cl | —NH—SO$_2$—C$_2$H$_5$ | |
| 4.148 | F | Cl | —NH—SO$_2$—Cl | |
| 4.149 | F | Cl | 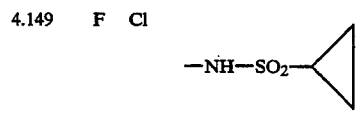 | |
| 4.150 | F | Cl | 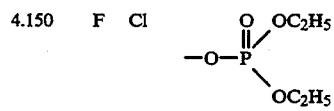 | |
| 4.151 | H | Cl | —COOH | |
| 4.152 | H | Cl | —COOCH$_3$ | |
| 4.153 | H | Cl | 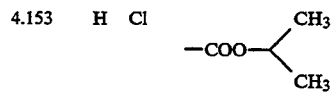 | |
| 4.154 | H | Cl | —COO—C$_5$H$_{11}$ | |
| 4.155 | H | Cl | —COO—CH$_2$—CH$_2$—O—CH$_3$ | |
| 4.156 | H | Cl | —COOCH$_2$—S—CH$_3$ | |
| 4.157 | H | Cl | —COOCH(CH$_3$)—CH$_2$—S—CH$_3$ | |
| 4.158 | H | Cl | 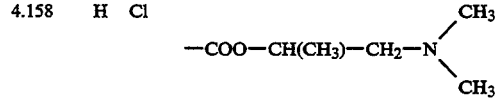 | |
| 4.159 | H | Cl | 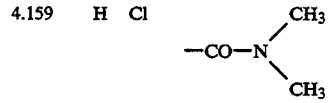 | |
| 4.160 | H | Cl | 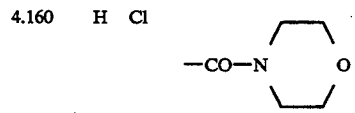 | |

TABLE 4-continued

Compounds of formula If

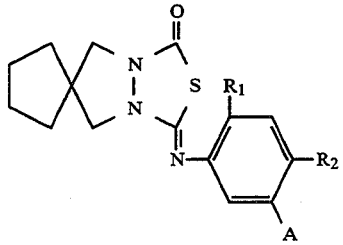

(If)

| Comp. No. | R₁ | R₂ | A | phys. data |
|---|---|---|---|---|
| 4.161 | H | Cl | —COON=C(CH₃)(CH₃) | |
| 4.162 | H | Cl | —COOCH₂—CH₂—O—N=C(CH₃)(CH₃) | |
| 4.163 | H | Cl | —COO—cyclohexyl | |
| 4.164 | H | Cl | —CH(CH₃)(cyclopropyl) | |
| 4.165 | H | Cl | —S—C₃H₇ | |
| 4.166 | H | Cl | —COOCH₂—COOCH₃ | |
| 4.167 | H | Cl | —COOCH(CH₃)—COOCH₃ | |
| 4.168 | H | Cl | —COS—CH₂—COOCH₃ | |
| 4.169 | H | Cl | —COS—CH(CH₃)—COOCH₃ | |
| 4.170 | H | Cl | —OH | |
| 4.171 | H | Cl | —OCH₃ | |
| 4.172 | H | Cl | —O—C₂H₅ | |
| 4.173 | H | Cl | —O—CH(CH₃)(CH₃) | |
| 4.174 | H | Cl | —O—CH₂—C≡CH | |
| 4.175 | H | Cl | —O—CH₂—CH=CHCl | |
| 4.176 | H | Cl | —O—CH₂—C(Cl)=CH₂ | |
| 4.177 | H | Cl | —O—CH(CH₃)—C≡CH | |
| 4.178 | H | Cl | —O—CH₂—COOCH₃ | |
| 4.179 | H | Cl | —O—CH₂—COOC₂H₅ | |
| 4.180 | H | Cl | —O—CH(CH₃)—COOCH₃ | |
| 4.181 | H | Cl | —SH | |
| 4.182 | H | Cl | —SCH₃ | |
| 4.183 | H | Cl | —SC₂H₅ | |
| 4.184 | H | Cl | —S—CH(CH₃)(CH₃) | |
| 4.185 | H | Cl | —S—CH₂—COOCH₃ | |
| 4.186 | H | Cl | —S—CH(CH₃)—COOCH₃ | |
| 4.187 | H | Cl | —S—CH₂—COOC₂H₅ | |

TABLE 4-continued

Compounds of formula If

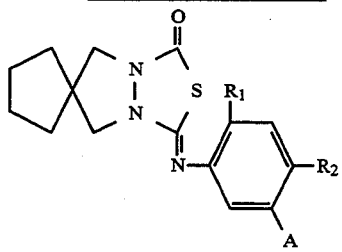

(If)

| Comp. No. | R₁ | R₂ | A | phys. data |
|---|---|---|---|---|
| 4.188 | H | Cl | —C(=N—OCH₃)—CN | |
| 4.189 | H | Cl | 2-methyl-1,3-dioxolan-2-yl with 4,5-dimethyl (−C(CH₃)(O−)(O−) with CH(CH₃)CH(CH₃)) | |
| 4.190 | H | Cl | —S—[cyclopropyl]—COOC₂H₅ | |
| 4.191 | H | Cl | —S—[cyclopropyl]—COOH | |
| 4.192 | H | Cl | —S—[cyclopropyl]—COO—CH(CH₃)₂ | |
| 4.193 | H | Cl | —S—[cyclopropyl(CH₃)]—COOC₂H₅ | |
| 4.194 | H | Cl | —S—[cyclopropyl(F)]—COOC₂H₅ | |
| 4.195 | H | Cl | —S—[cyclopropyl(CF₃)]—COOC₂H₅ | |
| 4.196 | H | Cl | —S—[cyclopropyl(CF₃)]—COO—CH(CH₃)₂ | |
| 4.197 | H | Cl | —S—[cyclopropyl]—COOH | |
| 4.198 | H | Cl | —S—[cyclopropyl(CF₃)]—COOH | |
| 4.199 | H | Cl | —S—[cyclopropyl(CF₃)]—COOC₅H₁₁ | |

TABLE 4-continued

Compounds of formula If

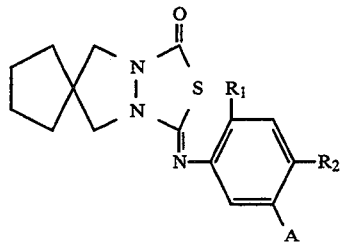

(If)

| Comp. No. | R₁ | R₂ | A | phys. data |
|---|---|---|---|---|
| 4.200 | H | Cl | —S—⟨△⟩—COOC₂H₅, C₂H₅ | |
| 4.201 | H | Cl | —S—⟨△⟩—COOC₂H₅, CH(CH₃)₂ | |
| 4.202 | H | Cl | —NH—SO₂—C₂H₅ | |
| 4.203 | H | Cl | —NH—SO₂—CH₂—Cl | |
| 4.204 | F | CN | —COOH | |
| 4.205 | F | CN | —COO—CH(CH₃)₂ | |
| 4.206 | F | CN | —O—CH(CH₃)₂ | |
| 4.207 | F | CN | —O—CH₂—C≡CH | |
| 4.208 | F | CN | —O—CH(CH₃)—C≡CH | |
| 4.209 | F | CN | —S—CH₂—COOCH₃ | |
| 4.210 | F | CN | —S—CH(CH₃)—COOCH₃ | |
| 4.211 | F | CN | —O—CH₂—COOCH₃ | |
| 4.212 | F | CN | —O—CH₂—COOC₅H₁₁ | |
| 4.213 | F | CN | —O—CH(CH₃)—COOC₂H₅ | |
| 4.214 | F | CN | —S—⟨△⟩—COOCH₃ | |
| 4.215 | F | CN | —S—⟨△⟩—COOC₂H₅ | |
| 4.216 | F | CN | —S—⟨△⟩—COOC₂H₅, F | |
| 4.217 | F | CN | —S—⟨△⟩—COOH | |
| 4.218 | F | CN | —S—⟨△⟩—COOH, F | |
| 4.219 | F | CN | —S—⟨△⟩—COOH, CF₃ | |

TABLE 4-continued
Compounds of formula If
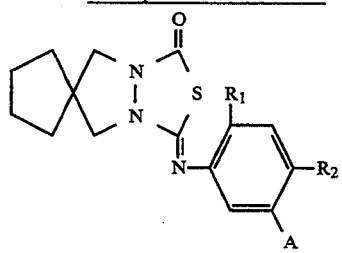
(If)
| Comp. No. | R₁ | R₂ | A | phys. data |
|---|---|---|---|---|
| 4.220 | F | CN | —S—△—COOC₂H₅ | |
| 4.221 | F | Br | —COOH | |
| 4.222 | F | Br | —COO—CH(CH₃)₂ | |
| 4.223 | F | Br | —OH | |
| 4.224 | F | Br | —O—CH(CH₃)₂ | |
| 4.225 | F | Br | —O—CH₂—C≡CH | |
| 4.226 | F | Br | —O—CH(CH₃)—C≡CH | |
| 4.227 | F | Br | —O—CH₂COOCH₃ | |
| 4.228 | F | Br | —O—CH₂—COOC₅H₁₁ | |
| 4.229 | F | Br | —S—CH₂—COOCH₃ | |
| 4.230 | F | Br | —S—△—COOC₂H₅ | |
| 4.231 | F | Br | —S—△(COOH)(F) | |
| 4.232 | F | Br | —S—△(COOC₂H₅)(F) | |
| 4.233 | F | Cl | —S—CH₂COOH | |
TABLE 5
Compounds of formula Ig
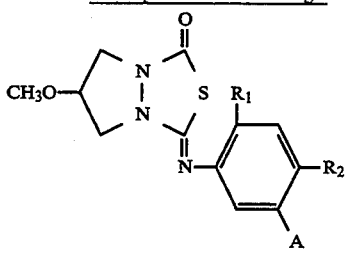
(Ig)
| Comp. No. | R₁ | R₂ | A | phys. data |
|---|---|---|---|---|
| 5.001 | F | Cl | —H | |
| 5.002 | F | Cl | —CN | |
| 5.003 | F | Cl | —NO₂ | |
| 5.004 | F | Cl | —COOH | |
| 5.005 | F | Cl | —COOCH₃ | |

TABLE 5-continued

Compounds of formula Ig

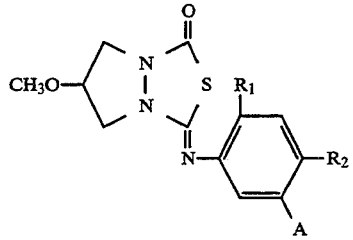

(Ig)

| Comp. No. | $R_1$ | $R_2$ | A | phys. data |
|---|---|---|---|---|
| 5.006 | F | Cl | —COOC$_2$H$_5$ | |
| 5.007 | F | Cl | —COOC$_3$H$_7$ | |
| 5.008 | F | Cl | —COOCH(CH$_3$)$_2$ | |
| 5.009 | F | Cl | —COOC$_4$H$_9$ | |
| 5.010 | F | Cl | —COOCH(CH$_3$)—CH$_2$—CH$_3$ | |
| 5.011 | F | Cl | —COOCH$_2$—CH$_2$—CH(CH$_3$)$_2$ | |
| 5.012 | F | Cl | —COOC$_5$H$_{11}$ | |
| 5.013 | F | Cl | —COOCH$_2$—CH$_2$—O—CH$_3$ | |
| 5.014 | F | Cl | —COOCH$_2$—CH$_2$—O—C$_2$H$_5$ | |
| 5.015 | F | Cl | —COOCH(CH$_3$)—CH$_2$—OCH$_3$ | |
| 5.016 | F | Cl | —COOCH$_2$—CH$_2$—S—CH$_3$ | |
| 5.017 | F | Cl | —COOCH(CH$_3$)—CH$_2$—S—CH$_3$ | |
| 5.018 | F | Cl | —COOCH(CH$_3$)—CH$_2$—S—C$_2$H$_5$ | |
| 5.019 | F | Cl | —COOCH(CH$_3$)—CH$_2$—S—C$_3$H$_7$ | |
| 5.020 | F | Cl | —COOCH(CH$_3$)—CH$_2$—S—CH(CH$_3$)$_2$ | |
| 5.021 | F | Cl | —COOCH(CH$_3$)—CH$_2$—S—C$_4$H$_9$ | |
| 5.022 | F | Cl | —COOCH(CH$_3$)—CH$_2$—S—C$_5$H$_{11}$ | |
| 5.023 | F | Cl | —COOCH(CH$_3$)—CH$_2$—N(CH$_3$)$_2$ | |
| 5.024 | F | Cl | —COOCH(CH$_3$)—CH$_2$—N(C$_2$H$_5$)$_2$ | |
| 5.025 | F | Cl | —CONH$_2$ | |
| 5.026 | F | Cl | —CONH—CH$_3$ | |
| 5.027 | F | Cl | —CON(CH$_3$)$_2$ | |
| 5.028 | F | Cl | —CON(CH$_3$)(C$_4$H$_9$) | |
| 5.029 | F | Cl | —CON(CH$_2$—CH$_2$—OH)$_2$ | |
| 5.030 | F | Cl | —CONH—CH$_2$—CH=CH$_2$ | |
| 5.031 | F | Cl | —CON(CH$_2$—CH=CH$_2$)$_2$ | |

TABLE 5-continued

Compounds of formula Ig

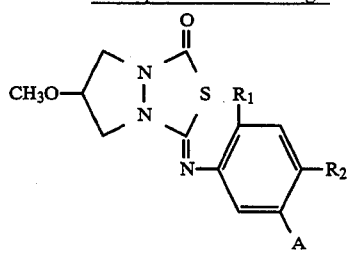

(Ig)

| Comp. No. | R₁ | R₂ | A | phys. data |
|---|---|---|---|---|
| 5.032 | F | Cl | —CON⟨(CH₂)₄⟩ (pyrrolidine) | |
| 5.033 | F | Cl | —CON⟨(CH₂)₅⟩ (piperidine) | |
| 5.034 | F | Cl | —CON⟨morpholine-O⟩ | |
| 5.035 | F | Cl | —CON⟨thiomorpholine-S⟩ | |
| 5.036 | F | Cl | —CON⟨piperazine-N—CH₃⟩ | |
| 5.037 | F | Cl | —COON=C(CH₃)₂ | |
| 5.038 | F | Cl | —COOCH₂—CH₂—Cl | |
| 5.039 | F | Cl | —COOCH₂—CN | |
| 5.040 | F | Cl | —COOCH(CN)CH₃ | |
| 5.041 | F | Cl | —COOCH₂—CH=CH₂ | |
| 5.042 | F | Cl | —COOCH₂—CH=CHCl | |
| 5.043 | F | Cl | —COOCH₂—C(Cl)=CH₂ | |
| 5.044 | F | Cl | —COOCH₂—C≡CH | |
| 5.045 | F | Cl | —COO—CH(CH₃)—C≡CH | |
| 5.046 | F | Cl | —COO—cyclopentyl | |

TABLE 5-continued

Compounds of formula Ig

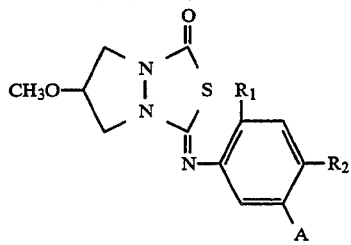

(Ig)

| Comp. No. | R₁ | R₂ | A | phys. data |
|---|---|---|---|---|
| 5.047 | F | Cl | —COO—(cyclohexyl) | |
| 5.048 | F | Cl | —COOCH₂—(cyclopentyl) | |
| 5.049 | F | Cl | —COOCH(CH₃)—(cyclopropyl) | |
| 5.050 | F | Cl | —COOCH₂—(phenyl) | |
| 5.051 | F | Cl | —COOCH₂—(2-chlorophenyl) | |
| 5.052 | F | Cl | —COOCH₂—(4-methylphenyl) | |
| 5.053 | F | Cl | —COSCH₃ | |
| 5.054 | F | Cl | —COSC₂H₅ | |
| 5.055 | F | Cl | —COSC₃H₇ | |
| 5.056 | F | Cl | —COS—CH₂—CH=CH₂ | |
| 5.057 | F | Cl | —COS—CH₂—COOCH₃ | |
| 5.058 | F | Cl | —COS—CH₂—COOC₂H₅ | |
| 5.059 | F | Cl | —COS—CH₂—COOC₅H₁₁ | |
| 5.060 | F | Cl | —COS—CH(CH₃)—COOCH₃ | |
| 5.061 | F | Cl | —COS—CH(CH₃)—COOC₂H₅ | |
| 5.062 | F | Cl | —COS—CH(CH₃)—COOC₃H₇ | |
| 5.063 | F | Cl | —COS—CH₂—CH₂—COOCH₃ | |
| 5.064 | F | Cl | —COS—CH₂—COOCH₂—CH₂—O—CH₃ | |
| 5.065 | F | Cl | —COOCH₂—COOCH₃ | |

TABLE 5-continued

Compounds of formula Ig

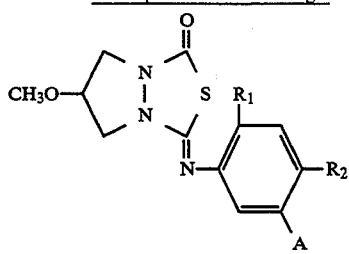

(Ig)

| Comp. No. | R₁ | R₂ | A | phys. data |
|---|---|---|---|---|
| 5.066 | F | Cl | —COOCH—COOCH₃<br>        |<br>       CH₃ | |
| 5.067 | F | Cl | —COOCH₂—COOC₅H₁₁ | |
| 5.068 | F | Cl | —COOCH₂—CH₂—Si(CH₃)₃ | |
| 5.069 | F | Cl | —COONa | |
| 5.070 | F | Cl | —COOCH₂—CH₂—O—N=C(CH₃)₂ | |
| 5.071 | F | Cl | —OH | |
| 5.072 | F | Cl | —OCH₃ | |
| 5.073 | F | Cl | —OC₂H₅ | |
| 5.074 | F | Cl | —OC₃H₇ | |
| 5.075 | F | Cl | —OCH(CH₃)₂ | oil |
| 5.076 | F | Cl | —OC₄H₉ | |
| 5.077 | F | Cl | —OCH(CH₃)—C₂H₅ | |
| 5.078 | F | Cl | —O—CH₂—CH(CH₃)₂ | |
| 5.079 | F | Cl | —OCH₂CH=CH₂ | |
| 5.080 | F | Cl | —OCH₂—C(Cl)=CH₂ | |
| 5.081 | F | Cl | —OCH₂CH=CHCl | |
| 5.082 | F | Cl | —OCH₂C≡CH | |
| 5.083 | F | Cl | —OCH(CH₃)—C≡CH | |
| 5.084 | F | Cl | —OCH₂—COOCH₃ | |
| 5.085 | F | Cl | —O—CH₂—COOC₅H₁₁ | |
| 5.086 | F | Cl | —O—CH(CH₃)—COOCH₃ | |
| 5.087 | F | Cl | —O—CH₂—COOC₂H₅ | |
| 5.088 | F | Cl | —O—CH(CH₃)—COOC₂H₅ | |
| 5.089 | F | Cl | —O—CH₂—CH₂—O—CH₃ | |

TABLE 5-continued

Compounds of formula Ig

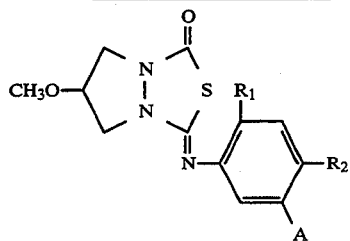
(Ig)

| Comp. No. | R$_1$ | R$_2$ | A | phys. data |
|---|---|---|---|---|
| 5.090 | F | Cl | —O—CH(CH$_3$)—CH$_2$—S—CH$_3$ | |
| 5.091 | F | Cl | —O—CH(CH$_3$)—CH$_2$—S—C$_2$H$_5$ | |
| 5.092 | F | Cl | —O—CH(CH$_3$)—CH$_2$—S—C$_3$H$_7$ | |
| 5.093 | F | Cl | —O—CH$_2$—CH$_2$—Cl | |
| 5.094 | F | Cl | —O—CH$_2$—CN | |
| 5.095 | F | Cl | —O—CH(CH$_3$)—CN | |
| 5.096 | F | Cl | —S—CH$_3$ | |
| 5.097 | F | Cl | —S—C$_2$H$_5$ | |
| 5.098 | F | Cl | —S—C$_3$H$_7$ | |
| 5.099 | F | Cl | —S—CH(CH$_3$)$_2$ | |
| 5.100 | F | Cl | —S—CH$_2$—CH=CH$_2$ | |
| 5.101 | F | Cl | —S—CH$_2$—C(Cl)=CH$_2$ | |
| 5.102 | F | Cl | —S—CH$_2$—CH=CHCl | |
| 5.103 | F | Cl | —S—CH$_2$—C≡CH | |
| 5.104 | F | Cl | —S—CH(CH$_3$)—C≡CH | |
| 5.105 | F | Cl | —S—CH$_2$—COOCH$_3$ | oil |
| 5.106 | F | Cl | —S—CH$_2$—COOC$_2$H$_5$ | |
| 5.107 | F | Cl | —S—CH$_2$—COOC$_5$H$_{11}$ | |
| 5.108 | F | Cl | —S—CH(CH$_3$)—COOCH$_3$ | |
| 5.109 | F | Cl | —S—CH(CH$_3$)—COOC$_2$H$_5$ | |
| 5.110 | F | Cl | —S—CH$_2$—COOCH$_2$—CH$_2$—O—CH$_3$ | |
| 5.111 | F | Cl | —O—CH$_2$—C$_6$H$_5$ | |

TABLE 5-continued
Compounds of formula Ig
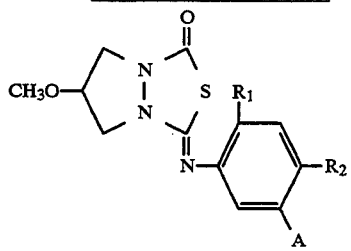
(Ig)
| Comp. No. | R₁ | R₂ | A | phys. data |
|---|---|---|---|---|
| 5.112 | F | Cl |  | |
| 5.113 | F | Cl |  | |
| 5.114 | F | Cl |  | |
| 5.115 | F | Cl |  | |
| 5.116 | F | Cl |  | |
| 5.117 | F | Cl |  | |
| 5.118 | F | Cl |  | |
| 5.119 | F | Cl |  | |
| 5.120 | F | Cl |  | |
| 5.121 | F | Cl | 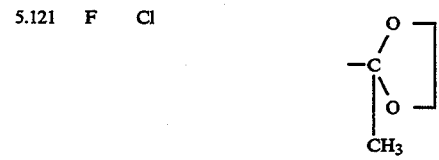 | |
| 5.122 | F | Cl | 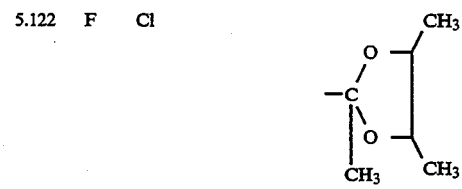 | |
| 5.123 | F | Cl |  | |

TABLE 5-continued

Compounds of formula Ig

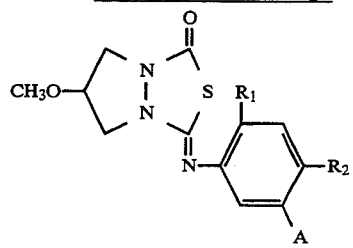

(Ig)

| Comp. No. | $R_1$ | $R_2$ | A | phys. data |
|---|---|---|---|---|
| 5.124 | F | Cl | —S—△—COOC$_2$H$_5$ | |
| 5.125 | F | Cl | —S—△—COOC$_3$H$_7$ | |
| 5.126 | F | Cl | —S—△—COOCH(CH$_3$)$_2$ | |
| 5.127 | F | Cl | —S—△—COO—CH$_2$—CH$_2$—Cl | |
| 5.128 | F | Cl | —S—△—COOC$_5$H$_{11}$ | |
| 5.129 | F | Cl | —S—△—COOCH$_2$—CH$_2$—O—CH$_3$ | |
| 5.130 | F | Cl | —S—△—COOCH(CH$_3$)—CH$_2$—S—CH$_3$ | |
| 5.131 | F | Cl | —S—△—COOCH(CH$_3$)—N(CH$_3$)$_2$ | |
| 5.132 | F | Cl | —S—△—COO—cyclopentyl | |
| 5.133 | F | Cl | —S—△—COO—cyclohexyl | |
| 5.134 | F | Cl | —S—△—COO—CH$_2$—CH$_2$—CH=CH$_2$ | |
| 5.135 | F | Cl | —S—△—COO—CH$_2$—C(Cl)=CH$_2$ | |
| 5.136 | F | Cl | —S—△—COO—CH$_2$—C≡CH | |
| 5.137 | F | Cl | —S—△—COOH | |

TABLE 5-continued
Compounds of formula Ig
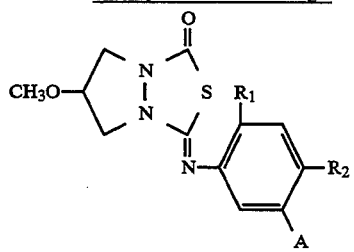
(Ig)
| Comp. No. | R₁ | R₂ | A | phys. data |
|---|---|---|---|---|
| 5.138 | F | Cl | —S—△—CONH₂ | |
| 5.139 | F | Cl | —S—△—CONH—CH₃ | |
| 5.140 | F | Cl | —S—△(CH₃)—COOC₂H₅ | |
| 5.141 | F | Cl | —S—△(C₂H₅)—COOC₂H₅ | |
| 5.142 | F | Cl | —S—△(F)—COOCH₃ | |
| 5.143 | F | Cl | —S—△(F)—COOC₂H₅ | |
| 5.144 | F | Cl | —S—△—COO—CH(CH₃)₂ | |
| 5.145 | F | Cl | —S—△—COO—cyclopentyl | |
| 5.146 | F | Cl | —NH—SO₂—CH₃ | |
| 5.147 | F | Cl | —NH—SO₂—C₂H₅ | |
| 5.148 | F | Cl | —NH—SO₂—Cl | |
| 5.149 | F | Cl | —NH—SO₂—△ | |
| 5.150 | F | Cl | —O—P(=O)(OC₂H₅)(OC₂H₅) | |
| 5.151 | H | Cl | —COOH | |
| 5.152 | H | Cl | —COOCH₃ | |
| 5.153 | H | Cl | —COO—CH(CH₃)₂ | resin |
| 5.154 | H | Cl | —COO—C₅H₁₁ | |

TABLE 5-continued

Compounds of formula Ig

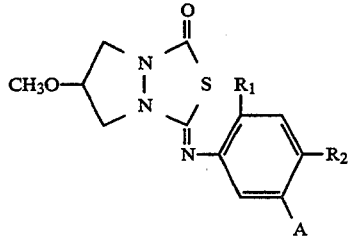

(Ig)

| Comp. No. | R₁ | R₂ | A | phys. data |
|---|---|---|---|---|
| 5.155 | H | Cl | —COO—CH₂—CH₂—O—CH₃ | |
| 5.156 | H | Cl | —COOCH₂—S—CH₃ | |
| 5.157 | H | Cl | —COOCH(CH₃)—CH₂—S—CH₃ | |
| 5.158 | H | Cl | —COO—CH(CH₃)—CH₂—N(CH₃)₂ | |
| 5.159 | H | Cl | —CO—N(CH₃)₂ | |
| 5.160 | H | Cl | —CO—N(morpholine) | |
| 5.161 | H | Cl | —COON=C(CH₃)₂ | |
| 5.162 | H | Cl | —COOCH₂—CH₂—O—N=C(CH₃)₂ | |
| 5.163 | H | Cl | —COO-cyclohexyl | |
| 5.164 | H | Cl | —CH(CH₃)-cyclopropyl | |
| 5.165 | H | Cl | —S—C₃H₇ | |
| 5.166 | H | Cl | —COOCH₂—COOCH₃ | |
| 5.167 | H | Cl | —COOCH(CH₃)—COOCH₃ | |
| 5.168 | H | Cl | —COS—CH₂—COOCH₃ | |
| 5.169 | H | Cl | —COS—CH(CH₃)—COOCH₃ | |
| 5.170 | H | Cl | —OH | |
| 5.171 | H | Cl | —OCH₃ | |
| 5.172 | H | Cl | —O—C₂H₅ | |
| 5.173 | H | Cl | —O—CH(CH₃)₂ | |
| 5.174 | H | Cl | —O—CH₂—C≡CH | |
| 5.175 | H | Cl | —O—CH₂—CH=CHCl | |
| 5.176 | H | Cl | —O—CH₂—C(Cl)=CH₂ | |

TABLE 5-continued

Compounds of formula Ig

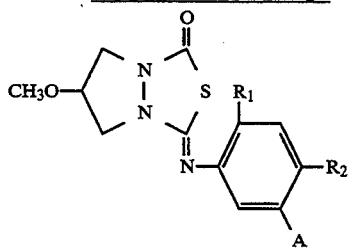

(Ig)

| Comp. No. | R₁ | R₂ | A | phys. data |
|---|---|---|---|---|
| 5.177 | H | Cl | —O—CH(CH₃)—C≡CH | |
| 5.178 | H | Cl | —O—CH₂—COOCH₃ | |
| 5.179 | H | Cl | —O—CH₂—COOC₂H₅ | |
| 5.180 | H | Cl | —O—CH(CH₃)—COOCH₃ | |
| 5.181 | H | Cl | —SH | |
| 5.182 | H | Cl | —SCH₃ | |
| 5.183 | H | Cl | —SC₂H₅ | |
| 5.184 | H | Cl | —S—CH(CH₃)₂ | |
| 5.185 | H | Cl | —S—CH₂—COOCH₃ | |
| 5.186 | H | Cl | —S—CH(CH₃)—COOCH₃ | |
| 5.187 | H | Cl | —S—CH₂—COOC₂H₅ | |
| 5.188 | H | Cl | —C(=N—OCH₃)—CN | |
| 5.189 | H | Cl | —C(OCH(CH₃))₂ (isopropylidenedioxy) | |
| 5.190 | H | Cl | —S—cyclopropyl-COOC₂H₅ | |
| 5.191 | H | Cl | —S—cyclopropyl-COOH | |
| 5.192 | H | Cl | —S—cyclopropyl-COO—CH(CH₃)₂ | |
| 5.193 | H | Cl | —S—cyclopropyl(CH₃)-COOC₂H₅ | |
| 5.194 | H | Cl | —S—cyclopropyl(F)-COOC₂H₅ | |
| 5.195 | H | Cl | —S—cyclopropyl(CF₃)-COOC₂H₅ | |

TABLE 5-continued

Compounds of formula Ig

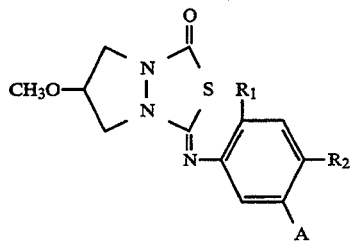

(Ig)

| Comp. No. | $R_1$ | $R_2$ | A | phys. data |
|---|---|---|---|---|
| 5.196 | H | Cl | -S-◁-COO-CH(CH$_3$)$_2$ with CF$_3$ on ring | |
| 5.197 | H | Cl | -S-◁-COOH | |
| 5.198 | H | Cl | -S-◁-COOH with CF$_3$ on ring | |
| 5.199 | H | Cl | -S-◁-COOC$_5$H$_{11}$ with CH$_3$ on ring | |
| 5.200 | H | Cl | -S-◁-COOC$_2$H$_5$ with C$_2$H$_5$ on ring | |
| 5.201 | H | Cl | -S-◁-COOC$_2$H$_5$ with CH(CH$_3$)$_2$ on ring | |
| 5.202 | H | Cl | —NH—SO$_2$—C$_2$H$_5$ | |
| 5.203 | H | Cl | —NH—SO$_2$—CH$_2$—Cl | |
| 5.204 | F | CN | —COOH | |
| 5.205 | F | CN | —COO—CH(CH$_3$)$_2$ | |
| 5.206 | F | CN | —O—CH(CH$_3$)$_2$ | |
| 5.207 | F | CN | —O—CH$_2$—C≡CH | |
| 5.208 | F | CN | —O—CH(CH$_3$)—C≡CH | |
| 5.209 | F | CN | —S—CH$_2$—COOCH$_3$ | |
| 5.210 | F | CN | —S—CH(CH$_3$)—COOCH$_3$ | |
| 5.211 | F | CN | —O—CH$_2$—COOCH$_3$ | |
| 5.212 | F | CN | —O—CH$_2$—COOC$_5$H$_{11}$ | |
| 5.213 | F | CN | —O—CH(CH$_3$)—COOC$_2$H$_5$ | |
| 5.214 | F | CN | -S-◁-COOCH$_3$ | |

TABLE 5-continued
Compounds of formula Ig
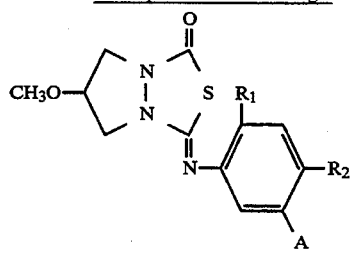
(Ig)
| Comp. No. | R₁ | R₂ | A | phys. data |
|---|---|---|---|---|
| 5.215 | F | CN | —S—△—COOC$_2$H$_5$ | |
| 5.216 | F | CN | —S—△—COOC$_2$H$_5$ (F) | |
| 5.217 | F | CN | —S—△—COOH | |
| 5.218 | F | CN | —S—△—COOH (F) | |
| 5.219 | F | CN | —S—△—COOH (CF$_3$) | |
| 5.220 | F | CN | —S—△—COOC$_2$H$_5$ | |
| 5.221 | F | Br | —COOH | |
| 5.222 | F | Br | —COO—CH(CH$_3$)$_2$ | |
| 5.223 | F | Br | —OH | |
| 5.224 | F | Br | —O—CH(CH$_3$)$_2$ | |
| 5.225 | F | Br | —O—CH$_2$—C≡CH | |
| 5.226 | F | Br | —O—CH(CH$_3$)—C≡CH | |
| 5.227 | F | Br | —O—CH$_2$COOCH$_3$ | |
| 5.228 | F | Br | —O—CH$_2$—COOC$_5$H$_{11}$ | |
| 5.229 | F | Br | —S—CH$_2$—COOCH$_3$ | |
| 5.230 | F | Br | —S—△—COOC$_2$H$_5$ | |
| 5.231 | F | Br | —S—△—COOH (F) | |
| 5.232 | F | Br | —S—△—COOC$_2$H$_5$ (F) | |

TABLE 5-continued

Compounds of formula Ig

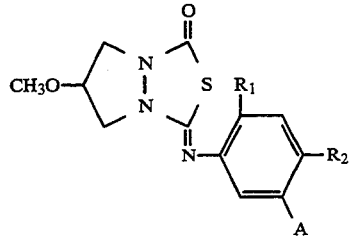
(Ig)

| Comp. No. | R₁ | R₂ | A | phys. data |
|---|---|---|---|---|
| 5.233 | F | Cl | —S—CH₂COOH | |

TABLE 6

Compounds of formula Ih

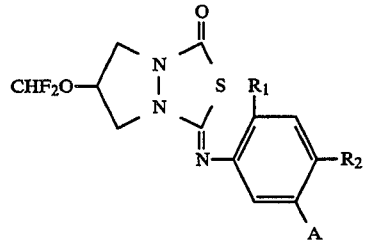
(Ih)

| Comp. No. | R₁ | R₂ | A | phys. data |
|---|---|---|---|---|
| 6.001 | F | Cl | —H | |
| 6.002 | F | Cl | —CN | |
| 6.003 | F | Cl | —NO₂ | |
| 6.004 | F | Cl | —COOH | |
| 6.005 | F | Cl | —COOCH₃ | |
| 6.006 | F | Cl | —COOC₂H₅ | |
| 6.007 | F | Cl | —COOC₃H₇ | |
| 6.008 | F | Cl | —COOCH(CH₃)₂ | |
| 6.009 | F | Cl | —COOC₄H₉ | |
| 6.010 | F | Cl | —COOCH(CH₃)—CH₂—CH₃ | |
| 6.011 | F | Cl | —COOCH₂—CH₂—CH(CH₃)₂ | |
| 6.012 | F | Cl | —COOC₅H₁₁ | |
| 6.013 | F | Cl | —COOCH₂—CH₂—O—CH₃ | |
| 6.014 | F | Cl | —COOCH₂—CH₂—O—C₂H₅ | |
| 6.015 | F | Cl | —COOCH(CH₃)—CH₂—OCH₃ | |
| 6.016 | F | Cl | —COOCH₂—CH₂—S—CH₃ | |
| 6.017 | F | Cl | —COOCH(CH₃)—CH₂—S—CH₃ | |
| 6.018 | F | Cl | —COOCH(CH₃)—CH₂—S—C₂H₅ | |
| 6.019 | F | Cl | —COOCH(CH₃)—CH₂—S—C₃H₇ | |
| 6.020 | F | Cl | —COOCH(CH₃)—CH₂—S—CH(CH₃)₂ | |
| 6.021 | F | Cl | —COOCH(CH₃)—CH₂—S—C₄H₉ | |
| 6.022 | F | Cl | —COOCH(CH₃)—CH₂—S—C₅H₁₁ | |
| 6.023 | F | Cl | —COOCH(CH₃)—CH₂—N(CH₃)₂ | |

TABLE 6-continued

Compounds of formula Ih

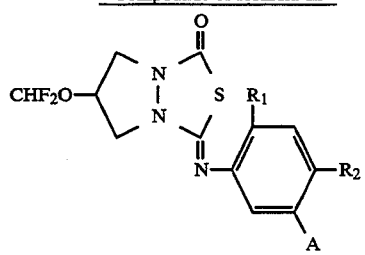

(Ih)

| Comp. No. | $R_1$ | $R_2$ | A | phys. data |
|---|---|---|---|---|
| 6.024 | F | Cl | —COOCH($CH_3$)—$CH_2$—N($C_2H_5$)($C_2H_5$) | |
| 6.025 | F | Cl | —CON$H_2$ | |
| 6.026 | F | Cl | —CONH—$CH_3$ | |
| 6.027 | F | Cl | —CON($CH_3$)($CH_3$) | |
| 6.028 | F | Cl | —CON($CH_3$)($C_4H_9$) | |
| 6.029 | F | Cl | —CON($CH_2$—$CH_2$—OH)($CH_2$—$CH_2$—OH) | |
| 6.030 | F | Cl | —CONH—$CH_2$—CH=$CH_2$ | |
| 6.031 | F | Cl | —CON($CH_2$—CH=$CH_2$)$_2$ | |
| 6.032 | F | Cl | —CON(pyrrolidinyl) | |
| 6.033 | F | Cl | —CON(piperidinyl) | |
| 6.034 | F | Cl | —CON(morpholinyl) | |
| 6.035 | F | Cl | —CON(thiomorpholinyl) | |
| 6.036 | F | Cl | —CON(N-methylpiperazinyl) | |
| 6.037 | F | Cl | —COON=C($CH_3$)($CH_3$) | |
| 6.038 | F | Cl | —COOC$H_2$—$CH_2$—Cl | |

TABLE 6-continued
Compounds of formula Ih
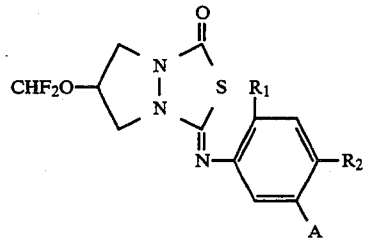
(Ih)
| Comp. No. | $R_1$ | $R_2$ | A | phys. data |
|---|---|---|---|---|
| 6.039 | F | Cl | —COOCH$_2$—CN | |
| 6.040 | F | Cl | —COOCH(CN)CH$_3$ | |
| 6.041 | F | Cl | —COOCH$_2$—CH=CH$_2$ | |
| 6.042 | F | Cl | —COOCH$_2$—CH=CHCl | |
| 6.043 | F | Cl | —COOCH$_2$—C(Cl)=CH$_2$ | |
| 6.044 | F | Cl | —COOCH$_2$—C≡CH | |
| 6.045 | F | Cl | —COO—CH(CH$_3$)—C≡CH | |
| 6.046 | F | Cl | —COO-cyclopentyl | |
| 6.047 | F | Cl | —COO-cyclohexyl | |
| 6.048 | F | Cl | —COOCH$_2$-cyclopentyl | |
| 6.049 | F | Cl | —COOCH(CH$_3$)-cyclopropyl | |
| 6.050 | F | Cl | —COOCH$_2$-phenyl | |
| 6.051 | F | Cl | —COOCH$_2$-(2-Cl-phenyl) | |
| 6.052 | F | Cl | —COOCH$_2$-(4-CH$_3$-phenyl) | |

TABLE 6-continued

Compounds of formula Ih (Ih) Structure: CHF$_2$O-substituted pyrazolidinone fused with thiadiazole, with N=substituted phenyl bearing R$_1$, R$_2$, and A.

| Comp. No. | R$_1$ | R$_2$ | A | phys. data |
|---|---|---|---|---|
| 6.053 | F | Cl | —COSCH$_3$ | |
| 6.054 | F | Cl | —COSC$_2$H$_5$ | |
| 6.055 | F | Cl | —COSC$_3$H$_7$ | |
| 6.056 | F | Cl | —COS—CH$_2$—CH=CH$_2$ | |
| 6.057 | F | Cl | —COS—CH$_2$—COOCH$_3$ | |
| 6.058 | F | Cl | —COS—CH$_2$—COOC$_2$H$_5$ | |
| 6.059 | F | Cl | —COS—CH$_2$—COOC$_5$H$_{11}$ | |
| 6.060 | F | Cl | —COS—CH(CH$_3$)—COOCH$_3$ | |
| 6.061 | F | Cl | —COS—CH(CH$_3$)—COOC$_2$H$_5$ | |
| 6.062 | F | Cl | —COS—CH(CH$_3$)—COOC$_3$H$_7$ | |
| 6.063 | F | Cl | —COS—CH$_2$—CH$_2$—COOCH$_3$ | |
| 6.064 | F | Cl | —COS—CH$_2$—COOCH$_2$—CH$_2$—O—CH$_3$ | |
| 6.065 | F | Cl | —COOCH$_2$—COOCH$_3$ | |
| 6.066 | F | Cl | —COOCH(CH$_3$)—COOCH$_3$ | |
| 6.067 | F | Cl | —COOCH$_2$—COOC$_5$H$_{11}$ | |
| 6.068 | F | Cl | —COOCH$_2$—CH$_2$—Si(CH$_3$)$_3$ | |
| 6.069 | F | Cl | —COONa | |
| 6.070 | F | Cl | —COOCH$_2$—CH$_2$—O—N=C(CH$_3$)$_2$ | |
| 6.071 | F | Cl | —OH | |
| 6.072 | F | Cl | —OCH$_3$ | |
| 6.073 | F | Cl | —OC$_2$H$_5$ | |
| 6.074 | F | Cl | —OC$_3$H$_7$ | |
| 6.075 | F | Cl | —OCH(CH$_3$)$_2$ | resin |
| 6.076 | F | Cl | —OC$_4$H$_9$ | |
| 6.077 | F | Cl | —OCH(CH$_3$)—C$_2$H$_5$ | |
| 6.078 | F | Cl | —O—CH$_2$—CH(CH$_3$)$_2$ | |
| 6.079 | F | Cl | —OCH$_2$CH=CH$_2$ | |

TABLE 6-continued

Compounds of formula Ih

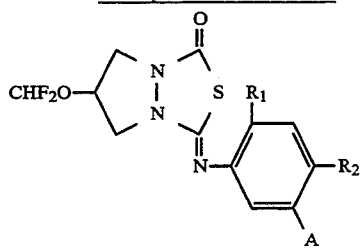

(Ih)

| Comp. No. | $R_1$ | $R_2$ | A | phys. data |
|---|---|---|---|---|
| 6.080 | F | Cl | —OCH$_2$—C(Cl)=CH$_2$ | |
| 6.081 | F | Cl | —OCH$_2$CH=CHCl | |
| 6.082 | F | Cl | —OCH$_2$C≡CH | |
| 6.083 | F | Cl | —OCH(CH$_3$)—C≡CH | |
| 6.084 | F | Cl | —OCH$_2$—COOCH$_3$ | |
| 6.085 | F | Cl | —O—CH$_2$—COOC$_5$H$_{11}$ | |
| 6.086 | F | Cl | —O—CH(CH$_3$)—COOCH$_3$ | |
| 6.087 | F | Cl | —O—CH$_2$—COOC$_2$H$_5$ | |
| 6.088 | F | Cl | —O—CH(CH$_3$)—COOC$_2$H$_5$ | |
| 6.089 | F | Cl | —O—CH$_2$—CH$_2$—O—CH$_3$ | |
| 6.090 | F | Cl | —O—CH(CH$_3$)—CH$_2$—S—CH$_3$ | |
| 6.091 | F | Cl | —O—CH(CH$_3$)—CH$_2$—S—C$_2$H$_5$ | |
| 6.092 | F | Cl | —O—CH(CH$_3$)—CH$_2$—S—C$_3$H$_7$ | |
| 6.093 | F | Cl | —O—CH$_2$—CH$_2$—Cl | |
| 6.094 | F | Cl | —O—CH$_2$—CN | |
| 6.095 | F | Cl | —O—CH(CH$_3$)—CN | |
| 6.096 | F | Cl | —S—CH$_3$ | |
| 6.097 | F | Cl | —S—C$_2$H$_5$ | |
| 6.098 | F | Cl | —S—C$_3$H$_7$ | |
| 6.099 | F | Cl | —S—CH(CH$_3$)$_2$ | |
| 6.100 | F | Cl | S—CH$_2$—CH=CH$_2$ | |
| 6.101 | F | Cl | —S—CH$_2$—C(Cl)=CH$_2$ | |
| 6.102 | F | Cl | —S—CH$_2$—CH=CHCl | |
| 6.103 | F | Cl | —S—CH$_2$—C≡CH | |

TABLE 6-continued

Compounds of formula Ih (Ih)

| Comp. No. | R₁ | R₂ | A | phys. data |
|---|---|---|---|---|
| 6.104 | F | Cl | —S—CH(CH₃)—C≡CH | |
| 6.105 | F | Cl | —S—CH₂—COOCH₃ | |
| 6.106 | F | Cl | —S—CH₂—COOC₂H₅ | |
| 6.107 | F | Cl | —S—CH₂—COOC₅H₁₁ | |
| 6.108 | F | Cl | —S—CH(CH₃)—COOCH₃ | |
| 6.109 | F | Cl | —S—CH(CH₃)—COOC₂H₅ | |
| 6.110 | F | Cl | —S—CH₂—COOCH₂—CH₂—O—CH₃ | |
| 6.111 | F | Cl | —O—CH₂—C₆H₅ | |
| 6.112 | F | Cl | —S—CH₂—C₆H₅ | |
| 6.113 | F | Cl | —C(CN)=N—O—CH₃ | |
| 6.114 | F | Cl | —C(CN)=N—O—CH₂—COOCH₃ | |
| 6.115 | F | Cl | —C(CN)=N—O—CH₂—C≡CH | |
| 6.116 | F | Cl | —C(CH₃)=N—O—CH₃ | |
| 6.117 | F | Cl | —C(CH₃)=N—O—CH₂—C≡CH | |
| 6.118 | F | Cl | —N(CH₂—O—CH₃)=N—O—CH₃ | |
| 6.119 | F | Cl | —C(CH₃)(O—CH₃)(O—CH₃) | |

TABLE 6-continued
Compounds of formula Ih
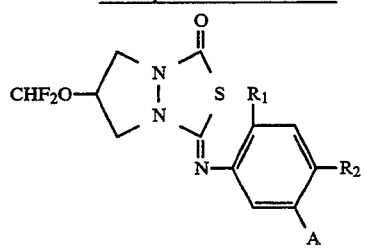
(Ih)
| Comp. No. | R$_1$ | R$_2$ | A | phys. data |
|---|---|---|---|---|
| 6.120 | F | Cl |  | |
| 6.121 | F | Cl | 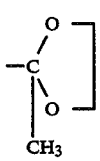 | |
| 6.122 | F | Cl | 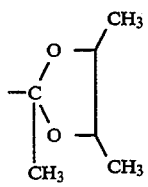 | |
| 6.123 | F | Cl |  | |
| 6.124 | F | Cl | 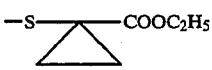 | |
| 6.125 | F | Cl | 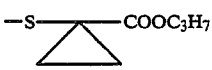 | |
| 6.126 | F | Cl | 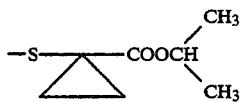 | |
| 6.127 | F | Cl | 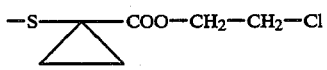 | |
| 6.128 | F | Cl | 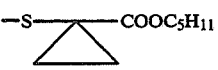 | |
| 6.129 | F | Cl | 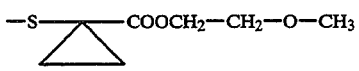 | |
| 6.130 | F | Cl |  | |
| 6.131 | F | Cl |  | |

TABLE 6-continued
Compounds of formula Ih
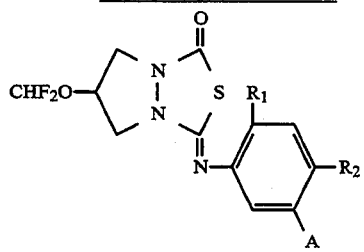
(Ih)
| Comp. No. | R₁ | R₂ | A | phys. data |
|---|---|---|---|---|
| 6.132 | F | Cl | —S—◁—COO—⬠ | |
| 6.133 | F | Cl | —S—◁—COO—⬡ | |
| 6.134 | F | Cl | —S—◁—COO—CH₂—CH₂—CH=CH₂ | |
| 6.135 | F | Cl | —S—◁—COO—CH₂—C(Cl)=CH₂ | |
| 6.136 | F | Cl | —S—◁—COO—CH₂—C≡CH | |
| 6.137 | F | Cl | —S—◁—COOH | |
| 6.138 | F | Cl | —S—◁—CONH₂ | |
| 6.139 | F | Cl | —S—◁—CONH—CH₃ | |
| 6.140 | F | Cl | —S—◁(CH₃)—COOC₂H₅ | |
| 6.141 | F | Cl | —S—◁(C₂H₅)—COOC₂H₅ | |
| 6.142 | F | Cl | —S—◁(F)—COOCH₃ | |
| 6.143 | F | Cl | —S—◁(F)—COOC₂H₅ | |
| 6.144 | F | Cl | —S—◁—COO—CH(CH₃)₂ | |

TABLE 6-continued

Compounds of formula Ih

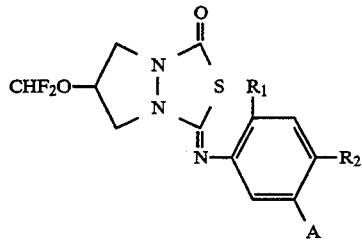

(Ih)

| Comp. No. | $R_1$ | $R_2$ | A | phys. data |
|---|---|---|---|---|
| 6.145 | F | Cl | —S—⟨△⟩—COO—⟨cyclopentyl⟩ | |
| 6.146 | F | Cl | —NH—SO$_2$—CH$_3$ | |
| 6.147 | F | Cl | —NH—SO$_2$—C$_2$H$_5$ | |
| 6.148 | F | Cl | —NH—SO$_2$—Cl | |
| 6.149 | F | Cl | —NH—SO$_2$—⟨△⟩ | |
| 6.150 | F | Cl | —O—P(=O)(OC$_2$H$_5$)(OC$_2$H$_5$) | |
| 6.151 | H | Cl | —COOH | |
| 6.152 | H | Cl | —COOCH$_3$ | |
| 6.153 | H | Cl | —COO—CH(CH$_3$)$_2$ | |
| 6.154 | H | Cl | —COO—C$_5$H$_{11}$ | |
| 6.155 | H | Cl | —COO—CH$_2$—CH$_2$—O—CH$_3$ | |
| 6.156 | H | Cl | —COOCH$_2$—S—CH$_3$ | |
| 6.157 | H | Cl | —COOCH(CH$_3$)—CH$_2$—S—CH$_3$ | |
| 6.158 | H | Cl | —COO—CH(CH$_3$)—CH$_2$—N(CH$_3$)$_2$ | |
| 6.159 | H | Cl | —CO—N(CH$_3$)$_2$ | |
| 6.160 | H | Cl | —CO—N⟨morpholino⟩O | |
| 6.161 | H | Cl | —COON=C(CH$_3$)(CH$_3$) | |
| 6.162 | H | Cl | —COOCH$_2$—CH$_2$—O—N=C(CH$_3$)(CH$_3$) | |

TABLE 6-continued

Compounds of formula Ih

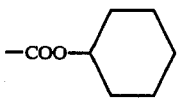

| Comp. No. | R₁ | R₂ | A | phys. data |
|---|---|---|---|---|
| 6.163 | H | Cl | —COO—$C_6H_{11}$ (cyclohexyl) | |
| 6.164 | H | Cl | —CH(CH₃)—cyclopropyl | |
| 6.165 | H | Cl | —S—C₃H₇ | |
| 6.166 | H | Cl | —COOCH₂—COOCH₃ | |
| 6.167 | H | Cl | —COOCH(CH₃)—COOCH₃ | |
| 6.168 | H | Cl | —COS—CH₂—COOCH₃ | |
| 6.169 | H | Cl | —COS—CH(CH₃)—COOCH₃ | |
| 6.170 | H | Cl | —OH | |
| 6.171 | H | Cl | —OCH₃ | |
| 6.172 | H | Cl | —O—C₂H₅ | |
| 6.173 | H | Cl | —O—CH(CH₃)₂ | |
| 6.174 | H | Cl | —O—CH₂—C≡CH | |
| 6.175 | H | Cl | —O—CH₂—CH=CHCl | |
| 6.176 | H | Cl | —O—CH₂—C(Cl)=CH₂ | |
| 6.177 | H | Cl | —O—CH(CH₃)—C≡CH | |
| 6.178 | H | Cl | —O—CH₂—COOCH₃ | |
| 6.179 | H | Cl | —O—CH₂—COOC₂H₅ | |
| 6.180 | H | Cl | —O—CH(CH₃)—COOCH₃ | |
| 6.181 | H | Cl | —SH | |
| 6.182 | H | Cl | —SCH₃ | |
| 6.183 | H | Cl | —SC₂H₅ | |
| 6.184 | H | Cl | —S—CH(CH₃)₂ | |
| 6.185 | H | Cl | —S—CH₂—COOCH₃ | |
| 6.186 | H | Cl | —S—CH(CH₃)—COOCH₃ | |
| 6.187 | H | Cl | —S—CH₂—COOC₂H₅ | |
| 6.188 | H | Cl | —C(=N—OCH₃)—CN | |

TABLE 6-continued

Compounds of formula Ih

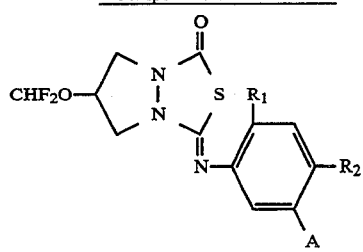

(Ih)

| Comp. No. | $R_1$ | $R_2$ | A | phys. data |
|---|---|---|---|---|
| 6.189 | H | Cl | -C(O-CH(CH₃))₂ with CH₃ (orthoester-like structure) | |
| 6.190 | H | Cl | -S-cyclopropyl-COOC₂H₅ | |
| 6.191 | H | Cl | -S-cyclopropyl-COOH | |
| 6.192 | H | Cl | -S-cyclopropyl-COO-CH(CH₃)₂ | |
| 6.193 | H | Cl | -S-cyclopropyl(CH₃)-COOC₂H₅ | |
| 6.194 | H | Cl | -S-cyclopropyl(F)-COOC₂H₅ | |
| 6.195 | H | Cl | -S-cyclopropyl(CF₃)-COOC₂H₅ | |
| 6.196 | H | Cl | -S-cyclopropyl(CF₃)-COO-CH(CH₃)₂ | |
| 6.197 | H | Cl | -S-cyclopropyl-COOH | |
| 6.198 | H | Cl | -S-cyclopropyl(CF₃)-COOH | |
| 6.199 | H | Cl | -S-cyclopropyl(CH₃)-COOC₅H₁₁ | |

TABLE 6-continued

Compounds of formula Ih

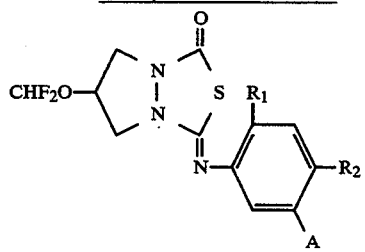
(Ih)

| Comp. No. | $R_1$ | $R_2$ | A | phys. data |
|---|---|---|---|---|
| 6.200 | H | Cl | —S—⟨△⟩(COOC$_2$H$_5$)(C$_2$H$_5$) | |
| 6.201 | H | Cl | —S—⟨△⟩(COOC$_2$H$_5$)(CH(CH$_3$)$_2$) | |
| 6.202 | H | Cl | —NH—SO$_2$—C$_2$H$_5$ | |
| 6.203 | H | Cl | —NH—SO$_2$—CH$_2$—Cl | |
| 6.204 | F | CN | —COOH | |
| 6.205 | F | CN | —COO—CH(CH$_3$)$_2$ | |
| 6.206 | F | CN | —O—CH(CH$_3$)$_2$ | |
| 6.207 | F | CN | —O—CH$_2$—C≡CH | |
| 6.208 | F | CN | —O—CH(CH$_3$)—C≡CH | |
| 6.209 | F | CN | —S—CH$_2$—COOCH$_3$ | |
| 6.210 | F | CN | —S—CH(CH$_3$)—COOCH$_3$ | |
| 6.211 | F | CN | —O—CH$_2$—COOCH$_3$ | |
| 6.212 | F | CN | —O—CH$_2$—COOC$_5$H$_{11}$ | |
| 6.213 | F | CN | —O—CH(CH$_3$)—COOC$_2$H$_5$ | |
| 6.214 | F | CN | —S—⟨△⟩—COOCH$_3$ | |
| 6.215 | F | CN | —S—⟨△⟩—COOC$_2$H$_5$ | |
| 6.216 | F | CN | —S—⟨△⟩(COOC$_2$H$_5$)(F) | |
| 6.217 | F | CN | —S—⟨△⟩—COOH | |
| 6.218 | F | CN | —S—⟨△⟩(COOH)(F) | |
| 6.219 | F | CN | —S—⟨△⟩(COOH)(CF$_3$) | |

TABLE 6-continued
Compounds of formula Ih

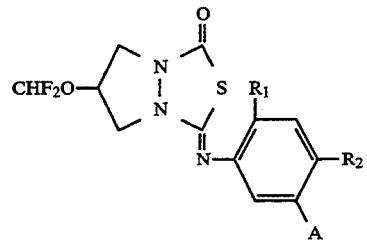

(Ih)

| Comp. No. | $R_1$ | $R_2$ | A | phys. data |
|---|---|---|---|---|
| 6.220 | F | CN | —S—⟨△⟩—COOC$_2$H$_5$ | |
| 6.221 | F | Br | —COOH | |
| 6.222 | F | Br | —COO—CH(CH$_3$)$_2$ | |
| 6.223 | F | Br | —OH | |
| 6.224 | F | Br | —O—CH(CH$_3$)$_2$ | |
| 6.225 | F | Br | —O—CH$_2$—C≡CH | |
| 6.226 | F | Br | —O—CH(CH$_3$)—C≡CH | |
| 6.227 | F | Br | —O—CH$_2$COOCH$_3$ | |
| 6.228 | F | Br | —O—CH$_2$—COOC$_5$H$_{11}$ | |
| 6.229 | F | Br | —S—CH$_2$—COOCH$_3$ | |
| 6.230 | F | Br | —S—⟨△⟩—COOC$_2$H$_5$ | |
| 6.231 | F | Br | —S—⟨△(F)⟩—COOH | |
| 6.232 | F | Br | —S—⟨△(F)⟩—COOC$_2$H$_5$ | |
| 6.233 | F | Cl | —S—CH$_2$COOH | |

TABLE 7
Compounds of formula Ii

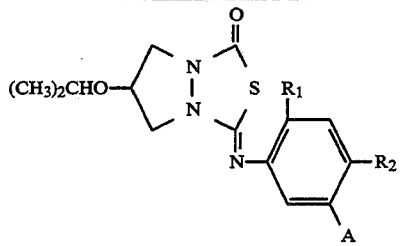

(Ii)

| Comp. No. | $R_1$ | $R_2$ | A | phys. data |
|---|---|---|---|---|
| 7.001 | F | Cl | —H | |
| 7.002 | F | Cl | —CN | |
| 7.003 | F | Cl | —NO$_2$ | |
| 7.004 | F | Cl | —COOH | |
| 7.005 | F | Cl | —COOCH$_3$ | |

TABLE 7-continued

Compounds of formula Ii

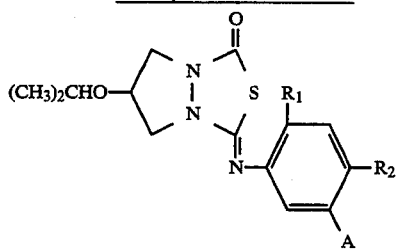

(Ii)

| Comp. No. | $R_1$ | $R_2$ | A | phys. data |
|---|---|---|---|---|
| 7.006 | F | Cl | —COOC$_2$H$_5$ | |
| 7.007 | F | Cl | —COOC$_3$H$_7$ | |
| 7.008 | F | Cl | —COOCH(CH$_3$)$_2$ | |
| 7.009 | F | Cl | —COOC$_4$H$_9$ | |
| 7.010 | F | Cl | —COOCH(CH$_3$)—CH$_2$—CH$_3$ | |
| 7.011 | F | Cl | —COOCH$_2$—CH$_2$—CH(CH$_3$)$_2$ | |
| 7.012 | F | Cl | —COOC$_5$H$_{11}$ | |
| 7.013 | F | Cl | —COOCH$_2$—CH$_2$—O—CH$_3$ | |
| 7.014 | F | Cl | —COOCH$_2$—CH$_2$—O—C$_2$H$_5$ | |
| 7.015 | F | Cl | —COOCH(CH$_3$)—CH$_2$—OCH$_3$ | |
| 7.016 | F | Cl | —COOCH$_2$—CH$_2$—S—CH$_3$ | |
| 7.017 | F | Cl | —COOCH(CH$_3$)—CH$_2$—S—CH$_3$ | |
| 7.018 | F | Cl | —COOCH(CH$_3$)—CH$_2$—S—C$_2$H$_5$ | |
| 7.019 | F | Cl | —COOCH(CH$_3$)—CH$_2$—S—C$_3$H$_7$ | |
| 7.020 | F | Cl | —COOCH(CH$_3$)—CH$_2$—S—CH(CH$_3$)$_2$ | |
| 7.021 | F | Cl | —COOCH(CH$_3$)—CH$_2$—S—C$_4$H$_9$ | |
| 7.022 | F | Cl | —COOCH(CH$_3$)—CH$_2$—S—C$_5$H$_{11}$ | |
| 7.023 | F | Cl | —COOCH(CH$_3$)—CH$_2$—N(CH$_3$)$_2$ | |
| 7.024 | F | Cl | —COOCH(CH$_3$)—CH$_2$—N(C$_2$H$_5$)$_2$ | |
| 7.025 | F | Cl | —CONH$_2$ | |
| 7.026 | F | Cl | —CONH—CH$_3$ | |
| 7.027 | F | Cl | —CON(CH$_3$)$_2$ | |
| 7.028 | F | Cl | —CON(CH$_3$)(C$_4$H$_9$) | |
| 7.029 | F | Cl | —CON(CH$_2$—CH$_2$—OH)$_2$ | |
| 7.030 | F | Cl | —CONH—CH$_2$—CH=CH$_2$ | |
| 7.031 | F | Cl | —CON(CH$_2$—CH=CH$_2$)$_2$ | |

TABLE 7-continued
Compounds of formula Ii
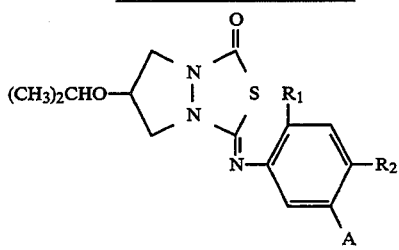
(Ii)
| Comp. No. | R₁ | R₂ | A | phys. data |
|---|---|---|---|---|
| 7.032 | F | Cl | 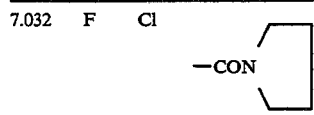 | |
| 7.033 | F | Cl | 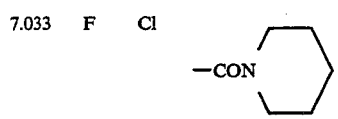 | |
| 7.034 | F | Cl | 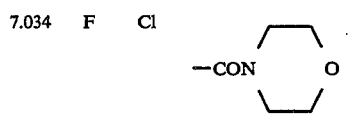 | |
| 7.035 | F | Cl | 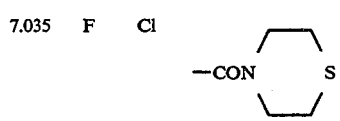 | |
| 7.036 | F | Cl | 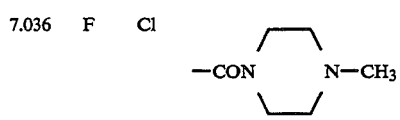 | |
| 7.037 | F | Cl | 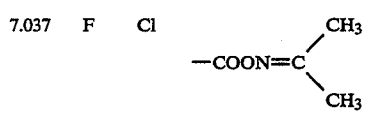 | |
| 7.038 | F | Cl | —COOCH₂—CH₂—Cl | |
| 7.039 | F | Cl | —COOCH₂—CN | |
| 7.040 | F | Cl | 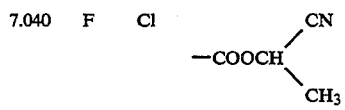 | |
| 7.041 | F | Cl | —COOCH₂—CH=CH₂ | |
| 7.042 | F | Cl | —COOCH₂—CH=CHCl | |
| 7.043 | F | Cl | 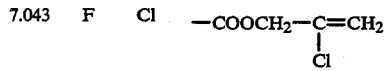 | |
| 7.044 | F | Cl | —COOCH₂—C≡CH | |
| 7.045 | F | Cl | 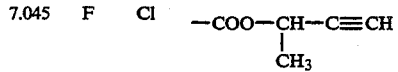 | |
| 7.046 | F | Cl | 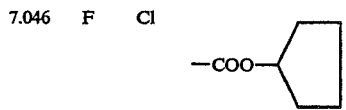 | |

TABLE 7-continued

Compounds of formula Ii

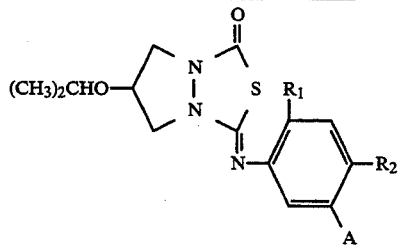
(Ii)

| Comp. No. | $R_1$ | $R_2$ | A | phys. data |
|---|---|---|---|---|
| 7.047 | F | Cl | —COO—C₆H₁₁ (cyclohexyl) | |
| 7.048 | F | Cl | —COOCH₂—(cyclopentyl) | |
| 7.049 | F | Cl | —COOCH(CH₃)—(cyclopropyl) | |
| 7.050 | F | Cl | —COOCH₂—phenyl | |
| 7.051 | F | Cl | —COOCH₂—(2-Cl-phenyl) | |
| 7.052 | F | Cl | —COOCH₂—(4-CH₃-phenyl) | |
| 7.053 | F | Cl | —COSCH₃ | |
| 7.054 | F | Cl | —COSC₂H₅ | |
| 7.055 | F | Cl | —COSC₃H₇ | |
| 7.056 | F | Cl | —COS—CH₂—CH=CH₂ | |
| 7.057 | F | Cl | —COS—CH₂—COOCH₃ | |
| 7.058 | F | Cl | —COS—CH₂—COOC₂H₅ | |
| 7.059 | F | Cl | —COS—CH₂—COOC₅H₁₁ | |
| 7.060 | F | Cl | —COS—CH(CH₃)—COOCH₃ | |
| 7.061 | F | Cl | —COS—CH(CH₃)—COOC₂H₅ | |
| 7.062 | F | Cl | —COS—CH(CH₃)—COOC₃H₇ | |
| 7.063 | F | Cl | —COS—CH₂—CH₂—COOCH₃ | |
| 7.064 | F | Cl | —COS—CH₂—COOCH₂—CH₂—O—CH₃ | |
| 7.065 | F | Cl | —COOCH₂—COOCH₃ | |
| 7.066 | F | Cl | —COOCH(CH₃)—COOCH | |

TABLE 7-continued

Compounds of formula Ii

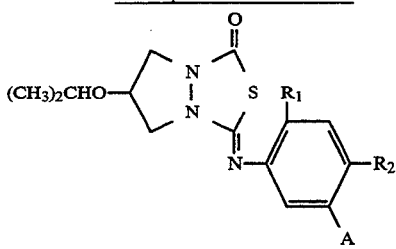

(Ii)

| Comp. No. | $R_1$ | $R_2$ | A | phys. data |
|---|---|---|---|---|
| 7.067 | F | Cl | —COOCH$_2$—COOC$_5$H$_{11}$ | |
| 7.068 | F | Cl | —COOCH$_2$—CH$_2$—Si(CH$_3$)$_3$ | |
| 7.069 | F | Cl | —COONa | |
| 7.070 | F | Cl | —COOCH$_2$—CH$_2$—O—N=C(CH$_3$)$_2$ | |
| 7.071 | F | Cl | —OH | |
| 7.072 | F | Cl | —OCH$_3$ | |
| 7.073 | F | Cl | —OC$_2$H$_5$ | |
| 7.074 | F | Cl | —OC$_3$H$_7$ | |
| 7.075 | F | Cl | —OCH(CH$_3$)$_2$ | |
| 7.076 | F | Cl | —OC$_4$H$_9$ | |
| 7.077 | F | Cl | —OCH(CH$_3$)—C$_2$H$_5$ | |
| 7.078 | F | Cl | —O—CH$_2$—CH(CH$_3$)$_2$ | |
| 7.079 | F | Cl | —OCH$_2$CH=CH$_2$ | |
| 7.080 | F | Cl | —OCH$_2$—C(Cl)=CH$_2$ | |
| 7.081 | F | Cl | —OCH$_2$CH=CHCl | |
| 7.082 | F | Cl | —OCH$_2$C≡CH | |
| 7.083 | F | Cl | —OCH(CH$_3$)—C≡CH | |
| 7.084 | F | Cl | —OCH$_2$—COOCH$_3$ | |
| 7.085 | F | Cl | —O—CH$_2$—COOC$_5$H$_{11}$ | |
| 7.086 | F | Cl | —O—CH(CH$_3$)—COOCH$_3$ | |
| 7.087 | F | Cl | —O—CH$_2$—COOC$_2$H$_5$ | |
| 7.088 | F | Cl | —O—CH(CH$_3$)—COOC$_2$H$_5$ | |
| 7.089 | F | Cl | —O—CH$_2$—CH$_2$—O—CH$_3$ | |
| 7.090 | F | Cl | —O—CH(CH$_3$)—CH$_2$—S—CH$_3$ | |

TABLE 7-continued

Compounds of formula Ii

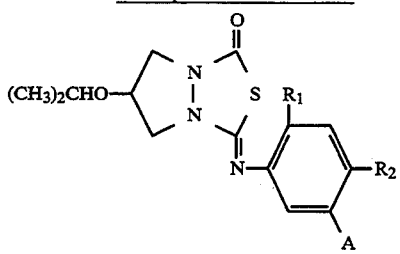

(Ii)

| Comp. No. | R₁ | R₂ | A | phys. data |
|---|---|---|---|---|
| 7.091 | F | Cl | —O—CH(CH₃)—CH₂—S—C₂H₅ | |
| 7.092 | F | Cl | —O—CH(CH₃)—CH₂—S—C₃H₇ | |
| 7.093 | F | Cl | —O—CH₂—CH₂—Cl | |
| 7.094 | F | Cl | —O—CH₂—CN | |
| 7.095 | F | Cl | —O—CH(CH₃)—CN | |
| 7.096 | F | Cl | —S—CH₃ | |
| 7.097 | F | Cl | —S—C₂H₅ | |
| 7.098 | F | Cl | —S—C₃H₇ | |
| 7.099 | F | Cl | —S—CH(CH₃)₂ | |
| 7.100 | F | Cl | —S—CH₂—CH=CH₂ | |
| 7.101 | F | Cl | —S—CH₂—C(Cl)=CH₂ | |
| 7.102 | F | Cl | —S—CH₂—CH=CHCl | |
| 7.103 | F | Cl | —S—CH₂—C≡CH | |
| 7.104 | F | Cl | —S—CH(CH₃)—C≡CH | |
| 7.105 | F | Cl | —S—CH₂—COOCH₃ | |
| 7.106 | F | Cl | —S—CH₂—COOC₂H₅ | |
| 7.107 | F | Cl | —S—CH₂—COOC₅H₁₁ | |
| 7.108 | F | Cl | —S—CH(CH₃)—COOCH₃ | |
| 7.109 | F | Cl | —S—CH(CH₃)—COOC₂H₅ | |
| 7.110 | F | Cl | —S—CH₂—COOCH₂—CH₂—O—CH₃ | |
| 7.111 | F | Cl | 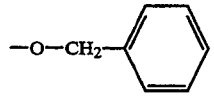 | |
| 7.112 | F | Cl | 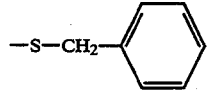 | |

TABLE 7-continued

Compounds of formula Ii

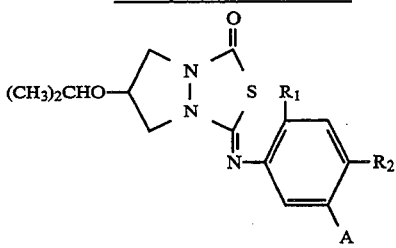

(Ii)

| Comp. No. | $R_1$ | $R_2$ | A | phys. data |
|---|---|---|---|---|
| 7.113 | F | Cl | —C(=N—O—CH$_3$)—CN | |
| 7.114 | F | Cl | —C(=N—O—CH$_2$—COOCH$_3$)—CN | |
| 7.115 | F | Cl | —C(=N—O—CH$_2$—C≡CH)—CN | |
| 7.116 | F | Cl | —C(=N—O—CH$_3$)—CH$_3$ | |
| 7.117 | F | Cl | —C(=N—O—CH$_2$—C≡CH)—CH$_3$ | |
| 7.118 | F | Cl | —C(=N—O—CH$_3$)—CH$_2$—O—CH$_3$ | |
| 7.119 | F | Cl | —C(CH$_3$)(O—CH$_3$)(O—CH$_3$) | |
| 7.120 | F | Cl | —C(CH$_3$)(O—C$_2$H$_5$)(O—C$_2$H$_5$) | |
| 7.121 | F | Cl | —C(CH$_3$)(OCH$_2$CH$_2$O) [1,3-dioxolane] | |
| 7.122 | F | Cl | —C(CH$_3$)(OCH(CH$_3$)CH(CH$_3$)O) | |
| 7.123 | F | Cl | —S—(cyclopropyl)—COOCH$_3$ | |
| 7.124 | F | Cl | —S—(cyclopropyl)—COOC$_2$H$_5$ | |
| 7.125 | F | Cl | —S—(cyclopropyl)—COOC$_3$H$_7$ | |

TABLE 7-continued

Compounds of formula Ii

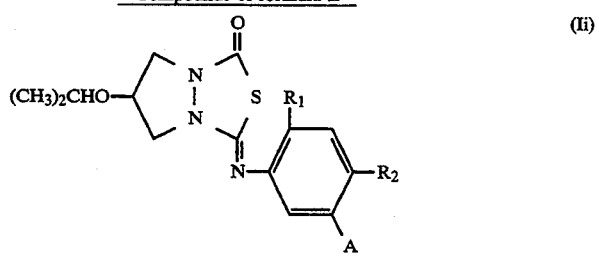
(Ii)

| Comp. No. | R₁ | R₂ | A | phys. data |
|---|---|---|---|---|
| 7.126 | F | Cl | −S−△−COOCH(CH₃)₂ | |
| 7.127 | F | Cl | −S−△−COO−CH₂−CH₂−Cl | |
| 7.128 | F | Cl | −S−△−COOC₅H₁₁ | |
| 7.129 | F | Cl | −S−△−COOCH₂−CH₂−O−CH₃ | |
| 7.130 | F | Cl | −S−△−COOCH(CH₃)−CH₂−S−CH₃ | |
| 7.131 | F | Cl | −S−△−COOCH(CH₃)−N(CH₃)₂ | |
| 7.132 | F | Cl | −S−△−COO−cyclopentyl | |
| 7.133 | F | Cl | −S−△−COO−cyclohexyl | |
| 7.134 | F | Cl | −S−△−COO−CH₂−CH₂−CH=CH₂ | |
| 7.135 | F | Cl | −S−△−COO−CH₂−C(Cl)=CH₂ | |
| 7.136 | F | Cl | −S−△−COO−CH₂−C≡CH | |
| 7.137 | F | Cl | −S−△−COOH | |
| 7.138 | F | Cl | −S−△−CONH₂ | |
| 7.139 | F | Cl | −S−△−CONH−CH₃ | |

TABLE 7-continued

Compounds of formula Ii

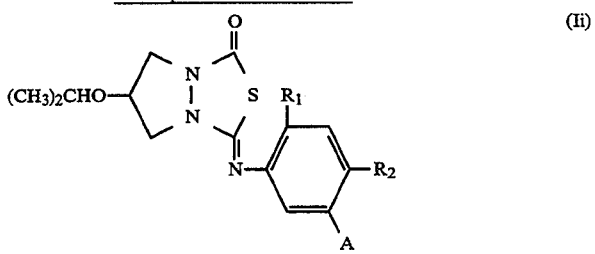

(Ii)

| Comp. No. | R₁ | R₂ | A | phys. data |
|---|---|---|---|---|
| 7.140 | F | Cl | —S—◁—COOC₂H₅ with CH₃ | |
| 7.141 | F | Cl | —S—◁—COOC₂H₅ with C₂H₅ | |
| 7.142 | F | Cl | —S—◁—COOCH₃ with F | |
| 7.143 | F | Cl | —S—◁—COOC₂H₅ with F | |
| 7.144 | F | Cl | —S—◁—COO—CH(CH₃)₂ | |
| 7.145 | F | Cl | —S—◁—COO—cyclopentyl | |
| 7.146 | F | Cl | —NH—SO₂—CH₃ | |
| 7.147 | F | Cl | —NH—SO₂—C₂H₅ | |
| 7.148 | F | Cl | —NH—SO₂—Cl | |
| 7.149 | F | Cl | —NH—SO₂—cyclopropyl | |
| 7.150 | F | Cl | —O—P(=O)(OC₂H₅)(OC₂H₅) | |
| 7.151 | H | Cl | —COOH | |
| 7.152 | H | Cl | —COOCH₃ | |
| 7.153 | H | Cl | —COO—CH(CH₃)₂ | |
| 7.154 | H | Cl | —COO—C₅H₁₁ | |
| 7.155 | H | Cl | —COO—CH₂—CH₂—O—CH₃ | |
| 7.156 | H | Cl | —COOCH₂—S—CH₃ | |
| 7.157 | H | Cl | —COOH(CH₃)—CH₂—S—CH₃ | |

TABLE 7-continued

Compounds of formula Ii (Ii)

| Comp. No. | R₁ | R₂ | A | phys. data |
|---|---|---|---|---|
| 7.158 | H | Cl | —COO—CH(CH₃)—CH₂—N(CH₃)₂ | |
| 7.159 | H | Cl | —CO—N(CH₃)₂ | |
| 7.160 | H | Cl | —CO—N(morpholino) | |
| 7.161 | H | Cl | —COON=C(CH₃)₂ | |
| 7.162 | H | Cl | —COOCH₂—CH₂—O—N=C(CH₃)₂ | |
| 7.163 | H | Cl | —COO—cyclohexyl | |
| 7.164 | H | Cl | —CH(CH₃)—cyclopropyl | |
| 7.165 | H | Cl | —S—C₃H₇ | |
| 7.166 | H | Cl | —COOCH₂—COOCH₃ | |
| 7.167 | H | Cl | —COOCH(CH₃)—COOCH₃ | |
| 7.168 | H | Cl | —COS—CH₂—COOCH₃ | |
| 7.169 | H | Cl | —COS—CH(CH₃)—COOCH₃ | |
| 7.170 | H | Cl | —OH | |
| 7.171 | H | Cl | —OCH₃ | |
| 7.172 | H | Cl | —O—C₂H₅ | |
| 7.173 | H | Cl | —O—CH(CH₃)₂ | |
| 7.174 | H | Cl | —O—CH₂—C≡CH | |
| 7.175 | H | Cl | —O—CH₂—CH=CHCl | |
| 7.176 | H | Cl | —O—CH₂—C(Cl)=CH₂ | |
| 7.177 | H | Cl | —O—CH(CH₃)—C≡CH | |

TABLE 7-continued

Compounds of formula Ii

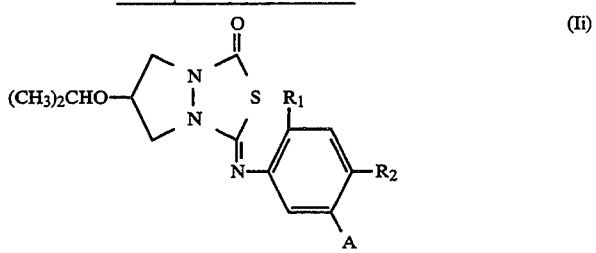
(Ii)

| Comp. No. | R₁ | R₂ | A | phys. data |
|---|---|---|---|---|
| 7.178 | H | Cl | —O—CH₂—COOCH₃ | |
| 7.179 | H | Cl | —O—CH₂—COOC₂H₅ | |
| 7.180 | H | Cl | —O—CH(CH₃)—COOCH₃ | |
| 7.181 | H | Cl | —SH | |
| 7.182 | H | Cl | —SCH₃ | |
| 7.183 | H | Cl | —SC₂H₅ | |
| 7.184 | H | Cl | —S—CH(CH₃)₂ | |
| 7.185 | H | Cl | —S—CH₂—COOCH₃ | |
| 7.186 | H | Cl | —S—CH(CH₃)—COOCH₃ | |
| 7.187 | H | Cl | —S—CH₂—COOC₂H₅ | |
| 7.188 | H | Cl | —C(=N—OCH₃)—CN | |
| 7.189 | H | Cl | —C(CH₃)(O—CH(CH₃)—CH(CH₃)—O) (cyclic acetal) | |
| 7.190 | H | Cl | —S—(cyclopropyl)—COOC₂H₅ | |
| 7.191 | H | Cl | —S—(cyclopropyl)—COOH | |
| 7.192 | H | Cl | —S—(cyclopropyl)—COO—CH(CH₃)₂ | |
| 7.193 | H | Cl | —S—(cyclopropyl, CH₃)—COOC₂H₅ | |
| 7.194 | H | Cl | —S—(cyclopropyl, F)—COOC₂H₅ | |
| 7.195 | H | Cl | —S—(cyclopropyl, CF₃)—COOC₂H₅ | |

TABLE 7-continued

Compounds of formula Ii

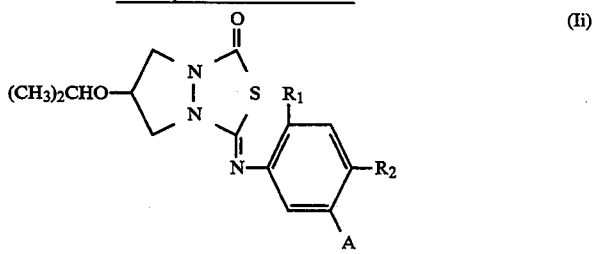

(Ii)

| Comp. No. | R₁ | R₂ | A | phys. data |
|---|---|---|---|---|
| 7.196 | H | Cl | —S—△—COO—CH(CH₃)₂ with CF₃ on ring | |
| 7.197 | H | Cl | —S—△—COOH | |
| 7.198 | H | Cl | —S—△—COOH with CF₃ | |
| 7.199 | H | Cl | —S—△—COOC₅H₁₁ with CF₃ | |
| 7.200 | H | Cl | —S—△—COOC₂H₅ with C₂H₅ | |
| 7.201 | H | Cl | —S—△—COOC₂H₅ with CH(CH₃)₂ | |
| 7.202 | H | Cl | —NH—SO₂—C₂H₅ | |
| 7.203 | H | Cl | —NH—SO₂—CH₂—Cl | |
| 7.204 | F | CN | —COOH | |
| 7.205 | F | CN | —COO—CH(CH₃)₂ | |
| 7.206 | F | CN | —O—CH(CH₃)₂ | |
| 7.207 | F | CN | —O—CH₂—C≡CH | |
| 7.208 | F | CN | —O—CH(CH₃)—C≡CH | |
| 7.209 | F | CN | —S—CH₂—COOCH₃ | |
| 7.210 | F | CN | —S—CH(CH₃)—COOCH₃ | |
| 7.211 | F | CN | —O—CH₂—COOCH₃ | |
| 7.212 | F | CN | —O—CH₂—COOC₅H₁₁ | |
| 7.213 | F | CN | —O—CH(CH₃)—COOC₂H₅ | |
| 7.214 | F | CN | —S—△—COOCH₃ | |
| 7.215 | F | CN | —S—△—COOC₂H₅ | |

TABLE 7-continued

Compounds of formula Ii

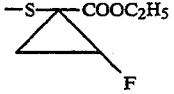

(Ii)

| Comp. No. | R₁ | R₂ | A | phys. data |
|---|---|---|---|---|
| 7.216 | F | CN | 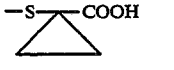 -S-⟨cyclopropyl with COOC₂H₅ and F⟩ | |
| 7.217 | F | CN | -S-⟨cyclopropyl with COOH⟩ | |
| 7.218 | F | CN | -S-⟨cyclopropyl with COOH and F⟩ | |
| 7.219 | F | CN | -S-⟨cyclopropyl with COOH and CF₃⟩ | |
| 7.220 | F | CN | -S-⟨cyclopropyl with COOC₂H₅⟩ | |
| 7.221 | F | Br | —COOH | |
| 7.222 | F | Br | —COO—CH(CH₃)₂ | |
| 7.223 | F | Br | —OH | |
| 7.224 | F | Br | —O—CH(CH₃)₂ | |
| 7.225 | F | Br | —O—CH₂—C≡CH | |
| 7.226 | F | Br | —O—CH(CH₃)—C≡CH | |
| 7.227 | F | Br | —O—CH₂COOCH₃ | |
| 7.228 | F | Br | —O—CH₂—COOC₅H₁₁ | |
| 7.229 | F | Br | —S—CH₂—COOCH₃ | |
| 7.230 | F | Br | -S-⟨cyclopropyl with COOC₂H₅⟩ | |
| 7.231 | F | Br | -S-⟨cyclopropyl with COOH and F⟩ | |
| 7.232 | F | Br | -S-⟨cyclopropyl with COOC₂H₅ and F⟩ | |
| 7.233 | F | Cl | —S—CH₂COOH | |

TABLE 8

Compounds of formula Ij

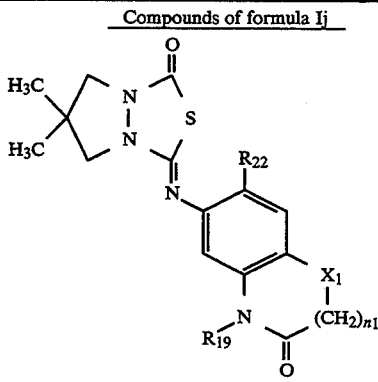

(Ij)

| Comp. No. | $R_{22}$ | $X_1$ | $R_{19}$ | $n_1$ | phys. data |
|---|---|---|---|---|---|
| 8.001 | F | S | —$C_3H_7$(i) | 0 | m.p. 136–137° C. |
| 8.002 | H | S | —$C_3H_7$(i) | 0 | |
| 8.003 | H | S | —$CH_2C\equiv CH$ | 0 | |
| 8.004 | F | S | —$CH_2C\equiv CH$ | 0 | |
| 8.005 | F | S | —$CH(CH_3)C\equiv CH$ | 0 | |
| 8.006 | H | S | —$CH(CH_3)C\equiv CH$ | 0 | |
| 8.007 | H | S | —$CH(CH_3)COOCH_3$ | 0 | |
| 8.008 | F | S | —$CH(CH_3)COOCH_3$ | 0 | |
| 8.009 | H | S | —$CH_2$—$COOCH_3$ | 0 | |
| 8.010 | H | S | —$CH_2$—$COOC_3H_7$(i) | 0 | |
| 8.011 | F | O | —$C_3H_7$(i) | 1 | |
| 8.012 | H | O | —$C_3H_7$(i) | 1 | |
| 8.013 | F | O | —$CH_2$—$C\equiv CH$ | 1 | |
| 8.014 | H | O | —$CH_2$—$C\equiv CH$ | 1 | |
| 8.015 | F | O | —$CH(CH_3)C\equiv CH$ | 1 | |
| 8.016 | H | O | —$CH(CH_3)C\equiv CH$ | 1 | |
| 8.017 | H | O | —$CH_2COOCH_3$ | 1 | |
| 8.018 | F | O | —$CH_2$—$COOC_3H_7$(i) | 1 | |
| 8.019 | H | O | —$CH(CH_3)COOC_3H_7$(i) | 1 | |

TABLE 9

Compounds of formula Ik

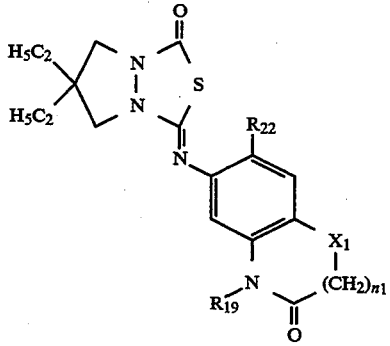

(Ik)

| Comp. No. | $R_{22}$ | $X_1$ | $R_{19}$ | $n_1$ | phys. data |
|---|---|---|---|---|---|
| 9.001 | F | S | —$C_3H_7$(i) | 0 | |
| 9.002 | H | S | —$C_3H_7$(i) | 0 | |
| 9.003 | H | S | —$CH_2$—$C\equiv CH$ | 0 | |
| 9.004 | F | S | —$CH_2$—$C\equiv CH$ | 0 | |
| 9.005 | F | S | —$CH(CH_3)C\equiv CH$ | 0 | |
| 9.006 | H | S | —$CH(CH_3)C\equiv CH$ | 0 | |
| 9.007 | H | S | —$CH(CH_3)COOCH_3$ | 0 | |
| 9.008 | F | S | —$CH(CH_3)COOCH_3$ | 0 | |
| 9.009 | H | S | —$CH_2$—$COOCH_3$ | 0 | |
| 9.010 | H | S | —$CH_2$—$COOC_3H_7$(i) | 0 | |
| 9.011 | F | O | —$C_3H_7$(i) | 1 | |
| 9.012 | H | O | —$C_3H_7$(i) | 1 | |
| 9.013 | F | O | —$CH_2$—$C\equiv CH$ | 1 | |
| 9.014 | H | O | —$CH_2$—$C\equiv CH$ | 1 | |
| 9.015 | F | O | —$CH(CH_3)C\equiv CH$ | 1 | |
| 9.016 | H | O | —$CH(CH_3)C\equiv CH$ | 1 | |

TABLE 9-continued

Compounds of formula Ik

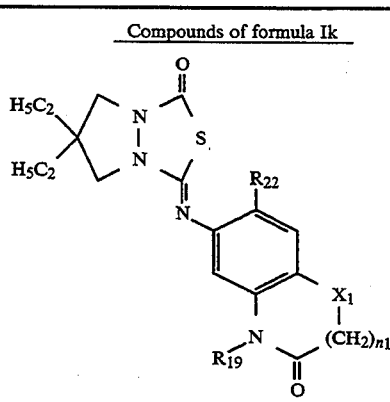

(Ik)

| Comp. No. | $R_{22}$ | $X_1$ | $R_{19}$ | $n_1$ | phys. data |
|---|---|---|---|---|---|
| 9.017 | H | O | —$CH_2COOCH_3$ | 1 | |
| 9.018 | F | O | —$CH_2$—$COOC_3H_7$(i) | 1 | |
| 9.019 | H | O | —$CH(CH_3)COOC_3H_7$(i) | 1 | |

TABLE 10

Compounds of formula Il

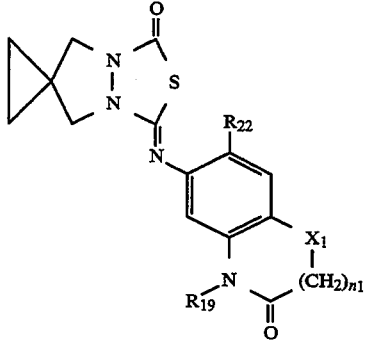

(Il)

| Comp. No. | $R_{22}$ | $X_1$ | $R_{19}$ | $n_1$ | phys. data |
|---|---|---|---|---|---|
| 10.001 | F | S | —$C_3H_7$(i) | 0 | |
| 10.002 | H | S | —$C_3H_7$(i) | 0 | m.p. > 73° C. (decomp.) |
| 10.003 | H | S | —$CH_2$—$C\equiv CH$ | 0 | |
| 10.004 | F | S | —$CH_2$—$C\equiv CH$ | 0 | |
| 10.005 | F | S | —$CH(CH_3)C\equiv CH$ | 0 | |
| 10.006 | H | S | —$CH(CH_3)C\equiv CH$ | 0 | |
| 10.007 | H | S | —$CH(CH_3)COOCH_3$ | 0 | |
| 10.008 | F | S | —$CH(CH_3)COOC_2H_5$ | 0 | amorphous |
| 10.009 | H | S | —$CH_2$—$COOCH_3$ | 0 | |
| 10.010 | H | S | —$CH_2$—$COOC_3H_7$(i) | 0 | |
| 10.011 | F | O | —$C_3H_7$(i) | 1 | |
| 10.012 | H | O | —$C_3H_7$(i) | 1 | |
| 10.013 | F | O | —$CH_2$—$C\equiv CH$ | 1 | |
| 10.014 | H | O | —$CH_2$—$C\equiv CH$ | 1 | |
| 10.015 | F | O | —$CH(CH_3)C\equiv CH$ | 1 | |
| 10.016 | H | O | —$CH(CH_3)C\equiv CH$ | 1 | |
| 10.017 | H | O | —$CH_2COOCH_3$ | 1 | |
| 10.018 | F | O | —$CH_2$—$COOC_3H_7$(i) | 1 | |
| 10.019 | H | O | —$CH(CH_3)COOC_3H_7$(i) | 1 | |

TABLE 11

Compounds of formula Im

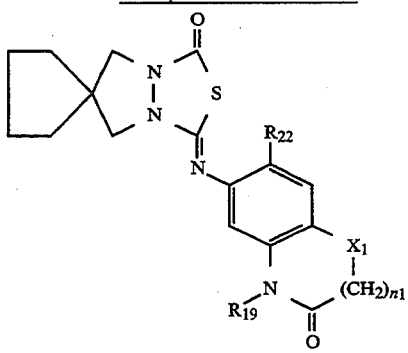

(Im)

| Comp. No. | R22 | X1 | R19 | n1 | phys. data |
|---|---|---|---|---|---|
| 11.001 | F | S | —C3H7(i) | 0 | |
| 11.002 | H | S | —C3H7(i) | 0 | |
| 11.003 | H | S | —CH2—C≡CH | 0 | |
| 11.004 | F | S | —CH2—C≡CH | 0 | |
| 11.005 | F | S | —CH(CH3)C≡CH | 0 | |
| 11.006 | H | S | —CH(CH3)C≡CH | 0 | |
| 11.007 | H | S | —CH(CH3)COOCH3 | 0 | |
| 11.008 | F | S | —CH(CH3)COOCH3 | 0 | |
| 11.009 | H | S | —CH2—COOCH3 | 0 | |
| 11.010 | H | S | —CH2—COOC3H7(i) | 0 | |
| 11.011 | F | O | —C3H7(i) | 1 | |
| 11.012 | H | O | —C3H7(i) | 1 | |
| 11.013 | F | O | —CH2—C≡CH | 1 | |
| 11.014 | H | O | —CH2—C≡CH | 1 | |
| 11.015 | F | O | —CH(CH3)C≡CH | 1 | |
| 11.016 | H | O | —CH(CH3)C≡CH | 1 | |
| 11.017 | H | O | —CH2COOCH3 | 1 | |
| 11.018 | F | O | —CH2—COOC3H7(i) | 1 | |
| 11.019 | H | O | —CH(CH3)COOC3H7(i) | 1 | |

TABLE 12

Compounds of formula In

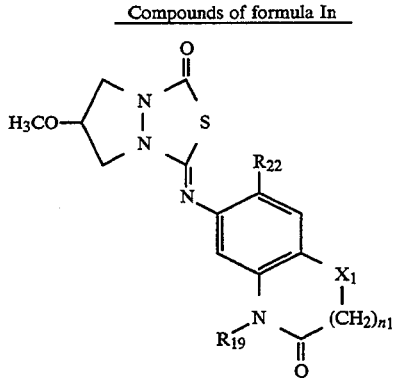

(In)

| Comp. No. | R22 | X1 | R19 | n1 | phys. data |
|---|---|---|---|---|---|
| 12.001 | F | S | —C3H7(i) | 0 | |
| 12.002 | H | S | —C3H7(i) | 0 | |
| 12.003 | H | S | —CH2—C≡CH | 0 | |
| 12.004 | F | S | —CH2—C≡CH | 0 | |
| 12.005 | F | S | —CH(CH3)C≡CH | 0 | |
| 12.006 | H | S | —CH(CH3)C≡CH | 0 | |
| 12.007 | H | S | —CH(CH3)COOCH3 | 0 | |
| 12.008 | F | S | —CH(CH3)COOCH3 | 0 | |
| 12.009 | H | S | —CH2—COOCH3 | 0 | |
| 12.010 | H | S | —CH2—COOC3H7(i) | 0 | |
| 12.011 | F | O | —C3H7(i) | 1 | |
| 12.012 | H | O | —C3H7(i) | 1 | |
| 12.013 | F | O | —CH2—C≡CH | 1 | |
| 12.014 | H | O | —CH2—C≡CH | 1 | |
| 12.015 | F | O | —CH(CH3)C≡CH | 1 | |
| 12.016 | H | O | —CH(CH3)C≡CH | 1 | |
| 12.017 | H | O | —CH2COOCH3 | 1 | |
| 12.018 | F | O | —CH2—COOC3H7(i) | 1 | |
| 12.019 | H | O | —CH(CH3)COOC3H7(i) | 1 | |

TABLE 13

Compounds of formula Io

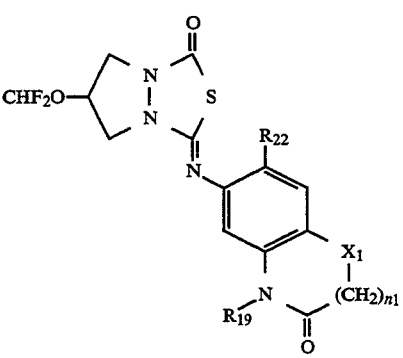

(Io)

| Comp. No. | R22 | X1 | R19 | n1 | phys. data |
|---|---|---|---|---|---|
| 13.001 | F | S | —C3H7(i) | 0 | |
| 13.002 | H | S | —C3H7(i) | 0 | |
| 13.003 | H | S | —CH2—C≡CH | 0 | |
| 13.004 | F | S | —CH2—C≡CH | 0 | |
| 13.005 | F | S | —CH(CH3)C≡CH | 0 | |
| 13.006 | H | S | —CH(CH3)C≡CH | 0 | |
| 13.007 | H | S | —CH(CH3)COOCH3 | 0 | |
| 13.008 | F | S | —CH(CH3)COOCH3 | 0 | |
| 13.009 | H | S | —CH2—COOCH3 | 0 | |
| 13.010 | H | S | —CH2—COOC3H7(i) | 0 | |
| 13.011 | F | O | —C3H7(i) | 1 | |
| 13.012 | H | O | —C3H7(i) | 1 | |
| 13.013 | F | O | —CH2—C≡CH | 1 | |
| 13.014 | H | O | —CH2—C≡CH | 1 | |
| 13.015 | F | O | —CH(CH3)C≡CH | 1 | |
| 13.016 | H | O | —CH(CH3)C≡CH | 1 | |
| 13.017 | H | O | —CH2COOCH3 | 1 | |
| 13.018 | F | O | —CH2—COOC3H7(i) | 1 | |
| 13.019 | H | O | —CH(CH3)COOC3H7(i) | 1 | |

TABLE 14

Compounds of formula Ip

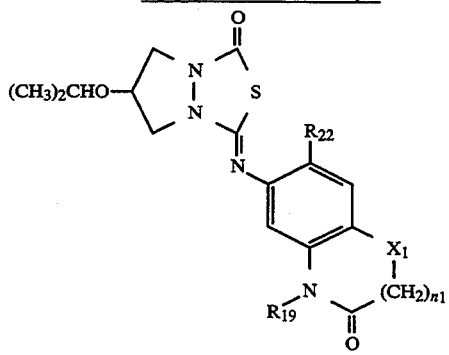

(Ip)

| Comp. No. | $R_{22}$ | $X_1$ | $R_{19}$ | $n_1$ | phys. data |
|---|---|---|---|---|---|
| 14.001 | F | S | —$C_3H_7$(i) | 0 | |
| 14.002 | H | S | —$C_3H_7$(i) | 0 | |
| 14.003 | H | S | —$CH_2C\equiv CH$ | 0 | |
| 14.004 | F | S | —$CH_2C\equiv CH$ | 0 | |
| 14.005 | F | S | —$CH(CH_3)C\equiv CH$ | 0 | |
| 14.006 | H | S | —$CH(CH_3)C\equiv CH$ | 0 | |
| 14.007 | H | S | —$CH(CH_3)COOCH_3$ | 0 | |
| 14.008 | F | S | —$CH(CH_3)COOCH_3$ | 0 | |
| 14.009 | H | S | —$CH_2$—$COOCH_3$ | 0 | |
| 14.010 | H | S | —$CH_2$—$COOC_3H_7$(i) | 0 | |
| 14.011 | F | O | —$C_3H_7$(i) | 1 | |
| 14.012 | H | O | —$C_3H_7$(i) | 1 | |
| 14.013 | F | O | —$CH_2$—$C\equiv CH$ | 1 | |
| 14.014 | H | O | —$CH_2$—$C\equiv CH$ | 1 | |
| 14.015 | F | O | —$CH(CH_3)C\equiv CH$ | 1 | |
| 14.016 | H | O | —$CH(CH_3)C\equiv CH$ | 1 | |
| 14.017 | H | O | —$CH_2COOCH_3$ | 1 | |
| 14.018 | F | O | —$CH_2$—$COOC_3H_7$(i) | 1 | |
| 14.019 | H | O | —$CH(CH_3)COOC_3H_7$(i) | 1 | |

TABLE 15

Compounds of formula Iq

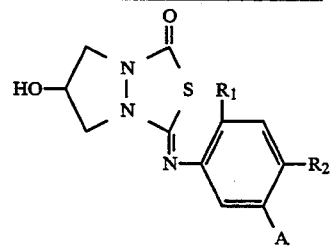

(Iq)

| Comp. No. | $R_1$ | $R_2$ | A | phys. data |
|---|---|---|---|---|
| 15.001 | F | Cl | —H | |
| 15.002 | F | Cl | —CN | |
| 15.003 | F | Cl | —$NO_2$ | |
| 15.004 | F | Cl | —COOH | |
| 15.005 | F | Cl | —$COOCH_3$ | resin |
| 15.006 | F | Cl | —$COOC_2H_5$ | |
| 15.007 | F | Cl | —$COOC_3H_7$ | |
| 15.008 | F | Cl | —$COOCH(CH_3)_2$ | |
| 15.009 | F | Cl | —$COOC_4H_9$ | |
| 15.010 | F | Cl | —COOCH(CH$_3$)—$CH_2$—$CH_3$ | |
| 15.011 | F | Cl | —$COOCH_2$—$CH_2$—CH(CH$_3$)$_2$ | |
| 15.012 | F | Cl | —$COOC_5H_{11}$ | |
| 15.013 | F | Cl | —$COOCH_2$—$CH_2$—O—$CH_3$ | |
| 15.014 | F | Cl | —$COOCH_2$—$CH_2$—O—$C_2H_5$ | |
| 15.015 | F | Cl | —$COOCH(CH_3)$—$CH_2$—$OCH_3$ | |
| 15.016 | F | Cl | —$COOCH_2$—$CH_2$—S—$CH_3$ | |
| 15.017 | F | Cl | —$COOCH(CH_3)$—$CH_2$—S—$CH_3$ | |
| 15.018 | F | Cl | —$COOCH(CH_3)$—$CH_2$—S—$C_2H_5$ | |
| 15.019 | F | Cl | —$COOCH(CH_3)$—$CH_2$—S—$C_3H_7$ | |
| 15.020 | F | Cl | —$COOCH(CH_3)$—$CH_2$—S—CH(CH$_3$)$_2$ | |
| 15.021 | F | Cl | —$COOCH(CH_3)$—$CH_2$—S—$C_4H_9$ | |
| 15.022 | F | Cl | —$COOCH(CH_3)$—$CH_2$—S—$C_5H_{11}$ | |
| 15.023 | F | Cl | —$COOCH(CH_3)$—$CH_2$—N(CH$_3$)$_2$ | |

TABLE 15-continued

Compounds of formula Iq

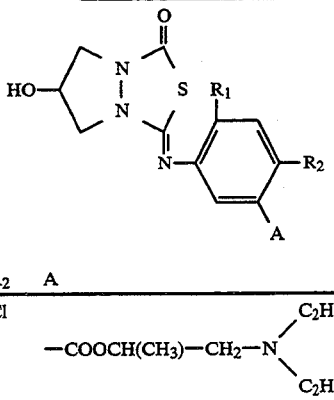

(Iq)

| Comp. No. | R$_1$ | R$_2$ | A | phys. data |
|---|---|---|---|---|
| 15.024 | F | Cl | —COOCH(CH$_3$)—CH$_2$—N(C$_2$H$_5$)$_2$ | |
| 15.025 | F | Cl | —CONH$_2$ | |
| 15.026 | F | Cl | —CONH—CH$_3$ | |
| 15.027 | F | Cl | —CON(CH$_3$)$_2$ | |
| 15.028 | F | Cl | —CON(CH$_3$)(C$_4$H$_9$) | |
| 15.029 | F | Cl | —CON(CH$_2$—CH$_2$—OH)$_2$ | |
| 15.030 | F | Cl | —CONH—CH$_2$—CH=CH$_2$ | |
| 15.031 | F | Cl | —CON(CH$_2$—CH=CH$_2$)$_2$ | |
| 15.032 | F | Cl | —CON⟨pyrrolidine⟩ | |
| 15.033 | F | Cl | —CON⟨piperidine⟩ | |
| 15.034 | F | Cl | —CON⟨morpholine⟩ | |
| 15.035 | F | Cl | —CON⟨thiomorpholine⟩ | |
| 15.036 | F | Cl | —CON⟨N-methylpiperazine⟩ | |
| 15.037 | F | Cl | —COON=C(CH$_3$)$_2$ | |
| 15.038 | F | Cl | —COOCH$_2$—CH$_2$—Cl | |
| 15.039 | F | Cl | —COOCH$_2$—CN | |

TABLE 15-continued
Compounds of formula Iq
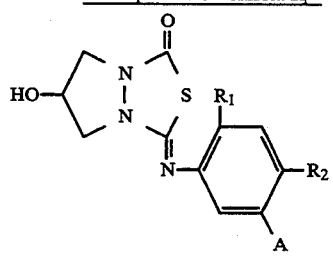
(Iq)
| Comp. No. | R₁ | R₂ | A | phys. data |
|---|---|---|---|---|
| 15.040 | F | Cl | —COOCH(CN)CH₃ | |
| 15.041 | F | Cl | —COOCH₂—CH=CH₂ | |
| 15.042 | F | Cl | —COOCH₂—CH=CHCl | |
| 15.043 | F | Cl | —COOCH₂—C(Cl)=CH₂ | |
| 15.044 | F | Cl | —COOCH₂—C≡CH | |
| 15.045 | F | Cl | —COO—CH(CH₃)—C≡CH | |
| 15.046 | F | Cl | —COO-cyclopentyl | |
| 15.047 | F | Cl | —COO-cyclohexyl | |
| 15.048 | F | Cl | —COOCH₂-cyclopentyl | |
| 15.049 | F | Cl | —COOCH(CH₃)-cyclopropyl | |
| 15.050 | F | Cl | —COOCH₂-phenyl | |
| 15.051 | F | Cl | —COOCH₂-(2-chlorophenyl) | |
| 15.052 | F | Cl | COOCH₂-(4-methylphenyl) | |
| 15.053 | F | Cl | —COSCH₃ | |

TABLE 15-continued

Compounds of formula Iq

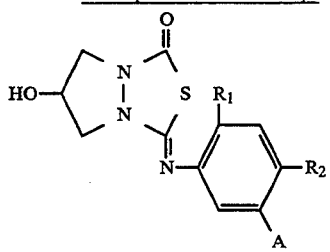

(Iq)

| Comp. No. | R₁ | R₂ | A | phys. data |
|---|---|---|---|---|
| 15.054 | F | Cl | —COSC₂H₅ | |
| 15.055 | F | Cl | —COSC₃H₇ | |
| 15.056 | F | Cl | —COS—CH₂—CH=CH₂ | |
| 15.057 | F | Cl | —COS—CH₂—COOCH₃ | |
| 15.058 | F | Cl | —COS—CH₂—COOC₂H₅ | |
| 15.059 | F | Cl | —COS—CH₂—COOC₅H₁₁ | |
| 15.060 | F | Cl | —COS—CH(CH₃)—COOCH₃ | |
| 15.061 | F | Cl | —COS—CH(CH₃)—COOC₂H₅ | |
| 15.062 | F | Cl | —COS—CH(CH₃)—COOC₃H₇ | |
| 15.063 | F | Cl | —COS—CH₂—CH₂—COOCH₃ | |
| 15.064 | F | Cl | —COS—CH₂—COOCH₂—CH₂—O—CH₃ | |
| 15.065 | F | Cl | —COOCH₂—COOCH₃ | |
| 15.066 | F | Cl | —COOCH(CH₃)—COOCH₃ | |
| 15.067 | F | Cl | —COOCH₂—COOC₅H₁₁ | |
| 15.068 | F | Cl | —COOCH₂—CH₂—Si(CH₃)₃ | |
| 15.069 | F | Cl | —COONa | |
| 15.070 | F | Cl | —COOCH₂—CH₂—O—N=C(CH₃)₂ | |
| 15.071 | F | Cl | —OH | |
| 15.072 | F | Cl | —OCH₃ | |
| 15.073 | F | Cl | —OC₂H₅ | |
| 15.074 | F | Cl | —OC₃H₇ | |
| 15.075 | F | Cl | —OCH(CH₃)₂ | resin |
| 15.076 | F | Cl | —OC₄H₉ | |
| 15.077 | F | Cl | —OCH(CH₃)—C₂H₅ | |
| 15.078 | F | Cl | —O—CH₂—CH(CH₃)₂ | |
| 15.079 | F | Cl | —OCH₂CH=CH₂ | |
| 15.080 | F | Cl | —OCH₂—C(Cl)=CH₂ | |
| 15.081 | F | Cl | —OCH₂CH=CHCl | |

TABLE 15-continued

Compounds of formula Iq

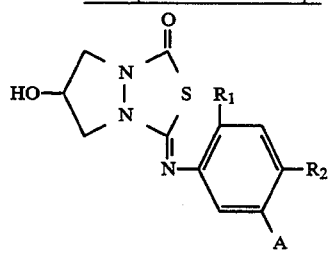

(Iq)

| Comp. No. | R$_1$ | R$_2$ | A | phys. data |
|---|---|---|---|---|
| 15.082 | F | Cl | —OCH$_2$C≡CH | |
| 15.083 | F | Cl | —OCH(CH$_3$)—C≡CH | |
| 15.084 | F | Cl | —OCH$_2$—COOCH$_3$ | |
| 15.085 | F | Cl | —O—CH$_2$—COOC$_5$H$_{11}$ | |
| 15.086 | F | Cl | —O—CH(CH$_3$)—COOCH$_3$ | |
| 15.087 | F | Cl | —O—CH$_2$—COOC$_2$H$_5$ | |
| 15.088 | F | Cl | —O—CH(CH$_3$)—COOC$_2$H$_5$ | |
| 15.089 | F | Cl | —O—CH$_2$—CH$_2$—O—CH$_3$ | |
| 15.090 | F | Cl | —O—CH(CH$_3$)—CH$_2$—S—CH$_3$ | |
| 15.091 | F | Cl | —O—CH(CH$_3$)—CH$_2$—S—C$_2$H$_5$ | |
| 15.092 | F | Cl | —O—CH(CH$_3$)—CH$_2$—S—C$_3$H$_7$ | |
| 15.093 | F | Cl | —O—CH$_2$—CH$_2$—Cl | |
| 15.094 | F | Cl | —O—CH$_2$—CN | |
| 15.095 | F | Cl | —O—CH(CH$_3$)—CN | |
| 15.096 | F | Cl | —S—CH$_3$ | |
| 15.097 | F | Cl | —S—C$_2$H$_5$ | |
| 15.098 | F | Cl | —S—C$_3$H$_7$ | |
| 15.099 | F | Cl | —S—CH(CH$_3$)$_2$ | |
| 15.100 | F | Cl | —S—CH$_2$—CH=CH$_2$ | |
| 15.101 | F | Cl | —S—CH$_2$—C(Cl)=CH$_2$ | |
| 15.102 | F | Cl | —S—CH$_2$—CH=CHCl | |
| 15.103 | F | Cl | —S—CH$_2$—C≡CH | |
| 15.104 | F | Cl | —S—CH(CH$_3$)—C≡CH | |
| 15.105 | F | Cl | —S—CH$_2$—COOCH$_3$ | resin |
| 15.106 | F | Cl | —S—CH$_2$—COOC$_2$H$_5$ | |

TABLE 15-continued

Compounds of formula Iq (Iq)

[Structure: pyrazolidine ring with HO- substituent, N-N, C=O, S, connected via C=N to phenyl ring with R₁, R₂, and A substituents]

| Comp. No. | R₁ | R₂ | A | phys. data |
|---|---|---|---|---|
| 15.107 | F | Cl | —S—CH₂—COOC₅H₁₁ | |
| 15.108 | F | Cl | —S—CH(CH₃)—COOCH₃ | |
| 15.109 | F | Cl | —S—CH(CH₃)—COOC₂H₅ | |
| 15.110 | F | Cl | —S—CH₂—COOCH₂—CH₂—O—CH₃ | |
| 15.111 | F | Cl | —O—CH₂—C₆H₅ | |
| 15.112 | F | Cl | —S—CH₂—C₆H₅ | |
| 15.113 | F | Cl | —C(=N—O—CH₃)—CN | |
| 15.114 | F | Cl | —C(=N—O—CH₂—COOCH₃)—CN | |
| 15.115 | F | Cl | —C(=N—O—CH₂—C≡CH)—CN | |
| 15.116 | F | Cl | —C(=N—O—CH₃)—CH₃ | |
| 15.117 | F | Cl | —C(=N—O—CH₂—C≡CH)—CH₃ | |
| 15.118 | F | Cl | —C(=N—O—CH₃)—CH₂—O—CH₃ | |
| 15.119 | F | Cl | —C(CH₃)(O—CH₃)(O—CH₃) | |
| 15.120 | F | Cl | —C(CH₃)(O—C₂H₅)(O—C₂H₅) | |

TABLE 15-continued
Compounds of formula Iq
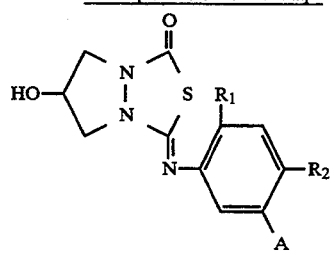
(Iq)
| Comp. No. | R₁ | R₂ | A | phys. data |
|---|---|---|---|---|
| 15.121 | F | Cl | 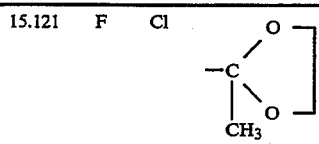 | |
| 15.122 | F | Cl | 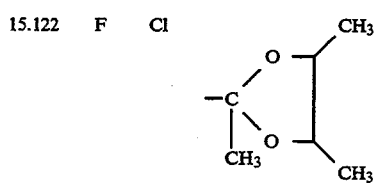 | |
| 15.123 | F | Cl | 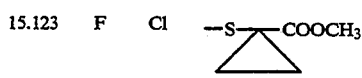 | |
| 15.124 | F | Cl | 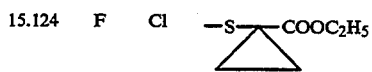 | |
| 15.125 | F | Cl | 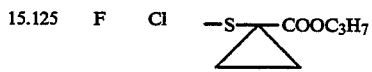 | |
| 15.126 | F | Cl | 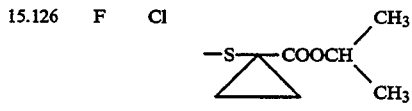 | |
| 15.127 | F | Cl | 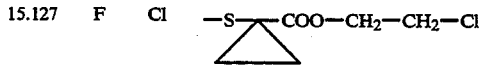 | |
| 15.128 | F | Cl | 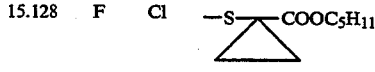 | |
| 15.129 | F | Cl | 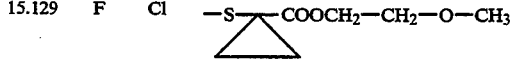 | |
| 15.130 | F | Cl | 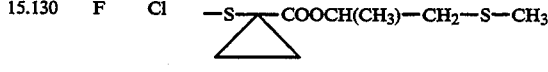 | |
| 15.131 | F | Cl | 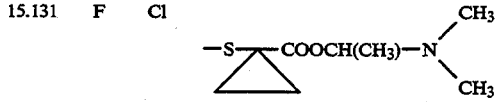 | |
| 15.132 | F | Cl | 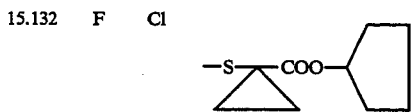 | |
| 15.133 | F | Cl | 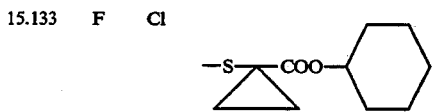 | |

TABLE 15-continued

Compounds of formula Iq

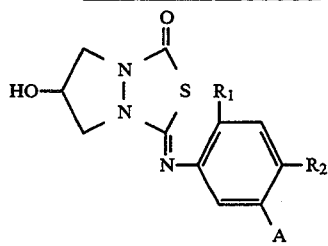

(Iq)

| Comp. No. | R₁ | R₂ | A | phys. data |
|---|---|---|---|---|
| 15.134 | F | Cl | —S—[cyclopropyl]—COO—CH₂—CH₂—CH=CH₂ | |
| 15.135 | F | Cl | —S—[cyclopropyl]—COO—CH₂—C(Cl)=CH₂ | |
| 15.136 | F | Cl | —S—[cyclopropyl]—COO—CH₂—C≡CH | |
| 15.137 | F | Cl | —S—[cyclopropyl]—COOH | |
| 15.138 | F | Cl | —S—[cyclopropyl]—CONH₂ | |
| 15.139 | F | Cl | —S—[cyclopropyl]—CONH—CH₃ | |
| 15.140 | F | Cl | —S—[cyclopropyl(CH₃)]—COOC₂H₅ | |
| 15.141 | F | Cl | —S—[cyclopropyl(C₂H₅)]—COOC₂H₅ | |
| 15.142 | F | Cl | —S—[cyclopropyl(F)]—COOCH₃ | |
| 15.143 | F | Cl | —S—[cyclopropyl(F)]—COOC₂H₅ | |
| 15.144 | F | Cl | —S—[cyclopropyl]—COO—CH(CH₃)₂ | |
| 15.145 | F | Cl | —S—[cyclopropyl]—COO—cyclopentyl | |
| 15.146 | F | Cl | —NH—SO₂—CH₃ | |
| 15.147 | F | Cl | —NH—SO₂—C₂H₅ | |
| 15.148 | F | Cl | —NH—SO₂—Cl | |

TABLE 15-continued
Compounds of formula Iq
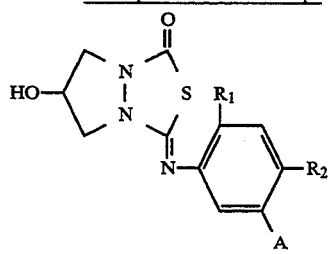
(Iq)
| Comp. No. | R₁ | R₂ | A | phys. data |
|---|---|---|---|---|
| 15.149 | F | Cl | 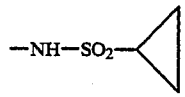 | |
| 15.150 | F | Cl | 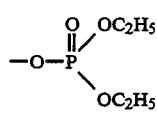 | |
| 15.151 | H | Cl | —COOH | |
| 15.152 | H | Cl | —COOCH₃ | m.p. 138–141° C. |
| 15.153 | H | Cl | 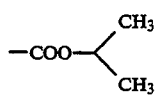 | |
| 15.154 | H | Cl | —COO—C₅H₁₁ | |
| 15.155 | H | Cl | —COO—CH₂—CH₂—O—CH₃ | |
| 15.156 | H | Cl | —COOCH₂—S—CH₃ | |
| 15.157 | H | Cl | —COOCH(CH₃)—CH₂—S—CH₃ | |
| 15.158 | H | Cl | 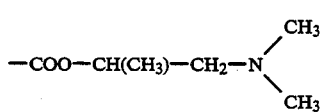 | |
| 15.159 | H | Cl | 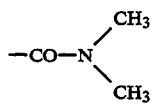 | |
| 15.160 | H | Cl | 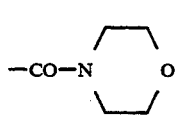 | |
| 15.161 | H | Cl | 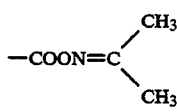 | |
| 15.162 | H | Cl | 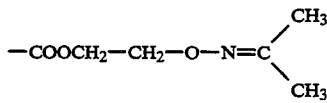 | |
| 15.163 | H | Cl | 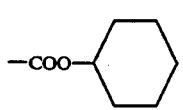 | |
| 15.164 | H | Cl | 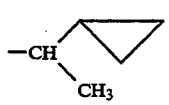 | |
| 15.165 | H | Cl | —S—C₃H₇ | |

TABLE 15-continued

Compounds of formula Iq

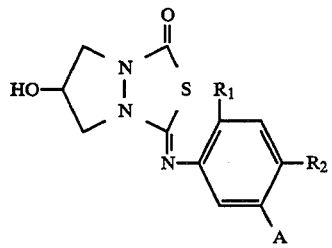

(Iq)

| Comp. No. | R₁ | R₂ | A | phys. data |
|---|---|---|---|---|
| 15.166 | H | Cl | —COOCH₂—COOCH₃ | |
| 15.167 | H | Cl | —COOCH(CH₃)—COOCH₃ | |
| 15.168 | H | Cl | —COS—CH₂—COOCH₃ | |
| 15.169 | H | Cl | —COS—CH(CH₃)—COOCH₃ | |
| 15.170 | H | Cl | —OH | |
| 15.171 | H | Cl | —OCH₃ | |
| 15.172 | H | Cl | —O—C₂H₅ | |
| 15.173 | H | Cl | —O—CH(CH₃)₂ | |
| 15.174 | H | Cl | —O—CH₂—C≡CH | |
| 15.175 | H | Cl | —O—CH₂—CH=CHCl | |
| 15.176 | H | Cl | —O—CH₂—C(Cl)=CH₂ | |
| 15.177 | H | Cl | —O—CH(CH₃)—C≡CH | |
| 15.178 | H | Cl | —O—CH₂—COOCH₃ | |
| 15.179 | H | Cl | —O—CH₂—COOC₂H₅ | |
| 15.180 | H | Cl | —O—CH(CH₃)—COOCH₃ | |
| 15.181 | H | Cl | —SH | |
| 15.182 | H | Cl | —SCH₃ | |
| 15.183 | H | Cl | —SC₂H₅ | |
| 15.184 | H | Cl | —S—CH(CH₃)₂ | |
| 15.185 | H | Cl | —S—CH₂—COOCH₃ | |
| 15.186 | H | Cl | —S—CH(CH₃)—COOCH₃ | |
| 15.187 | H | Cl | —S—CH₂—COOC₂H₅ | |
| 15.188 | H | Cl | —C(=N—OCH₃)—CN | |
| 15.189 | H | Cl | —C(CH₃)(O—CH(CH₃)—CH(CH₃)—O) | |
| 15.190 | H | Cl | —S—(cyclopropyl)—COOC₂H₅ | |
| 15.191 | H | Cl | —S—(cyclopropyl)—COOH | |

TABLE 15-continued
Compounds of formula Iq
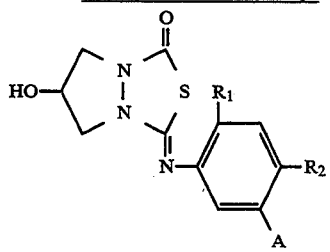
(Iq)
| Comp. No. | R₁ | R₂ | A | phys. data |
|---|---|---|---|---|
| 15.192 | H | Cl | 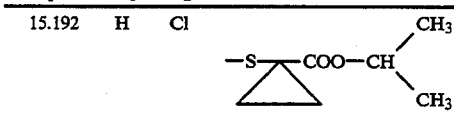 | |
| 15.193 | H | Cl | 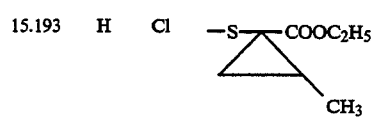 | |
| 15.194 | H | Cl | 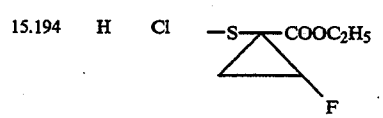 | |
| 15.195 | H | Cl | 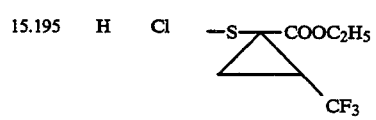 | |
| 15.196 | H | Cl | 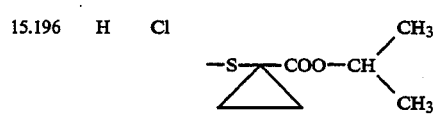 | |
| 15.197 | H | Cl | 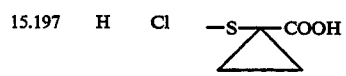 | |
| 15.198 | H | Cl | 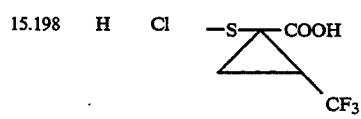 | |
| 15.199 | H | Cl | 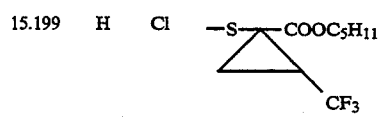 | |
| 15.200 | H | Cl | 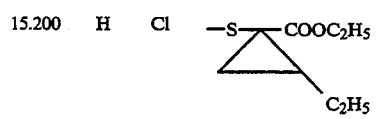 | |
| 15.201 | H | Cl | 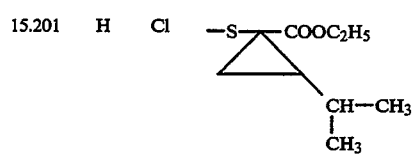 | |
| 15.202 | H | Cl | —NH—SO₂—C₂H₅ | |
| 15.203 | H | Cl | —NH—SO₂—CH₂—Cl | |
| 15.204 | F | CN | —COOH | |
| 15.205 | F | CN | 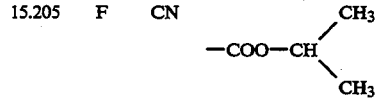 | |

TABLE 15-continued

Compounds of formula Iq

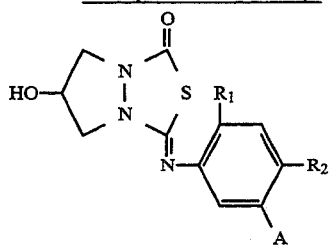

| Comp. No. | R₁ | R₂ | A | phys. data |
|---|---|---|---|---|
| 15.206 | F | CN | —O—CH(CH₃)₂ | |
| 15.207 | F | CN | —O—CH₂—C≡CH | |
| 15.208 | F | CN | —O—CH(CH₃)—C≡CH | |
| 15.209 | F | CN | —S—CH₂—COOCH₃ | |
| 15.210 | F | CN | —S—CH(CH₃)—COOCH₃ | |
| 15.211 | F | CN | —O—CH₂—COOCH₃ | |
| 15.212 | F | CN | —O—CH₂—COOC₅H₁₁ | |
| 15.213 | F | CN | —O—CH(CH₃)—COOC₂H₅ | |
| 15.214 | F | CN | —S—(cyclopropyl)—COOCH₃ | |
| 15.215 | F | CN | —S—(cyclopropyl)—COOC₂H₅ | |
| 15.216 | F | CN | —S—(cyclopropyl-F)—COOC₂H₅ | |
| 15.217 | F | CN | —S—(cyclopropyl)—COOH | |
| 15.218 | F | CN | —S—(cyclopropyl-F)—COOH | |
| 15.219 | F | CN | —S—(cyclopropyl-CF₃)—COOH | |
| 15.220 | F | CN | —S—(cyclopropyl)—COOC₂H₅ | |
| 15.221 | F | Br | —COOH | |
| 15.222 | F | Br | —COO—CH(CH₃)₂ | |
| 15.223 | F | Br | —OH | |
| 15.224 | F | Br | —O—CH(CH₃)₂ | |
| 15.225 | F | Br | —O—CH₂—C≡CH | |
| 15.226 | F | Br | —O—CH(CH₃)—C≡CH | |
| 15.227 | F | Br | —O—CH₂COOCH₃ | |

TABLE 15-continued

Compounds of formula Iq

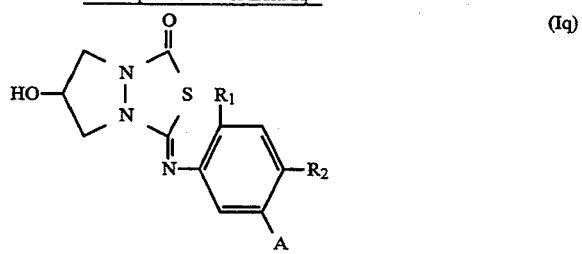

| Comp. No. | R₁ | R₂ | A | phys. data |
|---|---|---|---|---|
| 15.228 | F | Br | —O—CH₂—COOC₅H₁₁ | |
| 15.229 | F | Br | —S—CH₂—COOCH₃ | |
| 15.230 | F | Br | —S—△—COOC₂H₅ | |
| 15.231 | F | Br | —S—△—COOH, F | |
| 15.232 | F | Br | —S—△—COOC₂H₅, F | |
| 15.233 | F | Cl | —S—CH₂COOH | |

B. Formulation Examples for liquid active ingredients of formula I (throughout, percentages are by weight)

| 1. Emulsifiable concentrates | a) | b) | c) |
|---|---|---|---|
| a compound of Tables 1–15 | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2. Solutions | a) | b) | c) | d) |
|---|---|---|---|---|
| a compound of Tables 1–15 | 80% | 10% | 5% | 95% |
| propylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of micro-drops.

| 3. Granules | a) | b) | c) | d) |
|---|---|---|---|---|
| a compound of Tables 1–15 | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in methylene chloride, the solution is sprayed onto the carrier, and the solvent is subsequently evaporated off in vacuo.

| 4. Dusts | a) | b) |
|---|---|---|
| a compound of Tables 1–15 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation Examples for solid active ingredients of formula I (throughout, percentages are by weight)

| 5. Wettable powders | a) | b) | c) |
|---|---|---|---|
| a compound of Tables 1–15 | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 6. Emulsifiable concentrate | |
|---|---|
| a compound of Tables 1–15 | 10% |
| octylphenol polyethylene glycol ether (4–5 mol of ethylene oxide) | 3% |

| 6. Emulsifiable concentrate | |
|---|---|
| calcium dodecylbenzenesulfonate | 3% |
| castor oil polyglycol ether (36 mol of ethylene oxide) | 4% |
| cyclohexanone | 30% |
| xylene mixture | 50% |

Emulsions of any required concentration can be obtained from this concentrate by dilution with water.

| 7. Dusts | a) | b) |
|---|---|---|
| a compound of Tables 1–15 | 5% | 8% |
| talcum | 95% | — |
| kaolin | — | 92% |

Ready-for-use dusts are obtained by mixing the active ingredient with the carrier and grinding the mixture in a suitable mill.

| 8. Extruder granules | |
|---|---|
| a compound of Tables 1–15 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| 9. Coated granules | |
|---|---|
| a compound of Tables 1–15 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| 10. Suspension concentrate | |
|---|---|
| a compound of Tables 1–15 | 40% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil in the form of a 75% aqueous emulsion | 1% |
| water | 32% |

The finely ground active ingredient is intimately mixed with the adjuvants, giving a suspension concentrate from which suspensions of any desired concentration can be obtained by dilution with water.

C. Biological Examples:

Example B 1

Description of test for preemergence herbicidal action

The seeds of monocotyledonous and dicotyledonous test plants are sown in plastic pots containing standard soil. Immediately after sowing, an aqueous suspension of the test compounds, prepared from a 25% wettable powder formulation (Formulation Example 5), corresponding to a concentration of 2 kg of a.i./ha (500 l water/ha) is applied. The test plants are then cultivated in a greenhouse under optimum conditions. After 3 weeks the test is evaluated in accordance with a scale of nine ratings (1=total damage, 9=no action). Ratings of 1 to 4 (especially 1 to 3) indicate good to very good herbicidal action. The same results are obtained with solutions (Formulation Example 2), dispersible granules (Formulation Example 3), an emulsifiable concentrate (Formulation Examples 1 and 6) and a suspension concentrate (Formulation Example 10), dusts (Formulation Examples 4 and 7) and extruder granules and coated granules (Formulation Examples 8 and 9).

Test plants: Avena, Setaria, Sinapis, Stellaria

The compounds of Tables 1–15 exhibit pronounced herbicidal action in this test. Examples of the good herbicidal action are listed in Table B 1.

TABLE B1

| | Preemergence action | | | | |
|---|---|---|---|---|---|
| Comp. No. | Conc. [kg a.i/ha] | Avena | Setaria | Sinapis | Stellaria |
| 1.075 | 2 | 3 | 1 | 1 | 1 |
| 3.005 | 2 | 1 | 1 | 1 | 1 |
| 3.075 | 2 | 2 | 1 | 1 | 1 |
| 6.075 | 2 | 4 | 1 | 1 | 5 |
| 8.001 | 2 | 4 | 1 | 1 | 1 |

Example B2

Description of test for postemergence herbicidal action (contact herbicide)

Monocotyledonous and dicotyledonous test plants are raised in a greenhouse in plastic pots containing standard soil and in the 4- to 6-leaf stage are sprayed with an aqueous suspension of the test compounds, prepared from a 25% wettable powder formulation (Formulation Example 5), corresponding to a concentration of 2 kg of a.i./ha (500 l water/ha). The test plants are then grown on in the greenhouse under optimum conditions. After about 18 days the test is evaluated in accordance with a scale of nine ratings (1=total damage, 9=no action). Ratings of 1 to 4 (especially 1 to 3) indicate good to very good herbicidal action. The same results are obtained with solutions (Formulation Example 2), dispersible granules (Formulation Example 3), an emulsifiable concentrate (Formulation Examples 1 and 6) and a suspension concentrate (Formulation Example 10), dusts (Formulation Examples 4 and 7) and extruder granules and coated granules (Formulation Examples 8 and 9).

Test plants: Avena, Setaria, Sinapis, Stellaria

In this test also, the compounds of formula I according to the examples given in Tables 1 to 15 exhibit good herbicidal action.

Examples of the good herbicidal action of compounds of formula I are given in Table B2.

TABLE B2

| | Postemergence action | | | | |
|---|---|---|---|---|---|
| Comp. No. | Conc. [kg a.i/ha] | Avena | Setaria | Sinapis | Stellaria |
| 1.075 | 2 | 4 | 2 | 1 | 2 |
| 3.005 | 2 | 2 | 1 | 1 | 1 |
| 3.075 | 2 | 2 | 1 | 1 | 1 |
| 3.105 | 2 | 6 | 2 | 1 | 2 |
| 8.001 | 2 | 2 | 2 | 1 | 1 |

What is claimed is:

1. A thiadiazabicyclooctane of formula I

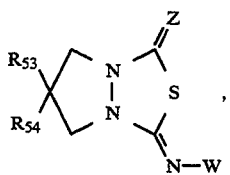

wherein
Z is oxygen or sulfur;
$R_{53}$ is $C_1$-$C_6$alkyl,
$R_{54}$ is $C_1$-$C_6$alkoxy, $C_3$-$C_6$alkenyloxy, $C_3$-$C_6$alkynyloxy, hydroxy or $C_1$-$C_6$haloalkoxy; or
$R_{53}$ and $R_{54}$, together with the carbon atom to which they are bonded, form an unsubstituted 3-, 4-, 5- or 6-membered saturated carbocylic ring;
W is a group of formulae $W_1$ to $W_{10}$ (W₁)
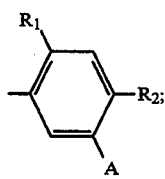

(W₂)

(W₃)
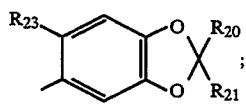

(W₄)
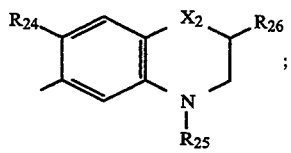

(W₅)
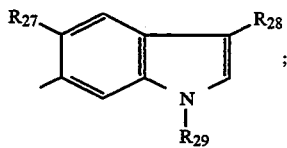

(W₆)
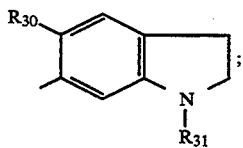

(W₇)
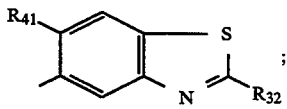

(W₈)
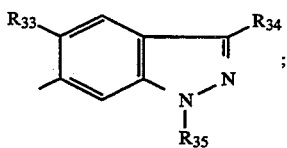

(W₉)
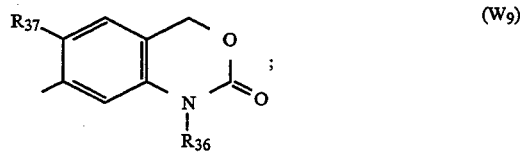

or (W₁₀)
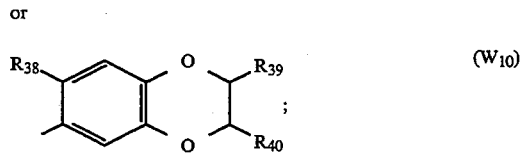

wherein
$R_1$, $R_{22}$, $R_{23}$, $R_{24}$, $R_{27}$, $R_{30}$, $R_{33}$, $R_{38}$ and $R_{41}$ are each independently of the others hydrogen or halogen;
$R_2$ is hydrogen, cyano, nitro, halogen, $C_1$-$C_4$alkyl, $C_1$-$C_4$haloalkoxy or $C_1$-$C_4$haloalkyl;
A is hydrogen, cyano, nitro,

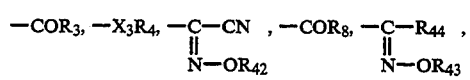

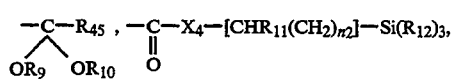

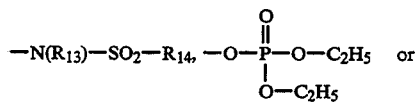

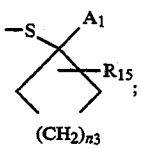

$A_1$ is cyano or —$COR_{16}$;
$R_3$ is halogen, —$X_4$—$R_5$, amino, $C_1$-$C_4$alkylamino, di-$C_1$-$C_4$alkylamino, $C_2$-$C_4$haloalkylamino, di-$C_2$-$C_4$haloalkylamino, $C_1$-$C_4$-dalkoxyalkylamino, di-$C_1$-$C_4$alkoxyalkyl-amino, $C_3$- or $C_4$-alkenylamino, diallylamino,-N-pyrrolidino, -N-piperidino, -N-morpholino, -N-thiomorpholino, -N-piperazino, —O—N=C($CH_3$)—$CH_3$ or —O—$CH_2$—$CH_2$—O—N=C($CH_3$)—$CH_3$;
$R_4$, $R_{42}$ and $R_{43}$ are each independently of the others hydrogen, $C_1$-$C_{10}$alkyl, $C_1$-$C_4$alkoxy-$C_1$-$C_4$alkyl, $C_1$-$C_4$alkylthio-$C_1$-$C_4$alkyl, di-$C_1$-$C_4$alkylamino-$C_1$-$C_4$alkyl, $C_1$-$C_8$haloalkyl, $C_2$-$C_8$alkenyl, $C_2$-$C_8$haloalkenyl, $C_3$-$C_8$alkynyl, $C_3$-$C_7$cycloalkyl, halo-$C_3$-$C_7$cycloalkyl, $C_1$-$C_8$alkylcarbonyl, allylcarbonyl, $C_3$-$C_7$cycloalkylcarbonyl, benzoyl that is unsubstituted or is substituted at the phenyl ring by one to three identical or different substituents selected from halogen, $C_1$-$C_4$alkyl, $C_1$-$C_4$haloalkyl, $C_1$-$C_4$haloalkoxy and $C_1$-$C_4$alkoxy; $C_1$-$C_6$alkyl substituted by cyano, nitro, carboxy, $C_1$-$C_8$alkylthio-$C_1$-$C_8$alkoxycarbonyl, phenyl, halophenyl, $C_1$-$C_4$alkylphenyl, $C_1$-$C_4$alkoxyphenyl, $C_1$-$C_4$haloalkylphenyl, $C_1$-$C_4$haloalkoxyphenyl, $C_1$-$C_6$alkoxycarbonyl, $C_1$-$C_4$alkoxy-$C_1$-$C_8$alkoxycarbonyl, $C_3$-$C_8$lkenyloxycarbonyl, $C_3$-$C_8$alkynyloxycarbonyl, $C_1$-$C_8$alkylthiocarbonyl, $C_3$-$C_8$alkenylthiocarbonyl, $C_3$-$C_8$alkynylthiocarbonyl, carbamoyl, $C_1$-$C_4$alkylaminocarbonyl, di-$C_1$-$C_4$alkylaminocarbonyl; phenylaminocarbonyl that is unsubstituted or is substituted at the phenyl by one to three identical or different substituents selected from halogen, $C_1$-$C_4$alkyl, $C_1$-$C_4$haloakkyl, $C_1$-$C_4$haloalkoxy and $C_1$-$C_4$alkoxy or by one substituent selected from cyano and nitro; dioxolan-2-yl that is unsubstituted or substituted by one or two $C_1$-$C_4$alkyl radicals; or dioxanyl that is unsubstituted or substituted by one or two $C_1$-$C_4$alkyl radicals;

$R_5$ is hydrogen, $C_1$-$C_{10}$ alkyl, $C_1$-$C_4$alkoxy-$C_1$-$C_4$alkyl, $C_2$-$C_8$haloalkyl, $C_1$-$C_{10}$ alkyl-thio-$C_1$-$C_4$alkyl, di-$C_1$-$C_4$alkylamino-$C_1$-$C_4$alkyl, cyano-$C_1$-$C_8$alkyl, $C_3$-$C_8$alkenyl, $C_3$-$C_8$haloalkenyl, $C_3$-$C_8$alkynyl, $C_3$-$C_7$cycloalkyl, $C_3$-$C_7$cycloalkyl-$C_1$-$C_4$alkyl, halo-$C_3$-$C_7$cycloalkyl, or benzyl that is unsubstituted or is substituted at the phenyl ting by one to three identical or different substituents selected from halogen, $C_1$-$C_4$alkyl, $C_1$-$C_4$haloalkyl, $C_1$-$C_4$haloalkoxy and $C_1$-$C_4$alkoxy; or is an alkali metal, an alkaline earth metal or an ammonium ion; or is the group —[$CHR_6(CH_2)_{n4}$]—$COOR_7$;

$R_6$, $R_{20}$, $R_{21}$, $R_{26}$, $R_{28}$, $R_{32}$, $R_{34}$, $R_{39}$, $R_{40}$, $R_{46}$, $R_{47}$, $R_{49}$, $R_{50}$, $R_{51}$ and $R_{52}$ are each independently of the others hydrogen or $C_1$-$C_4$alkyl;

$R_7$ and $R_{48}$ are each independently of the other hydrogen, $C_1$-$C_6$alkyl, $C_3$-$C_8$alkenyl, $C_3$-$C_8$alkynyl, $C_1$-$C_8$alkoxy-$C_2$-$C_8$alkyl, $C_1$-$C_8$alkylthio-$C_1$-$C_8$alkyl or $C_3$-$C_7$cycloalkyl;

$R_8$ is hydrogen or $C_1$-$C_4$alkyl;

$R_{44}$ and $R_{45}$ are each independently of the other hydrogen, $C_1$-$C_4$alkyl, $C_1$-$C_4$haloalkyl or $C_1$-$C_4$alkoxy-$C_1$-$C_4$alkyl;

$R_9$ and $R_{10}$ are each independently of the other $C_1$-$C_4$alkyl, $C_2$-$C_4$haloalkyl or $C_2$-$C_8$alkoxyalkyl; or $R_9$ and $R_{10}$ together are an ethano-, a propano- or a cyclohexane-1,2-diyl bridge, those groups either being unsubstituted or being substituted by one or two radicals selected from the group $C_1$-$C_4$alkyl, $C_1$-$C_4$haloalkyl and $C_1$-$C_4$hydroxyalkyl;

$R_{11}$ is hydrogen, $C_1$-$C_5$alkyl or $C_3$-$C_7$alkenyl;

$R_{12}$ is $C_1$-$C_8$alkyl;

$R_{13}$ is hydrogen, $C_1$-$C_5$alkyl, benzyl, $C_1$-$C_4$haloalkyl, $C_3$-$C_8$alkenyl or $C_3$-$C_8$halkynyl;

$R_{14}$ is $C_1$-$C_6$alkyl, $C_1$-$C_5$haloalkyl or di-$C_1$-$C_4$alkylamino;

$R_{15}$ is hydrogen, fluorine, chlorine, bromine, $C_1$-$C_4$alkyl or trifluoromethyl;

$R_{16}$ is chlorine, —$X_5$—$R_{17}$, amino, $C_1$-$C_4$alkylamino, di-$C_1$-$C_4$alkylamino, $C_2$-$C_4$haloalkylamino, di-$C_2$-$C_4$haloalkylamino, $C_1$-$C_4$alkoxyalkylamino, di-$C_1$C_4$alkoxyalkylamino, $C_3$-$C_4$alkenylamino, diallylamino, -N-pyrrolidino, -N-piperidino, -N-morpholino, -N-thiomorpholino, -N-piperazino, or the group —O—N=C(CH_3)—CH_3, —O—CH_2—CH_2—O—N=C(CH_3)—CH_3 or —N(OR_{46})—R_6;

$R_{17}$ is hydrogen, $C_1$-$C_{10}$alkyl, $C_1$-$C_4$alkoxy-$C_1$-$C_4$alkyl, $C_2$-$C_8$haloalkyl, $C_1$-$C_{10}$alkyl-thio-$C_1$-$C_4$alkyl, di-$C_1$-$C_4$alkylamino-$C_1$-$C_4$alkyl, cyano-$C_1$-$C_8$alkyl, $C_3$-$C_8$alkenyl, $C_3$-$C_8$haloalkenyl, $C_3$-$C_8$alkynyl, $C_3$-$C_7$cycloalkyl, $C_3$-$C_7$cycloalkyl-$C_1$-$C_4$alkyl, halo-$C_3$-$C_7$cycloalkyl, or benzyl that is unsubstituted or is substituted at the phenyl ring by one to three identical or different substituents selected from halogen, $C_1$-$C_4$alkyl, $C_1$-$C_4$haloalkyl, $C_1$-$C_4$haloalkoxy and $C_1$-$C_4$alkoxy; or is an alkali metal, an alkaline earth metal or an ammonium ion, or is the group —[$CHR_{47}$—$(CH_2)_m$]—$COOR_{48}$ or —[$CHR_{49}$—$(CH_2)_t$—$Si(R_{18})_3$];

m is 0, 1, 2, 3 or 4;

t is 0, 1, 2, 3 or 4;

$R_{18}$ is $C_1$-$C_4$alkyl;

$R_{19}$ is hydrogen, $C_1$-$C_6$alkyl, $C_2$-$C_4$alkenyl or $C_2$-$C_6$alkynyl; halo-substituted $C_1$-$C_6$alkyl, $C_2$-$C_4$alkenyl or $C_3$-$C_6$alkynyl; $C_1$-$C_4$alkoxy-$C_1$-$C_4$alkyl, $C_1$-$C_4$alkoxy-$C_1$-$C_2$alkoxy-$C_1$-$C_2$alkyl, 1-phenylpropen-3-yl, $C_1$-$C_6$alkyl substituted by cyano or by $C_3$-$C_6$cycloalkyl; carboxy-$C_1$-$C_4$alkyl, $C_1$-$C_6$alkoxycarbonyl-$C_1$-$C_4$alkyl, $C_2$-$C_6$ haloalkoxycarbonyl-$C_1$-$C_4$alkyl, $C_1$-$C_4$ alkoxy-$C_1$-$C_2$alkoxycarbonyl-$C_1$-$C_4$alkyl, $C_1$-$C_6$alkoxycarbonyl-$C_1$-$C_2$alkoxycarbonyl-$C_1$-$C_4$alkyl, $C_3$-$C_6$cycloalkyl-$C_1$-$C_2$alkoxycarbonyl-$C_1$-$C_4$alkyl, $C_1$-$C_5$alkylaminocarbonyl-$C_1$-$C_4$alkyl, di-$C_1$-$C_4$alkylamino-$C_1$-$C_4$alkyl, di-$C_1$-$C_5$alkylaminocarbonyl-$C_1$-$C_4$alkyl, $C_3$-$C_6$cycloalkyl, $C_1$-$C_4$alkylthio-$C_1$-$C_4$alkyl, benzyl or halo-substituted benzyl, $C_1$-$C_4$alkylsulfonyl, $C_3$-$C_6$alkenyloxy-$C_1$-$C_4$alkyl, $C_1$-$C_4$alkoxycarbonyl, $C_1$-$C_8$alkylcarbonyl,

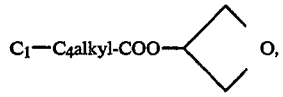

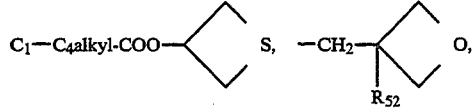

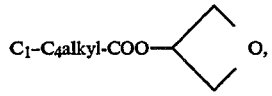

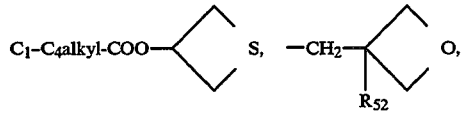

$C_1$-$C_4$alkylthiocarbonyl-$C_1$-$C_4$alkyl, or the group —[$CHR_{47}$-$(CH_2)_m$]$COX_6$—$CHR_{47}$—$(CH_2)_m$—$COOR_{48}$;

$R_{25}$, $R_{29}$, $R_{31}$, $R_{35}$ and $R_{36}$ are each independently of the others hydrogen, $C_1$-$C_4$alkyl, $C_1$-$C_6$haloalkyl, $C_3$-$C_8$alkenyl, $C_3$-$C_8$haloalkenyl, $C_3$-$C_8$alkynyl, $C_1$-$C_4$alkoxy-$C_1C_8$alkyl, cyano-$C_1$-$C_4$alkyl, $C_1$-$C_8$alkoxycarbonyl-$C_1$-$C_4$alkyl, $C_3$-$C_7$cycloalkyl, $C_3$-$C_7$cycloalkyl-$C_1$-$C_4$alkyl, benzyl, $C_1$-$C_4$alkyl substituted by -N-morpholino, -N-thiomorpholino or by -N-piperazino, di-$C_1$-$C_4$alkylamino-$C_1C_4$alkyl, $C_1C_4$alkylaminocarbonyl-$C_1$-$C_4$alkyl, di-$C_1$-$C_4$alkylaminocarbonyl-$C_1C_4$alkyl, $C_1$-$C_4$alkoxycarbonyl or $C_1$-$C_4$alkylcarbonyl;

$X_1$, $X_2$, $X_3$, $X_4$, $X_5$ and $X_6$ are each independently of the others oxygen or sulfur, $n_1$, $n_2$, $n_3$ and $n_4$ are each independently of the others 0, 1, 2, 3 or 4; with the provisos that at least one of $R_1$, $R_2$ and A is different from hydrogen; and that when $R_{53}$ is hydrogen, $R_{54}$ is different frown $C_1$-$C_4$alkyl; or a salt or a stereoisomer thereof.

2. A compound according to claim 1 wherein Z is oxygen.

3. A compound according to claim 1 of formula Ia

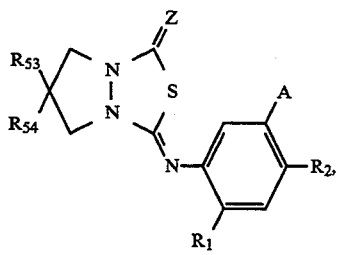

wherein Z, A, $R_1$, $R_2$, $R_{53}$ and $R_{54}$ are as defined in claim 1.

4. A compound according to claim 3 wherein A is

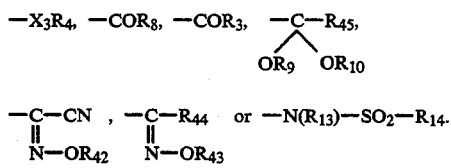

5. A compound according to claim 4 wherein $X_3$ is sulfur and $R_4$ is $C_1$-$C_6$alkyl substituted by $C_1$-$C_6$alkoxycarbonyl.

6. A compound according to claim 3 wherein $R_1$ and $R_2$ are halogen.

7. A compound according to claim 3 wherein $R_1$ is fluorine and $R_2$ is chlorine.

8. A compound according to claim 1 of formula Ib

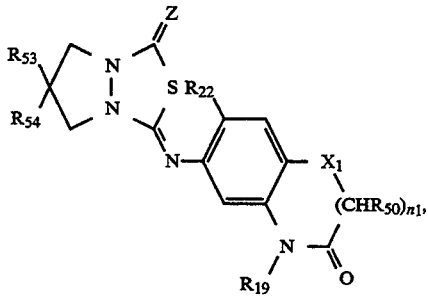

wherein Z, $R_{19}$, $R_{22}$, $X_1$, $R_{50}$, $R_{53}$, $R_{54}$ and $n_1$ are as defined in claim 1.

9. A compound according to claim 8 wherein $R_{19}$ is $C_1$-$C_4$alkyl, $C_3$- or $C_4$-alkenyl, $C_3$- or $C_4$-haloalkenyl, $C_3$-$C_6$alkynyl, $C_1$-$C_4$alkoxy-$C_1$-$C_4$alkyl, cyano-$C_1$-$C_4$alkyl, $C_1$-$C_6$alkoxycarbonyl-$C_1$-$C_4$alkyl, $C_3$-$C_6$cycloalkyl, $C_3$-$C_6$cycloalkyl-$C_1$-$C_4$alkyl, benzyl, di-$C_1$-$C_4$alkylamino-$C_1$-$C_4$alkyl, $C_1$-$C_4$alkylaminocarbonyl-$C_1$-$C_4$alkyl, di-$C_1$-$C_4$alkylaminocarbonyl-$C_1$-$C_4$alkyl, $C_1$-$C_4$alkoxycarbonyl or $C_1$-$C_4$alkylcarbonyl.

10. A compound according to claim 9 wherein Z is oxygen;

$R_{19}$ is $C_1$-$C_3$alkyl, $C_1C_3$alkoxycarbonyl-$C_1$- or -$C_2$-alkyl or $C_3$- or $C_4$-alkynyl;
$R_{22}$ is hydrogen or fluorine;
$R_{50}$ is hydrogen; and
$n_1$ is 0 or 1.

11. A compound according to claim 1 wherein $R_{53}$ and $R_{54}$ are $C_1$-$C_4$alkyl.

12. A compound according to claim 11 wherein $R_{53}$ and $R_{54}$ are each independently of the other methyl or ethyl.

13. A compound according to claim 1 wherein $R_{53}$ and $R_{54}$, together with the carbon atom to which they are bonded, form an unsubstituted 3- or 5-membered saturated ring.

14. A compound according to claim 1 wherein $R_{53}$ is hydrogen; and $R_{54}$ is $C_1$-$C_3$alkoxy, $C_3$-$C_5$alkenyloxy, $C_3$-$C_5$alkynyloxy or $C_1$-$C_3$haloalkoxy.

15. A compound according to claim 14 wherein $R_{54}$ is $C_1$-$C_3$alkoxy or $C_1$-$C_3$haloalkoxy.

16. A compound according to claim 15 wherein $R_{54}$ is methoxy, isopropoxy or difluoromethoxy.

17. A compound according to claim 1 selected from the group consisting of:
8-(4-chloro-2-fluoro-5-isopropoxy-phenylimino)-3,3-dimethyl-7-thia-1,5-diazabicyclo[3.3.0]octan-6-one;
8-(4-chloro-2-fluoro-5-isopropoxy-phenylimino)-3-methoxy-7-thia-1,5-diazabicyclo-[3.3.0]octan-6-one;
8-(4-chloro-2-fluoro-5-isopropoxy-phenylimino)-3-difluoromethoxy-7-thia-1,5-diazabicyclo[3.3.0octan-6-one; and
8-(4-chloro-2-fluoro-5-isopropoxy-phenylimino)-3,3-ethanediyl-7-thia-1,5-diazabicyclo-[3.3.0]octan-6-one.

18. A herbicidal and plant-growth-inhibiting composition which comprises a compound of formula I or a salt thereof according to claim 1 in an agriculturally-suitable carrier.

19. A composition according to claim 18 which comprises from 0.1 to 95 percent by weight of a compound of formula I according to claim 1 in an agriculturally-suiatable carrier.

20. A method of controlling undesired plant growth, which method comprises treating the crop plants to be protected against weeds and treating the weeds and grasses with a compound of formula I according to claim 1 or with a composition comprising such a compound in an agriculturally-suitable carrier.

21. A method according to claim 20 which comprises applying a compound of formula I in an amount of from 0.001 to 2 kg per hectare in an agriculturally-suitable carrier.

22. A method according to claim 20 for the selective pre- or post-emergence control of weeds and grasses in crops of useful plants.

23. A method of inhibiting plant growth, which method comprises applying to the plants or to the locus thereof an effective amount of a compound of formula I according to claim 1 or of a composition comprising such a compound in an agriculturally-suitable carrier.

* * * * *